(12) United States Patent
Yen

(10) Patent No.: US 9,905,772 B2
(45) Date of Patent: Feb. 27, 2018

(54) MATERIAL FOR ORGANIC ELECTROLUMINESCENCE DEVICE AND USE THEREOF

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 422 days.

(21) Appl. No.: 14/854,000

(22) Filed: Sep. 14, 2015

(65) Prior Publication Data

US 2017/0077410 A1    Mar. 16, 2017

(51) Int. Cl.
| | | |
|---|---|---|
| H01L 51/00 | (2006.01) | |
| C07C 13/62 | (2006.01) | |
| C09K 11/06 | (2006.01) | |
| C09K 11/02 | (2006.01) | |
| C07D 403/10 | (2006.01) | |

(Continued)

(52) U.S. Cl.
CPC .......... H01L 51/0056 (2013.01); C07C 13/62 (2013.01); C07C 211/54 (2013.01);
(Continued)

(58) Field of Classification Search
None
See application file for complete search history.

(56) References Cited

U.S. PATENT DOCUMENTS

| 8,962,160 | B2 | 2/2015 | Yen et al. |
| 8,993,130 | B2 * | 3/2015 | Yen ..................... H01L 51/0058 257/40 |

(Continued)

FOREIGN PATENT DOCUMENTS

| CN | 104710980 A | * | 6/2015 | ............. C09K 11/06 |
| WO | 2008062636 A1 | | 5/2008 | |
| WO | 2012091471 A2 | | 7/2012 | |

*Primary Examiner* — Gregory D Clark

(57) ABSTRACT

The present invention discloses an organic material is represented by the following formula (1) or formula (2), the organic EL device employing the material as light emitting host or dopant of emitting layer, hole blocking layer (HBL), electron blocking layer (EBL), electron transport layer (ETL) and hole transport layer (HTL) can display good performance.

formula(1)

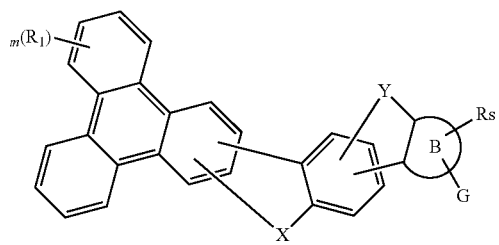

formula(2)

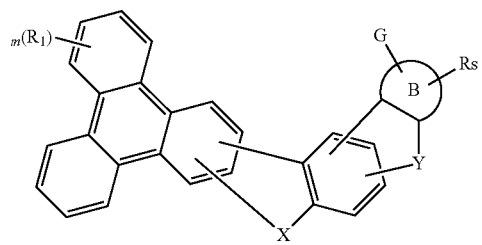

wherein B represents a fused ring hydrocarbon units with two to three rings, m represents an integer of 0 to 10, $R_1$, G, Rs, X and Y are the same definition as described in the present invention.

20 Claims, 3 Drawing Sheets

- 13 — metal electrode
- 12 — electron injection layer
- 11 — electron transport layer
- 10 — hole blocking layer
- 9 — emitting layer
- 8 — hole transport layer
- 7 — hole injection layer
- 6 — transparent electrode

(51) Int. Cl.
*C07D 491/048* (2006.01)
*C07D 495/04* (2006.01)
*C07C 211/54* (2006.01)
*C07D 307/91* (2006.01)
*C07D 251/24* (2006.01)
*C07D 239/26* (2006.01)
*C07D 471/04* (2006.01)
*C07D 279/22* (2006.01)
*C07D 209/86* (2006.01)
*H01L 51/50* (2006.01)

(52) U.S. Cl.
CPC ......... *C07D 209/86* (2013.01); *C07D 239/26* (2013.01); *C07D 251/24* (2013.01); *C07D 279/22* (2013.01); *C07D 307/91* (2013.01); *C07D 403/10* (2013.01); *C07D 471/04* (2013.01); *C07D 491/048* (2013.01); *C07D 495/04* (2013.01); *C09K 11/025* (2013.01); *C09K 11/06* (2013.01); *H01L 51/006* (2013.01); *H01L 51/0054* (2013.01); *H01L 51/0058* (2013.01); *H01L 51/0067* (2013.01); *H01L 51/0071* (2013.01); *H01L 51/0072* (2013.01); *C07C 2603/18* (2017.05); *C07C 2603/50* (2017.05); *C07C 2603/54* (2017.05); *C09K 2211/1007* (2013.01); *C09K 2211/1011* (2013.01); *C09K 2211/1014* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *H01L 51/5016* (2013.01); *H01L 51/5072* (2013.01); *H01L 51/5096* (2013.01)

(56) References Cited

U.S. PATENT DOCUMENTS

| | | |
|---|---|---|
| 2013/0048975 A1 | 2/2013 | Hong et al. |
| 2014/0151645 A1 | 6/2014 | Yen et al. |
| 2014/0175383 A1 | 6/2014 | Yen et al. |
| 2014/0209866 A1 | 7/2014 | Yen et al. |
| 2014/0231754 A1 | 8/2014 | Yen et al. |

* cited by examiner

MATERIAL FOR ORGANIC ELECTROLUMINESCENCE DEVICE AND USE THEREOF

FIELD OF INVENTION

The present invention generally relates to a material and organic electroluminescence (herein referred to as organic EL) device using the material. More specifically, the present invention relates to the material having general formula (1) or formula (2), an organic EL device employing the material as emitting host or dopant, hole blocking layer (HBL), electron blocking layer (EBL), electron transport layer (ETL) and hole transport layer (HTL).

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML) and an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC).

The phosphorescent organic EL utilizes both triplet and singlet excitons. Cause of longer lifetime and the diffusion length of triplet excitons compared to those of singlet excitons, the phosphorescent organic EL generally need an additional hole-blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the materials are also needed.

There continues to be a need for organic EL materials which is able to efficiently transport electrons or holes and block holes, with good thermal stability and more efficient EML materials for high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel material having general formula (1) or formula (2), used as emitting host or dopant, hole blocking layer (HBL), electron blocking layer (EBL), electron transport layer (ETL) and hole transport layer (HTL) have good charge carrier mobility and excellent operational durability can lower driving voltage and power consumption, increasing efficiency and half-life time of organic EL device.

SUMMARY OF THE INVENTION

A novel material can use as emitting host or dopant, hole blocking layer (HBL), electron blocking layer (EBL), electron transport layer (ETL) and hole transport layer (HTL) for organic EL and their use for organic EL device are provided. The material can overcome the drawbacks of the conventional materials like as shorter half-life time, lower efficiency and higher power consumption.

An object of the present invention is to provide the material which can be used as hole blocking layer (HBL) material, electron blocking layer (EBL) material for organic EL device and can efficiently confine excitons to transfer to electron transport layer or hole transport layer.

An object of the present invention is to provide the material which can be used as phosphorescent host material, fluorescent host material or fluorescent dopant of emitting layer for organic EL device and increase the efficiency and half-life time.

Another object of the present invention is to provide the material which can be used as hole transport layer (HTL) material, electron transport layer (ETL) material for organic EL device and improve the half-life time, lower driving voltage and lower power consumption.

The present invention has the economic advantages for industrial practice. Accordingly the present invention, the material which can be used for organic EL device is disclosed. The mentioned the material is represented by the following formula (1) or formula (2):

formula(1)

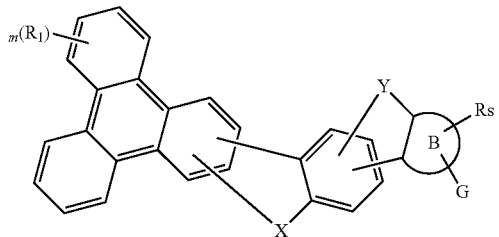

formula(2)

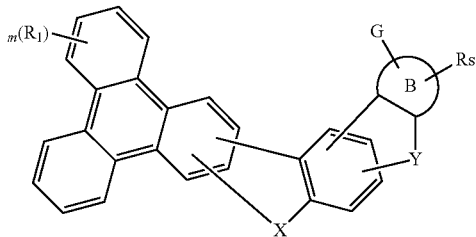

wherein B represents a fused ring hydrocarbon units with two or three rings, m represents an integer of 0 to 10, X and Y are divalent bridge selected from the atom or group consisting from O, S, $C(R_2)(R_3)$, $Si(R_4)(R_5)$, $NR_6$, G or $R_6$ are selected from the group consisting of a hydrogen, a halide, a substituted or unsubstituted aryl group having 6 to 60 carbon atoms or a substituted or unsubstituted heteroaryl group having 3 to 60 carbon atoms, and provided that G or $R_6$ represent a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ to $R_5$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

DESCRIPTION OF THE PREFERRED EMBODIMENTS

Figure 1:
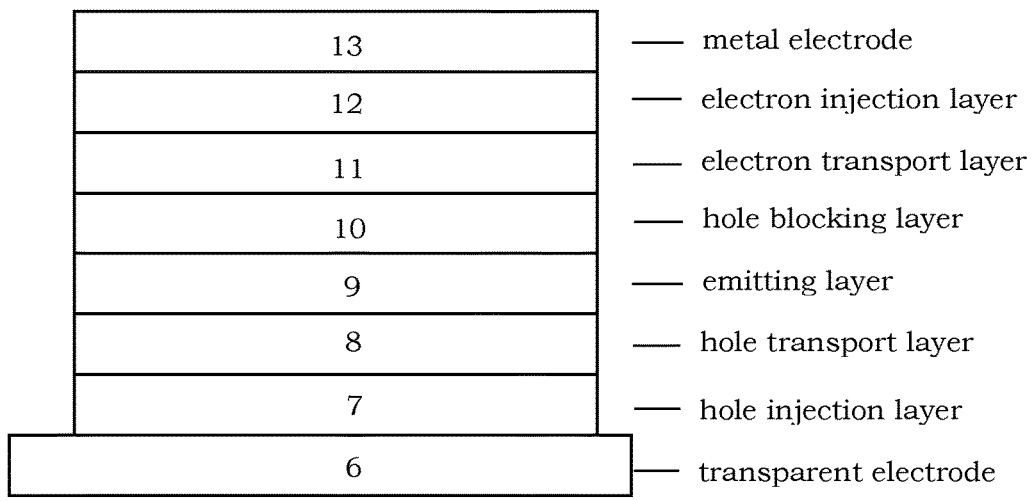
FIG. 1 show one example of organic EL device in the present invention. 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

What probed into the invention is the material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the material which can be used as emitting host or dopant, hole blocking layer (HBL), electron blocking layer (EBL), electron transport layer (ETL) and hole transport layer (HTL) for organic EL device are disclosed. The mentioned the material are represented by the following formula (1) or formula (2):

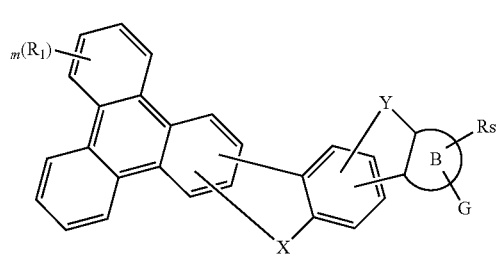

formula(1)

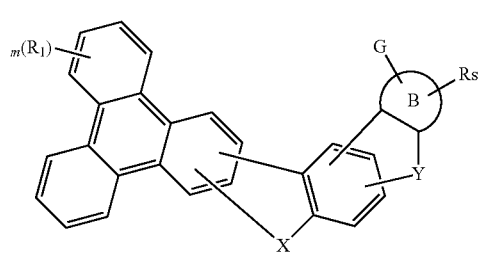

formula(2)

wherein B represents a fused ring hydrocarbon units with two or three rings, m represents an integer of 0 to 10, X and Y are divalent bridge selected from the atom or group consisting from O, S, C(R$_2$)(R$_3$), NR$_4$, Si(R$_5$)(R$_6$), G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, R$_1$ to R$_6$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned the material formula (1) or formula (2), wherein the G is consisting of group represented as follows:

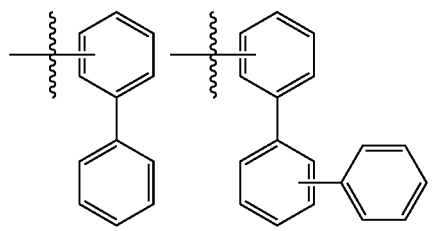

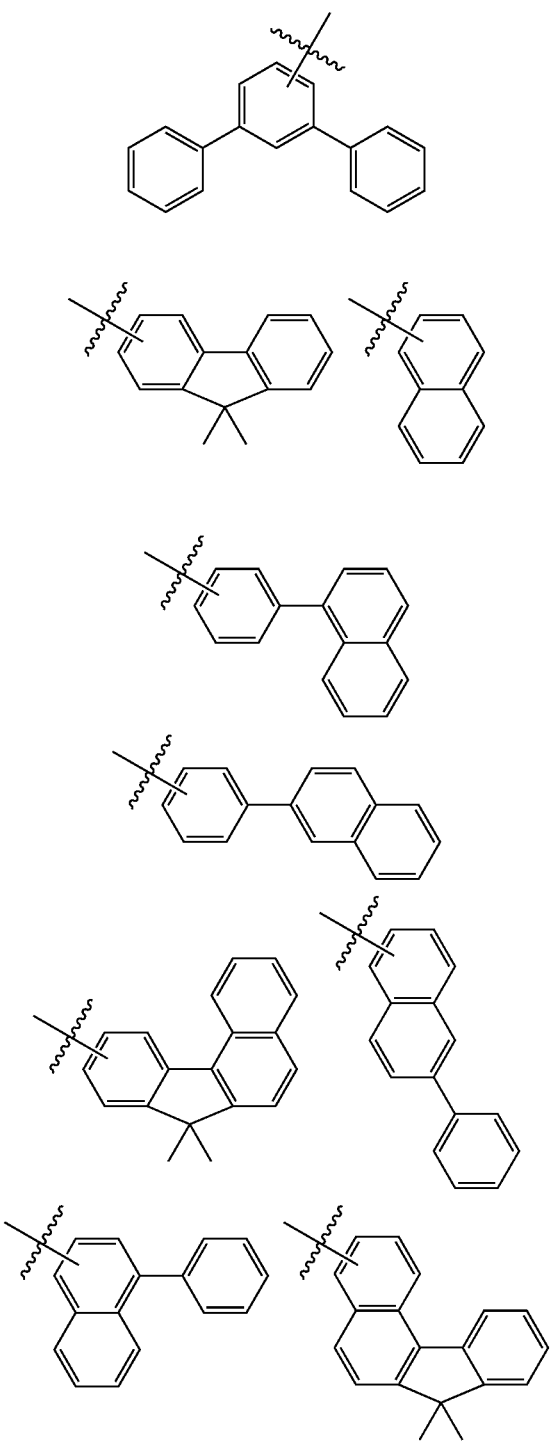

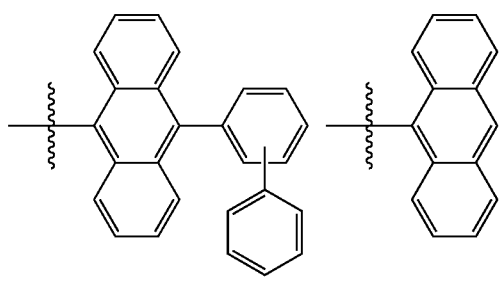
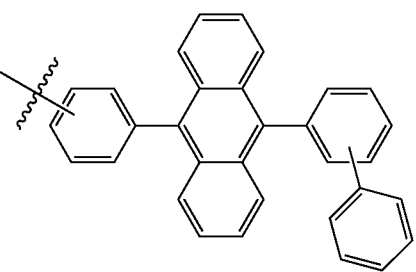
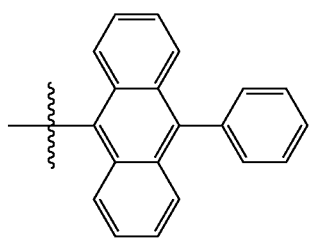
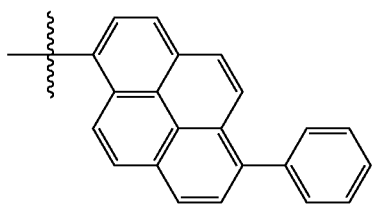
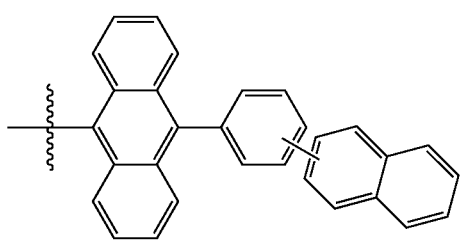
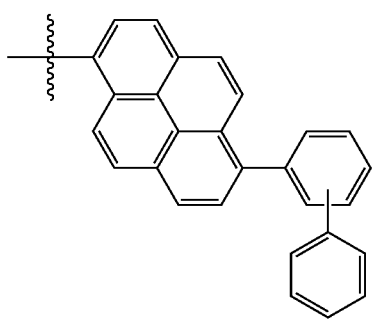
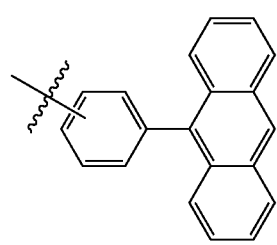
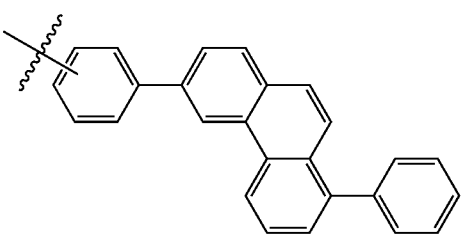
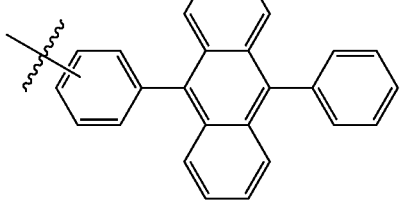
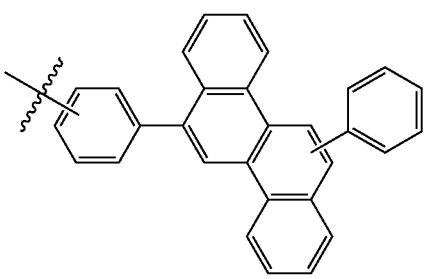
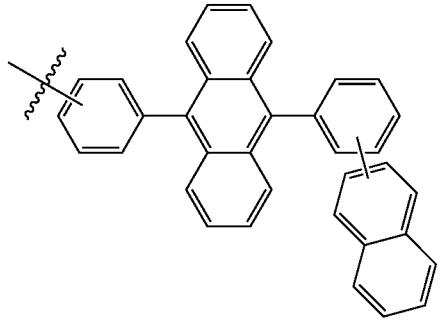
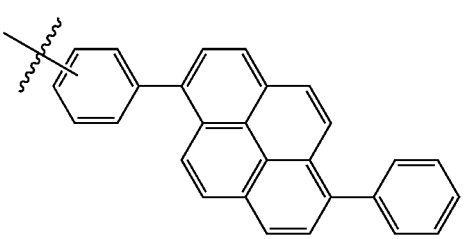

-continued
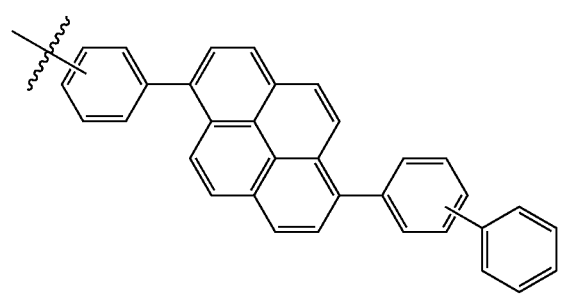
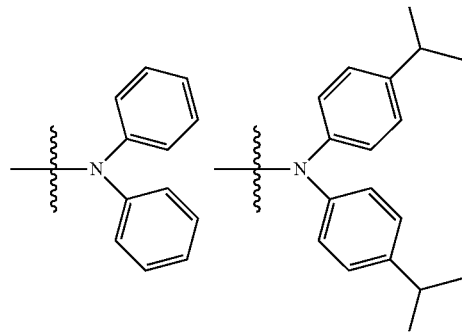
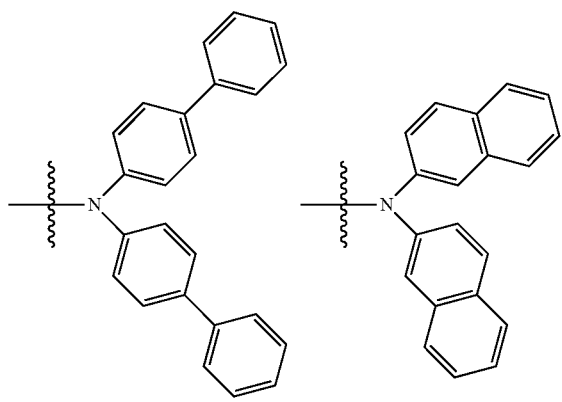
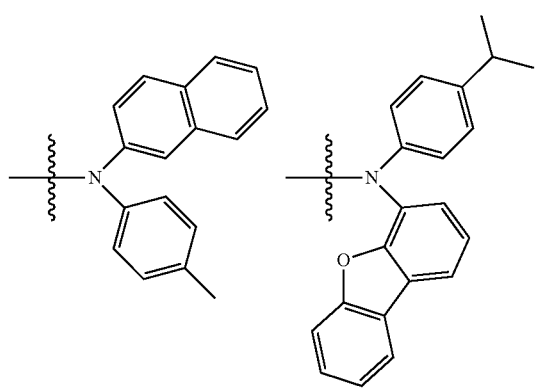
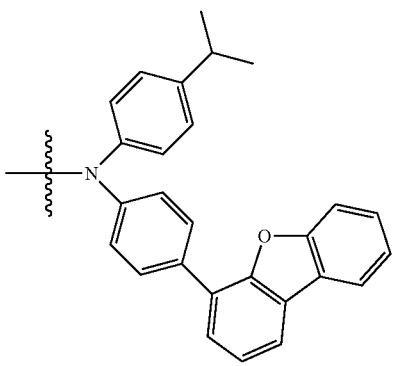
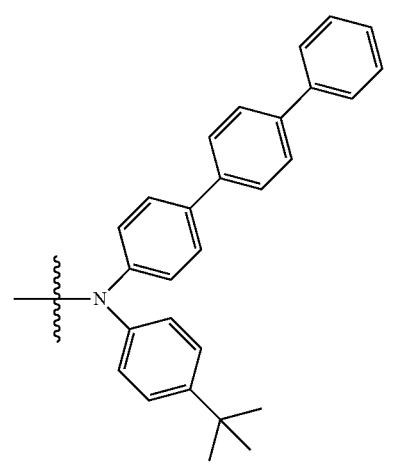
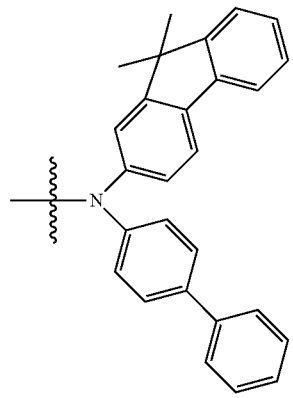
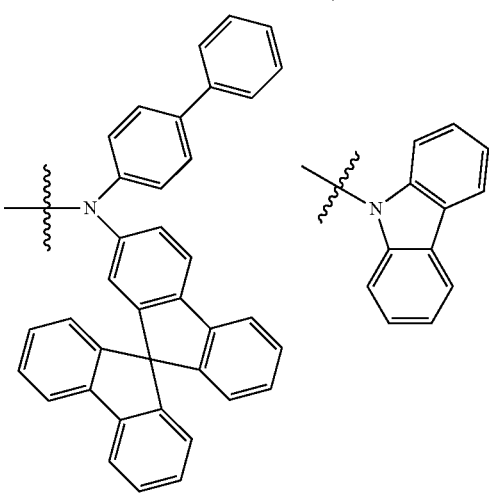

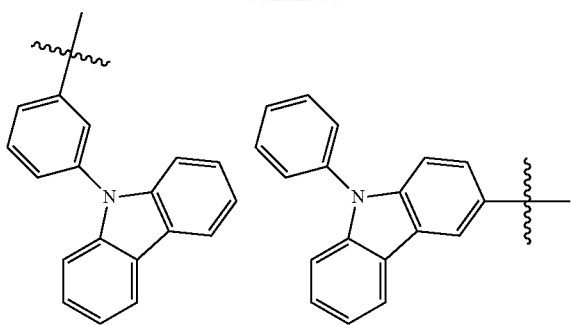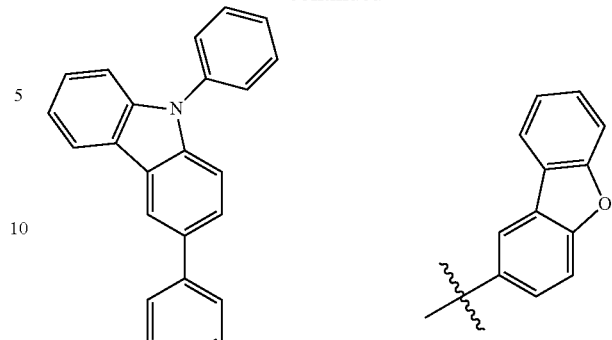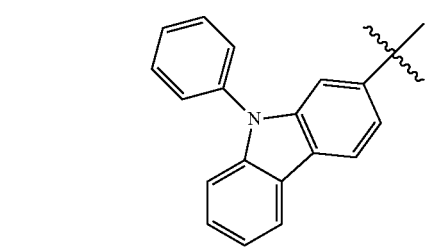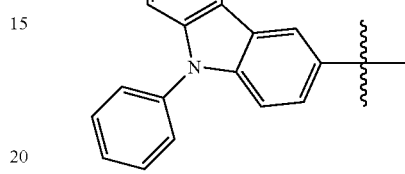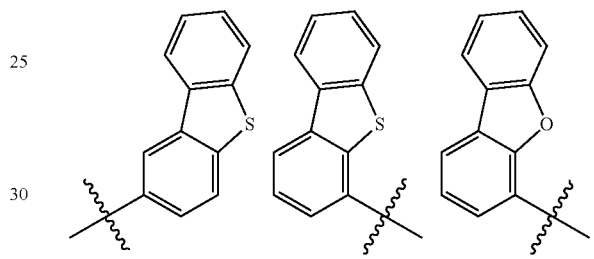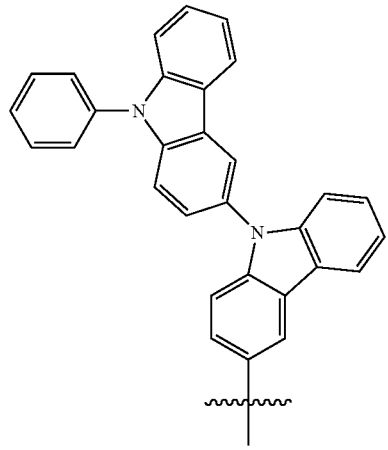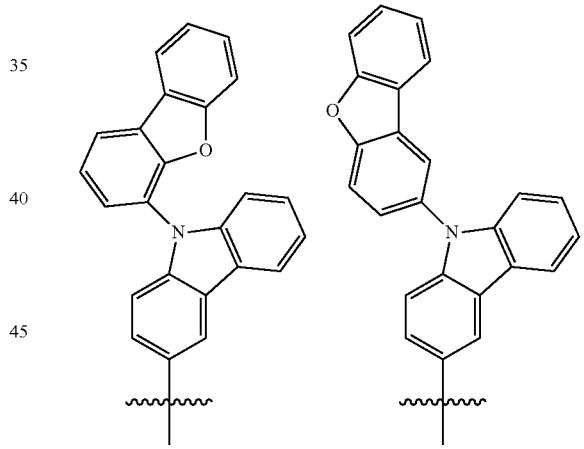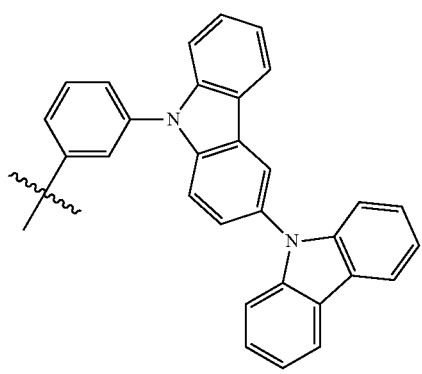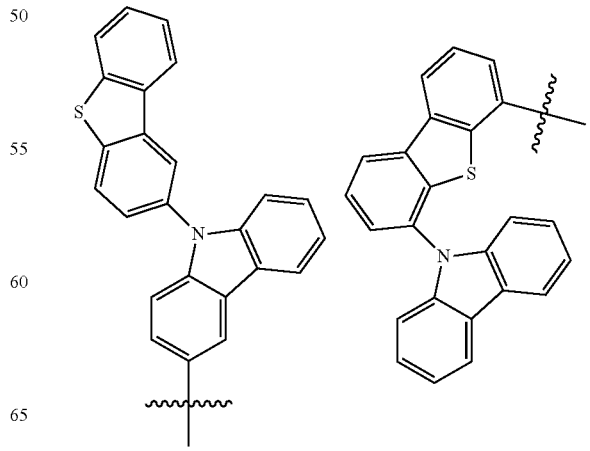

-continued
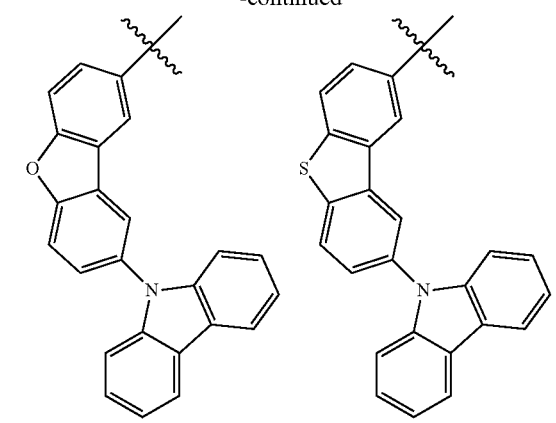
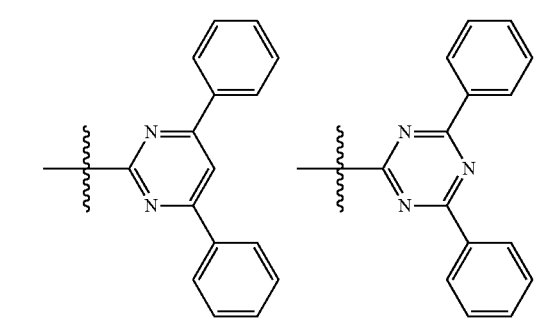
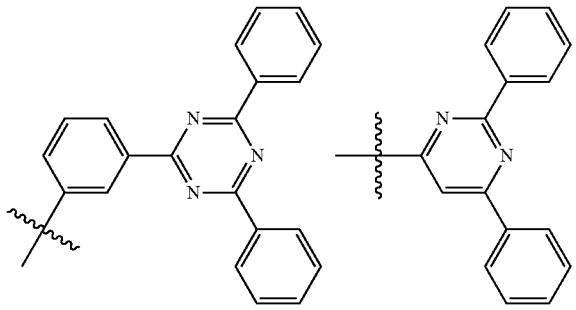
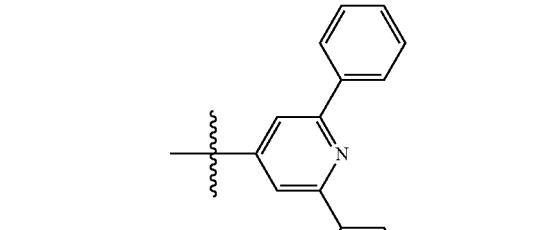
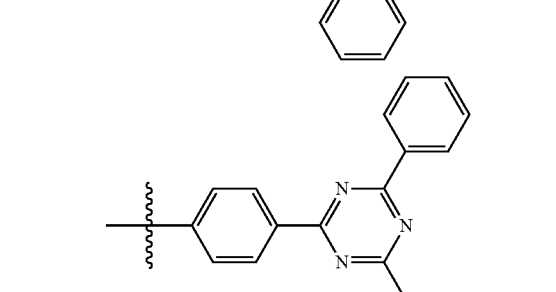
-continued
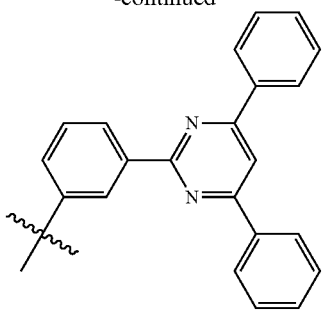
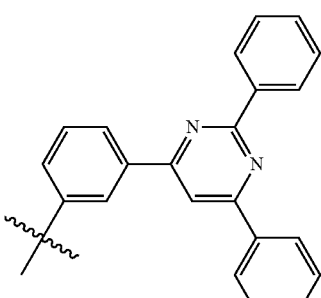
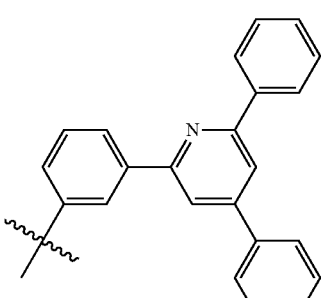
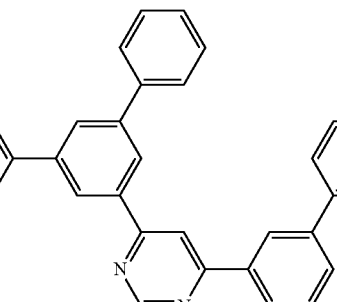

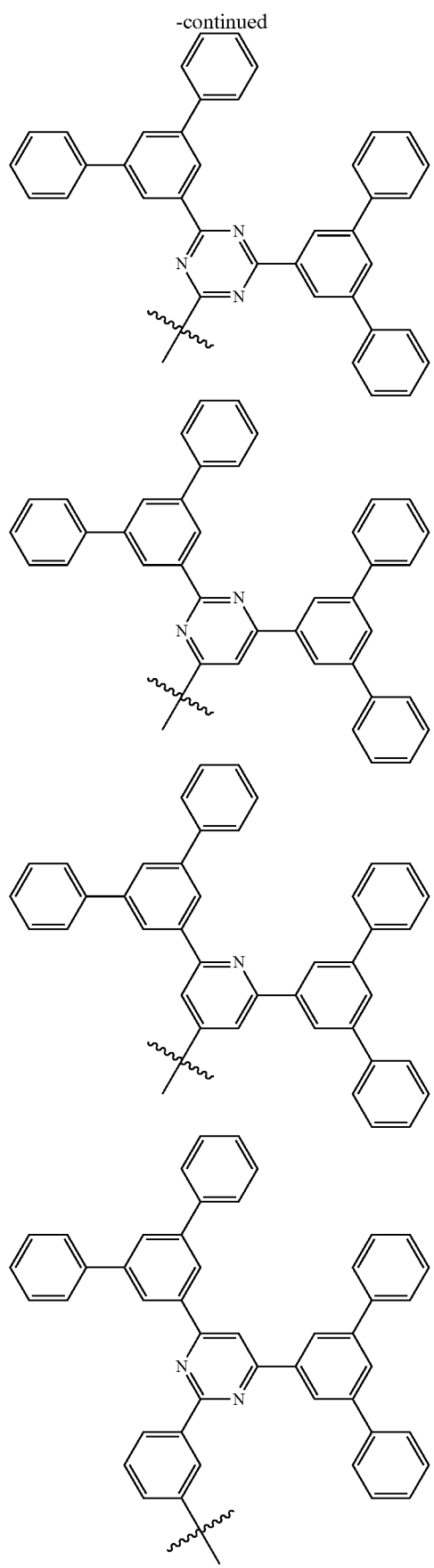
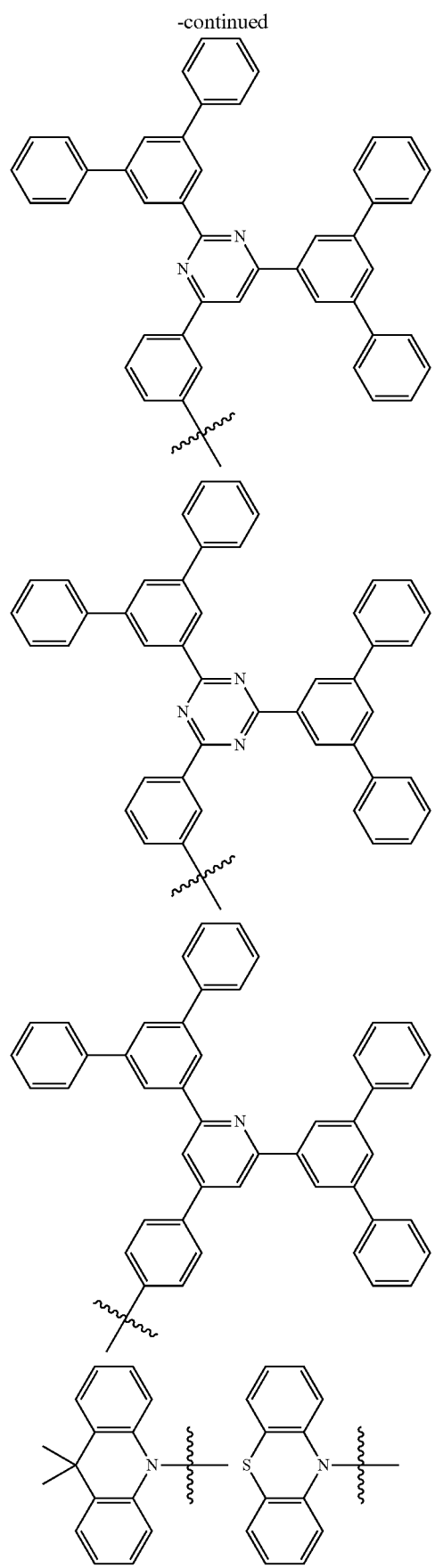

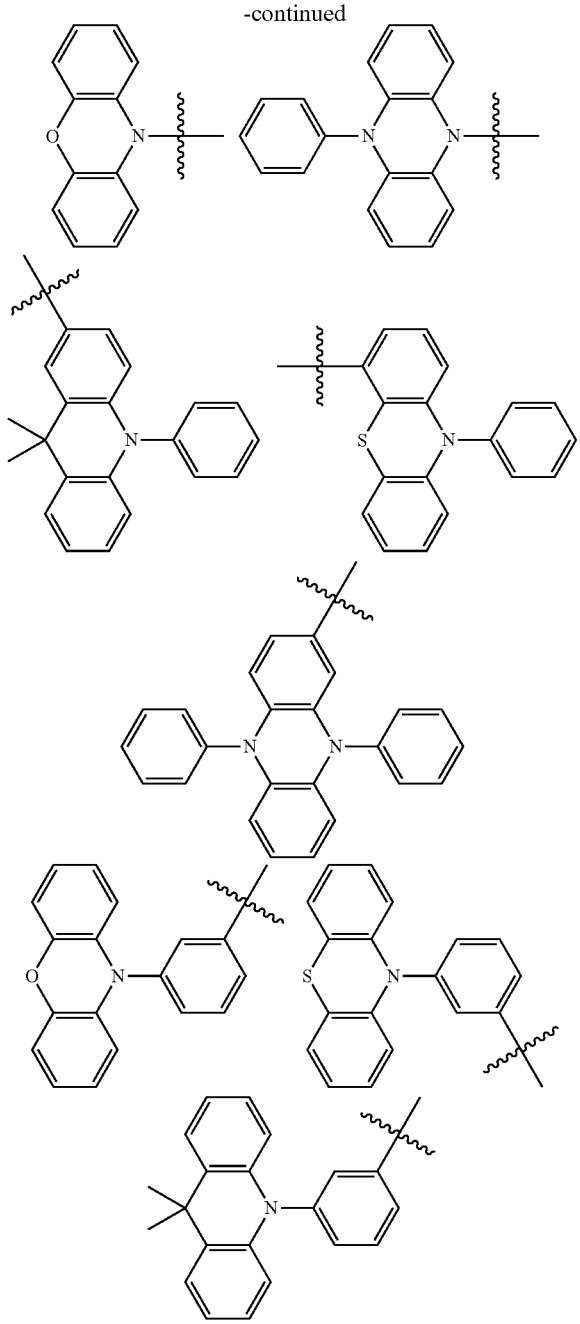

According to the above-mentioned the material formula (1) or formula (2) represented by the following formula (3) or formula (4):

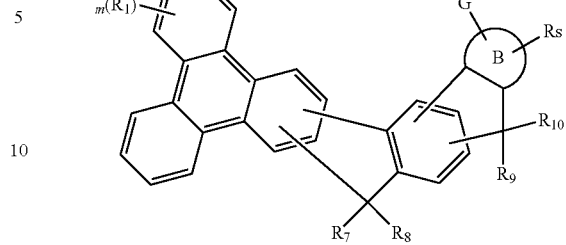

formula(3)

formula(4)

wherein B represents a fused ring hydrocarbon units with two or three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ and $R_7$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned the material formula (3) or formula (4) wherein the G is consisting of group represented as follows:

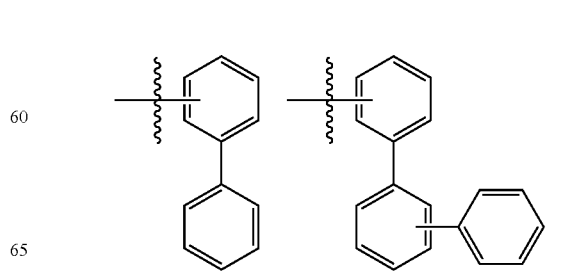

-continued
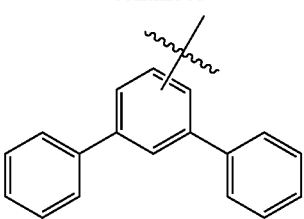
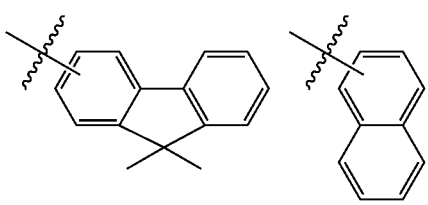
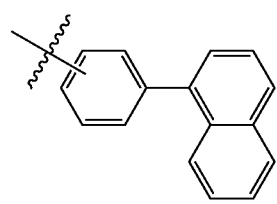
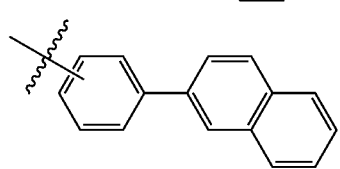
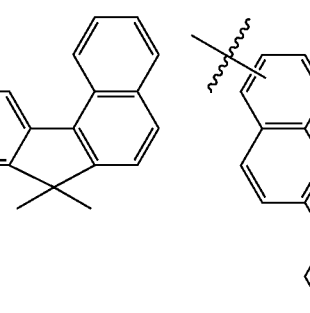
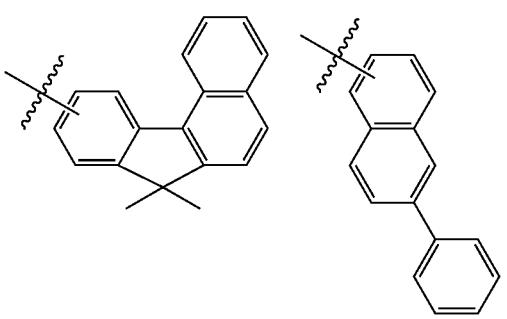
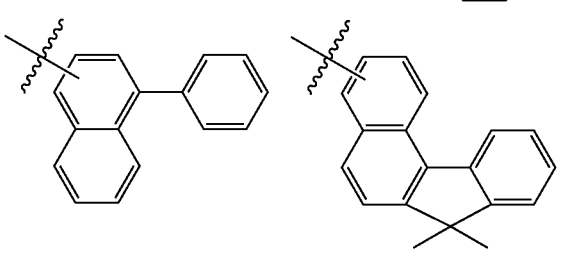
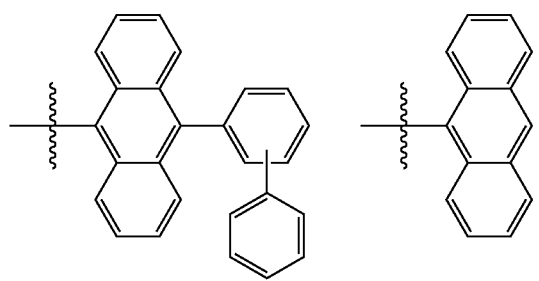
-continued
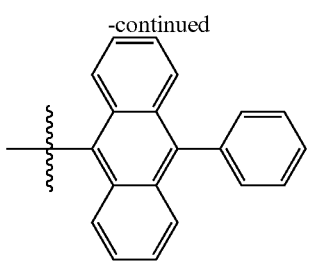
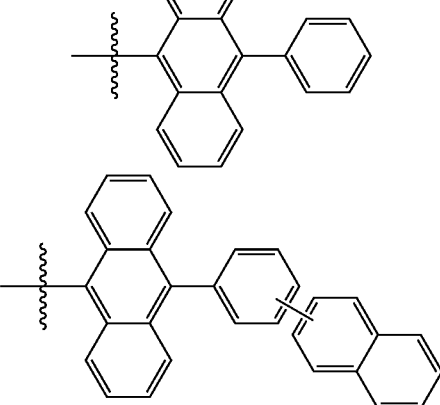
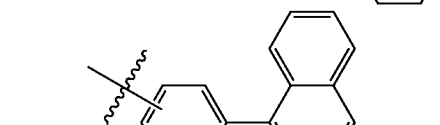
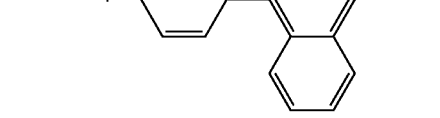
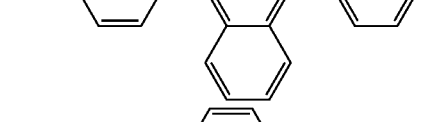
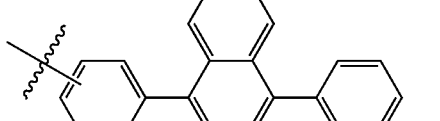
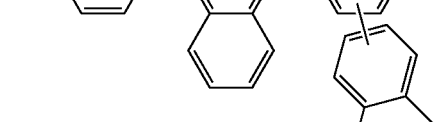
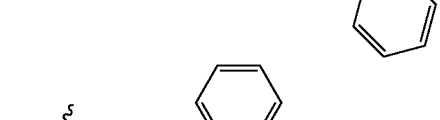
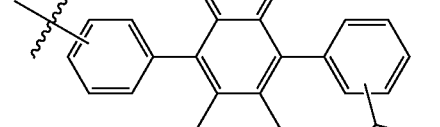
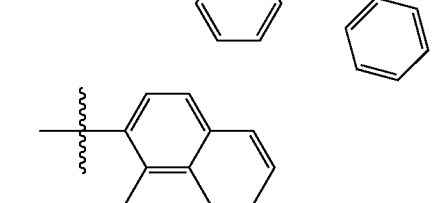
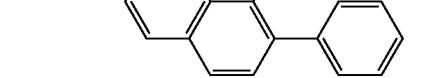

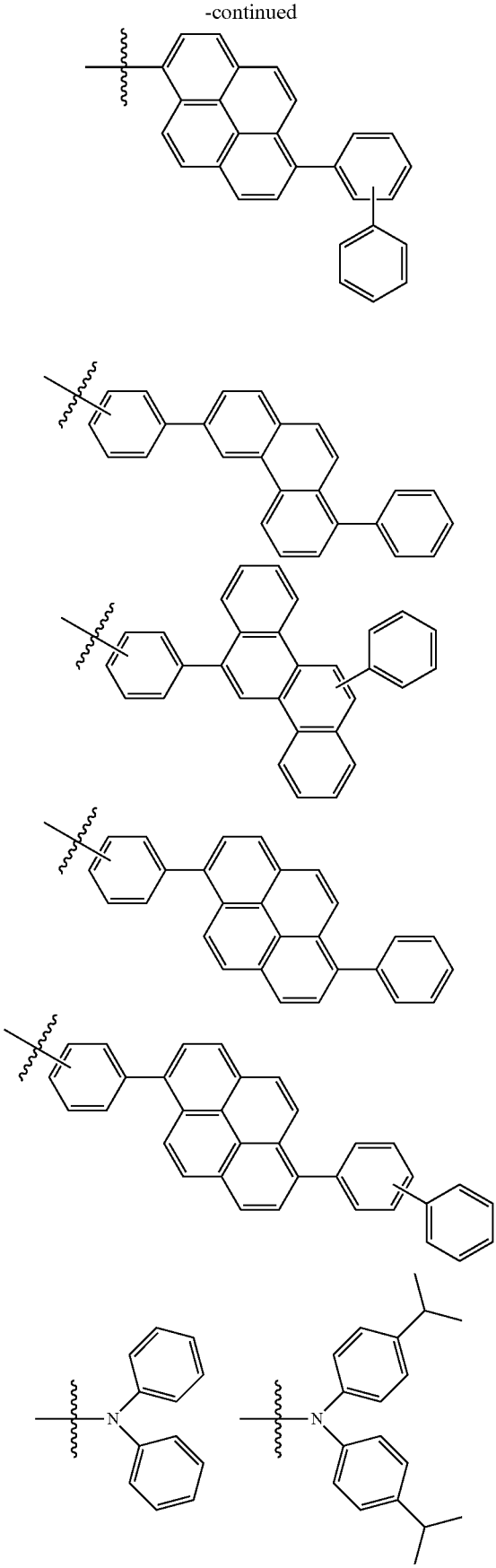

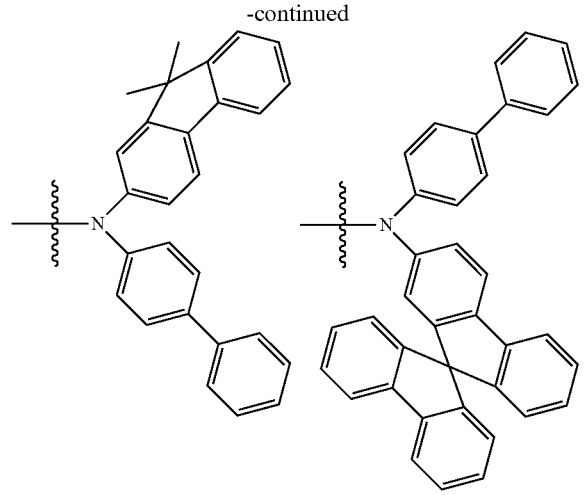
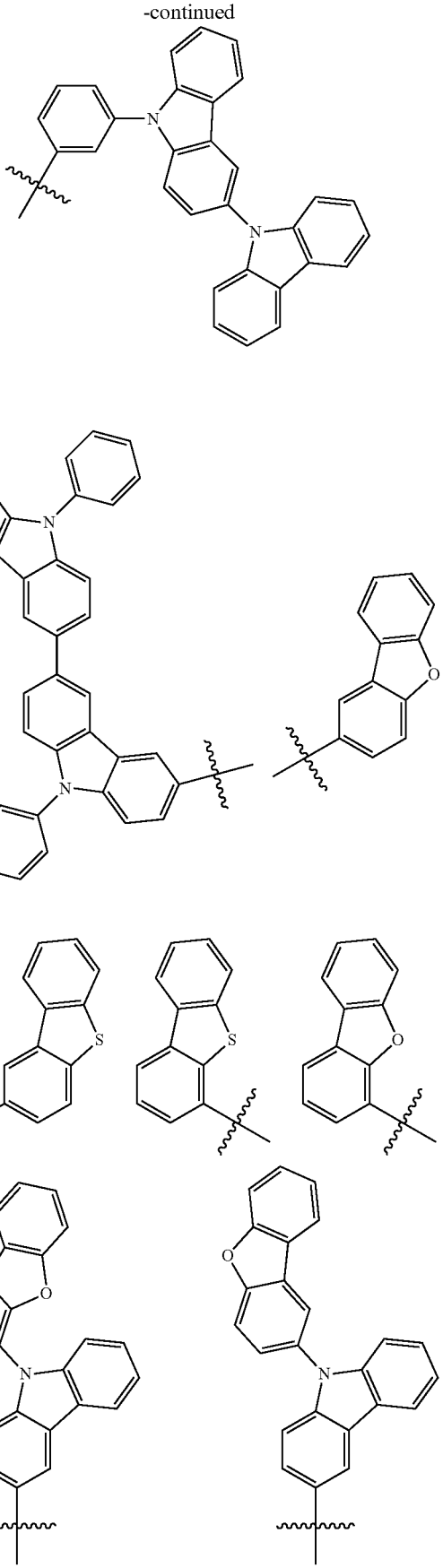

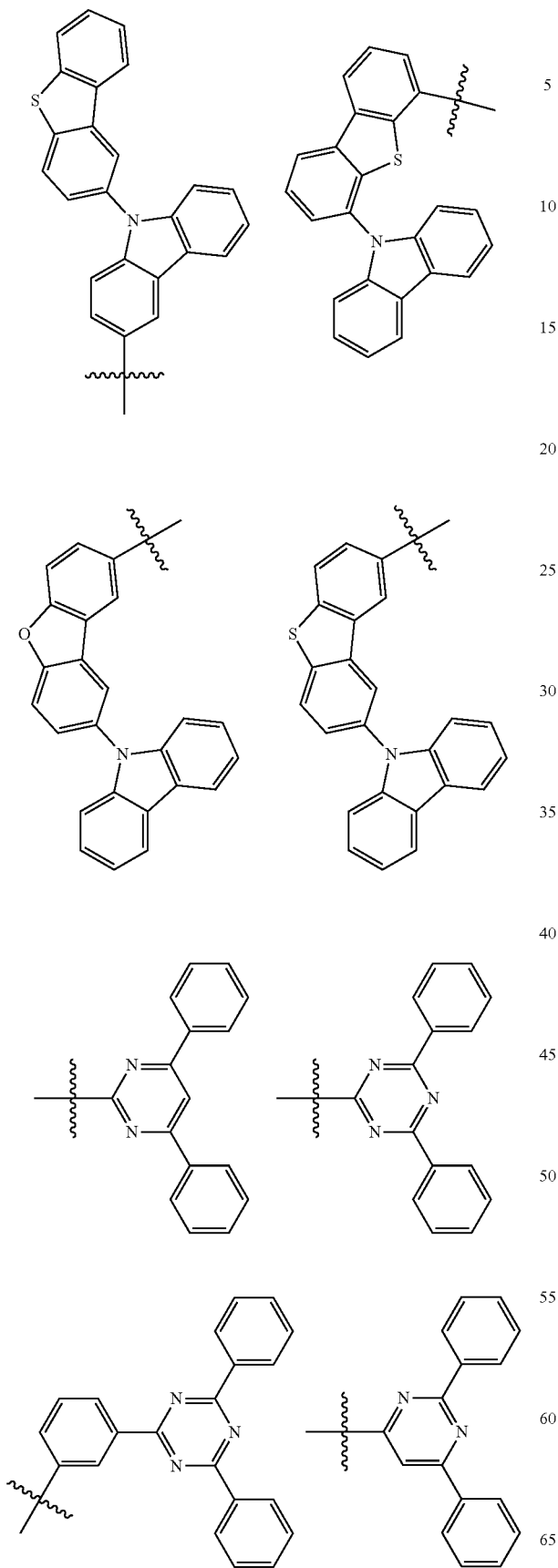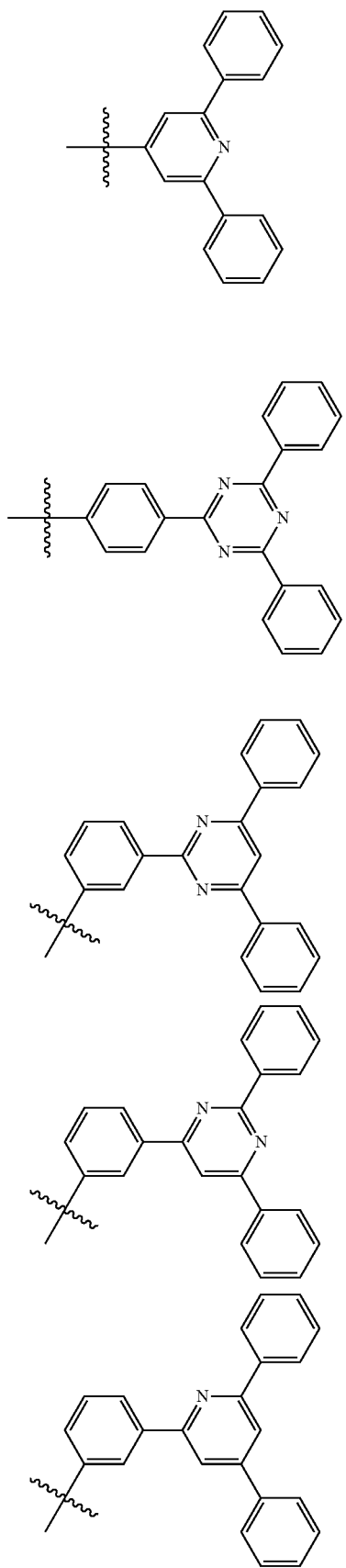

-continued
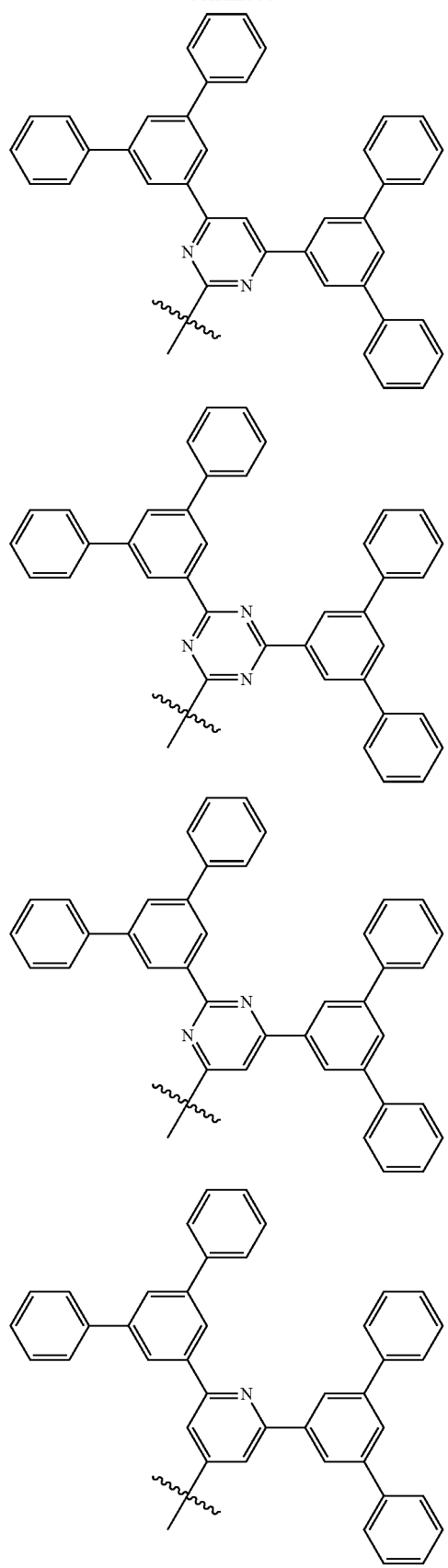
-continued
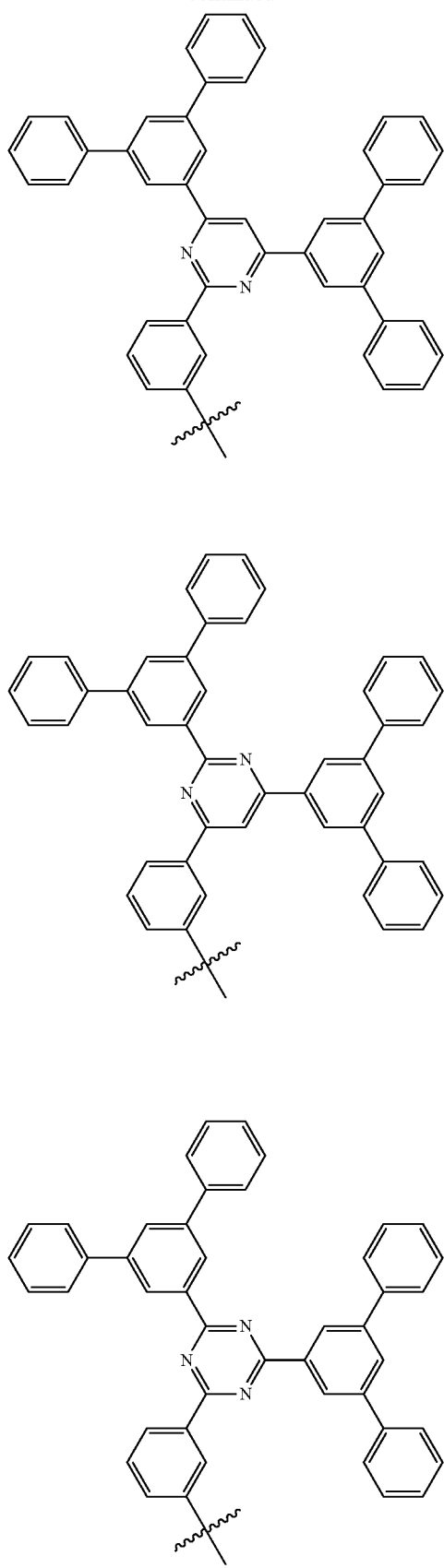

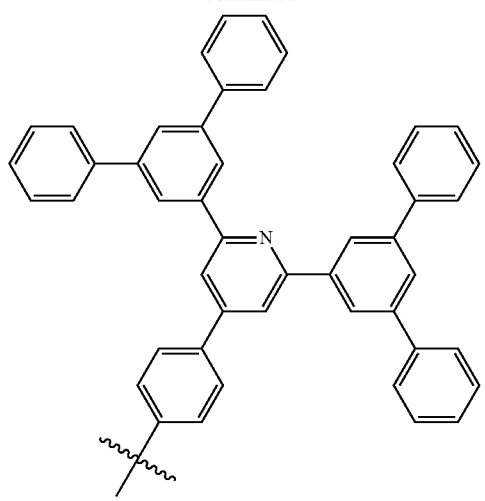
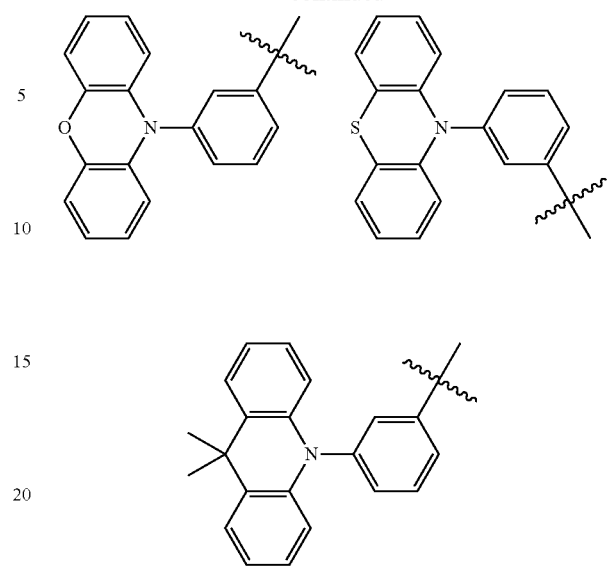
According to the above-mentioned the material formula (3) or formula (4) represented by the following formula (5) to formula (22):
formula (5)
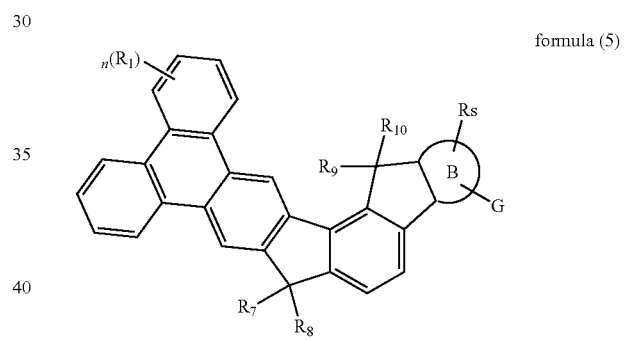
formula (6)
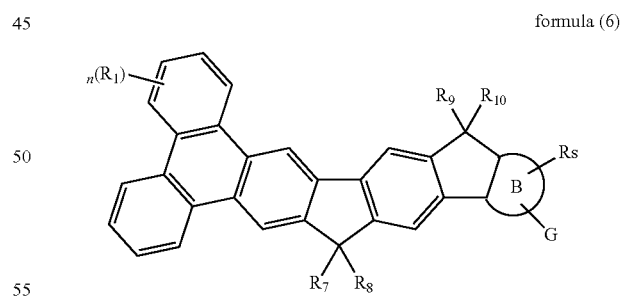
formula (7)
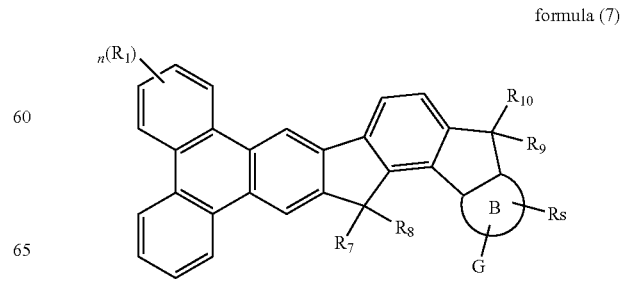

formula (8)
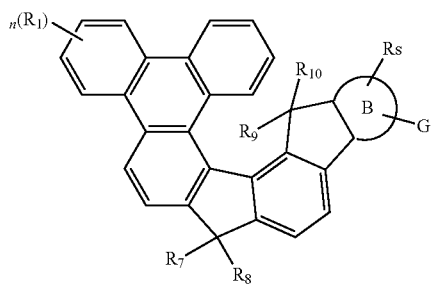
formula (9)
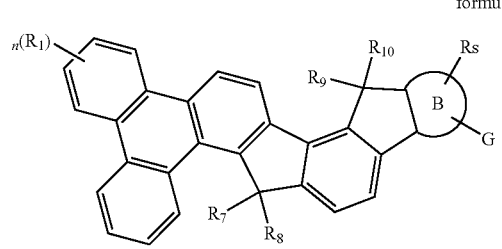
formula (10)
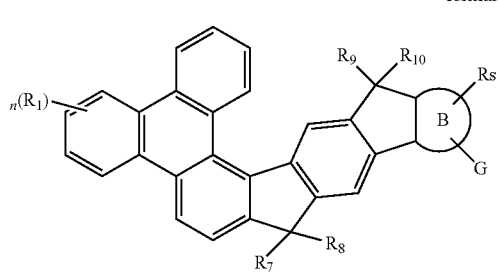
formula (11)
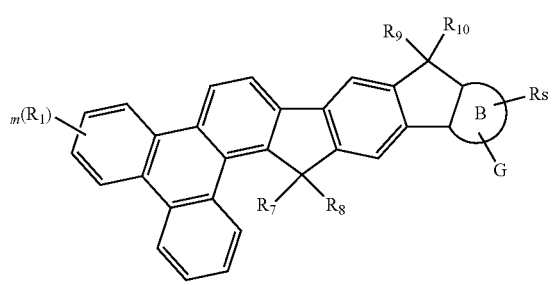
formula (12)
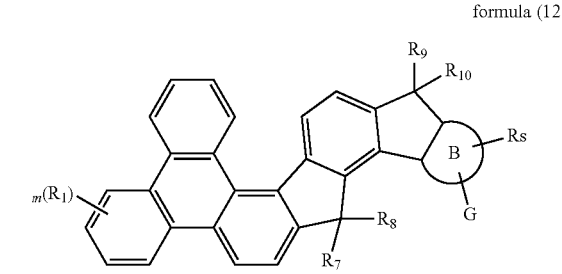
formula (13)
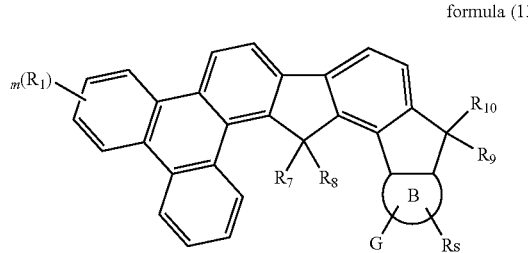
formula (14)
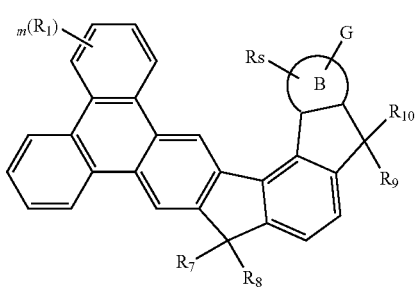
formula (15)
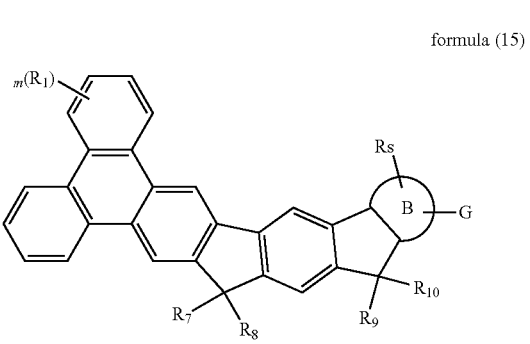
formula (16)
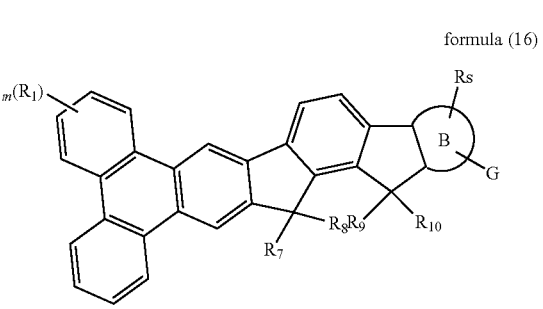
formula (17)
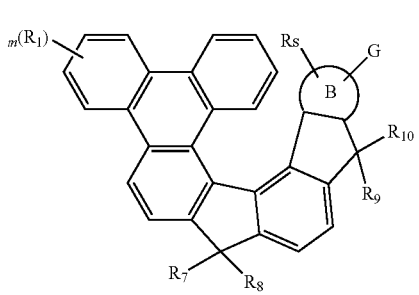
formula (18)
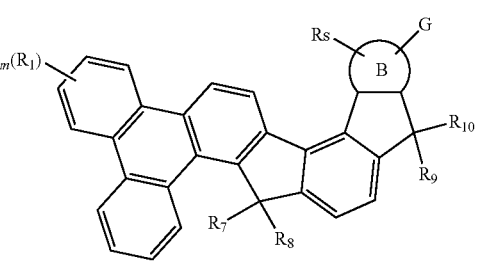

formula (19)

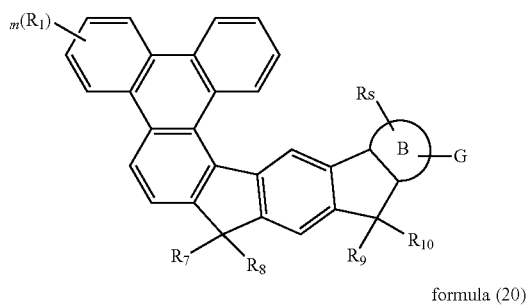

formula (20)

formula (21)

formula (22)

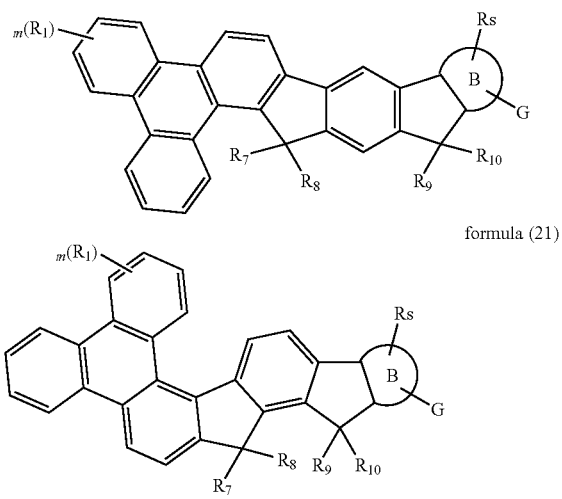

wherein B represents a fused ring hydrocarbon units with two or three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ and $R_7$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned the material formula (3) or formula (4) wherein the G is consisting of group represented as follows:

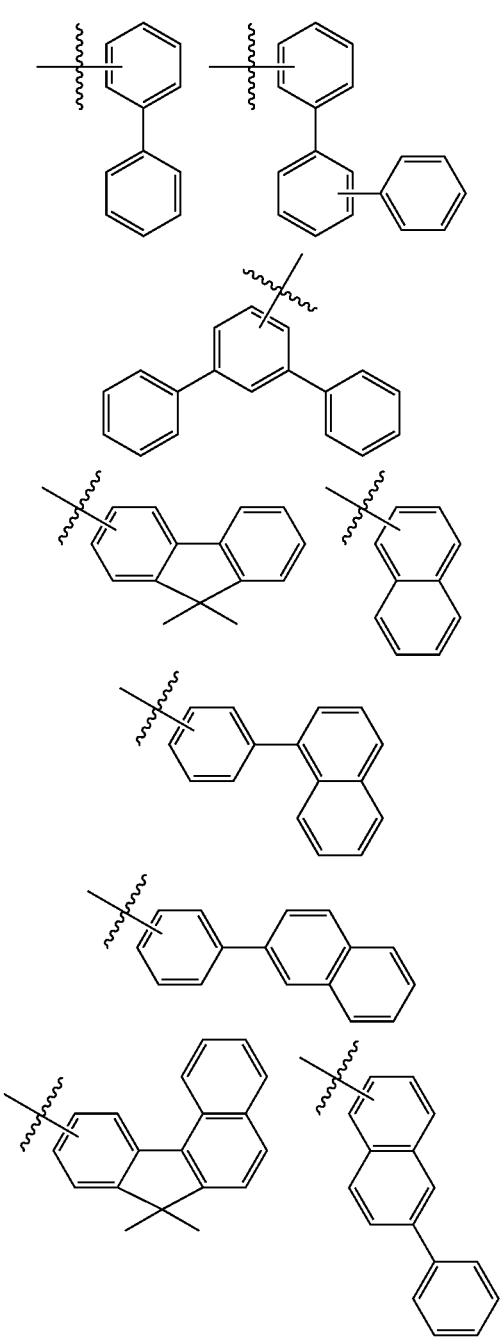

-continued
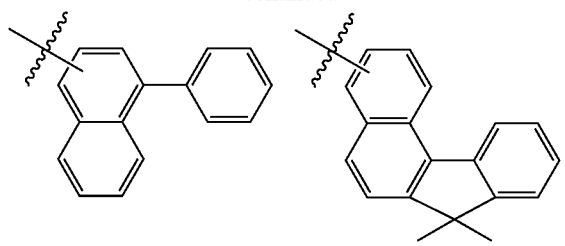
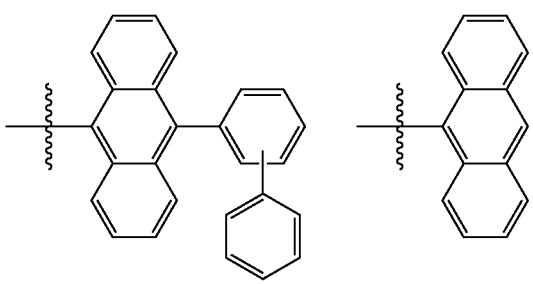
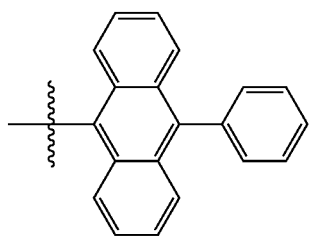
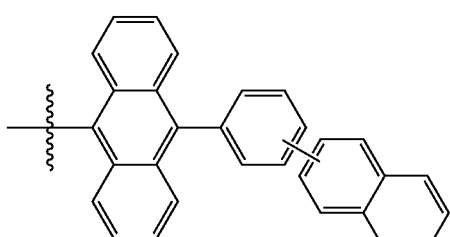
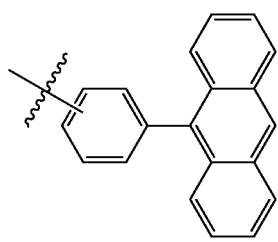
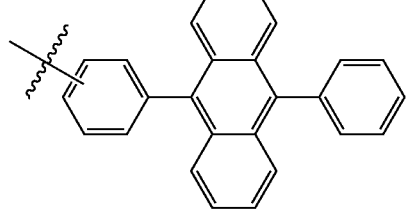
-continued
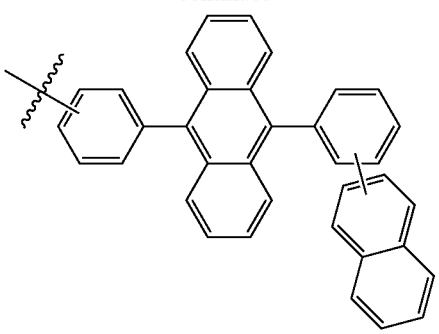
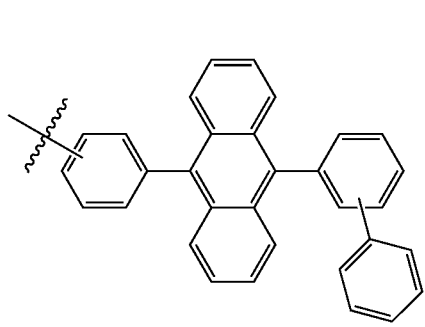
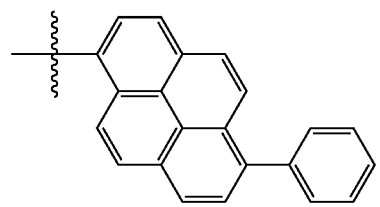
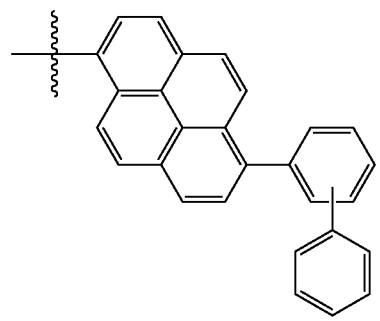
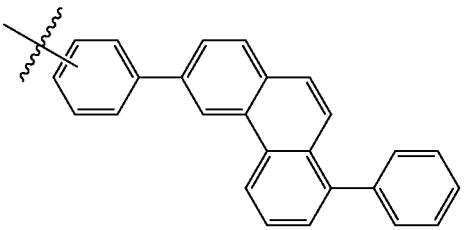
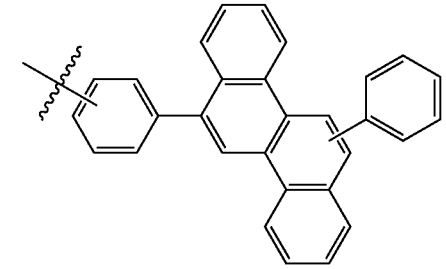

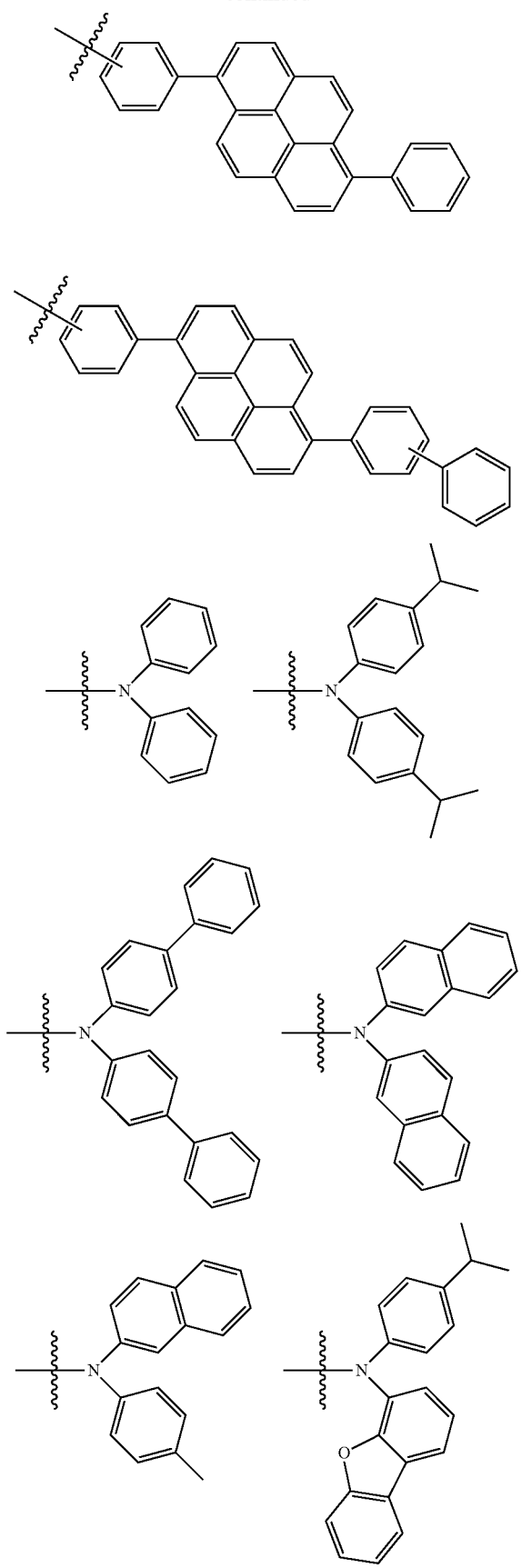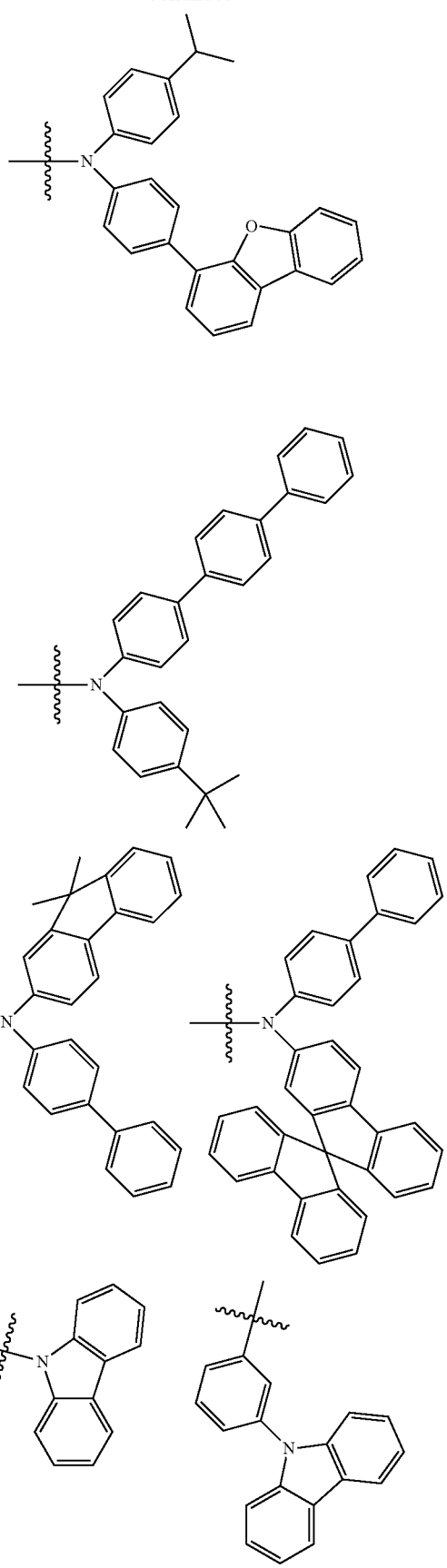

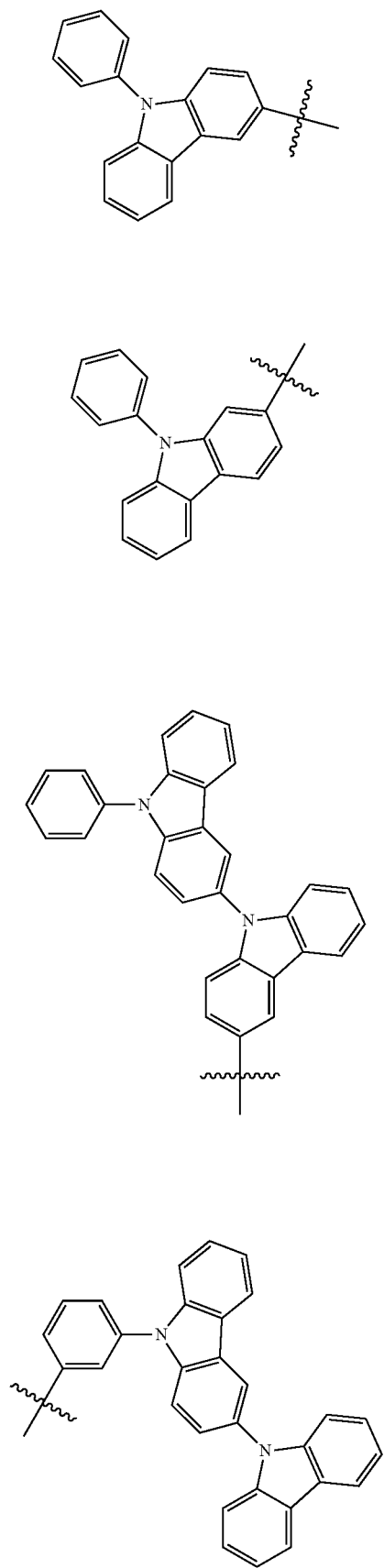
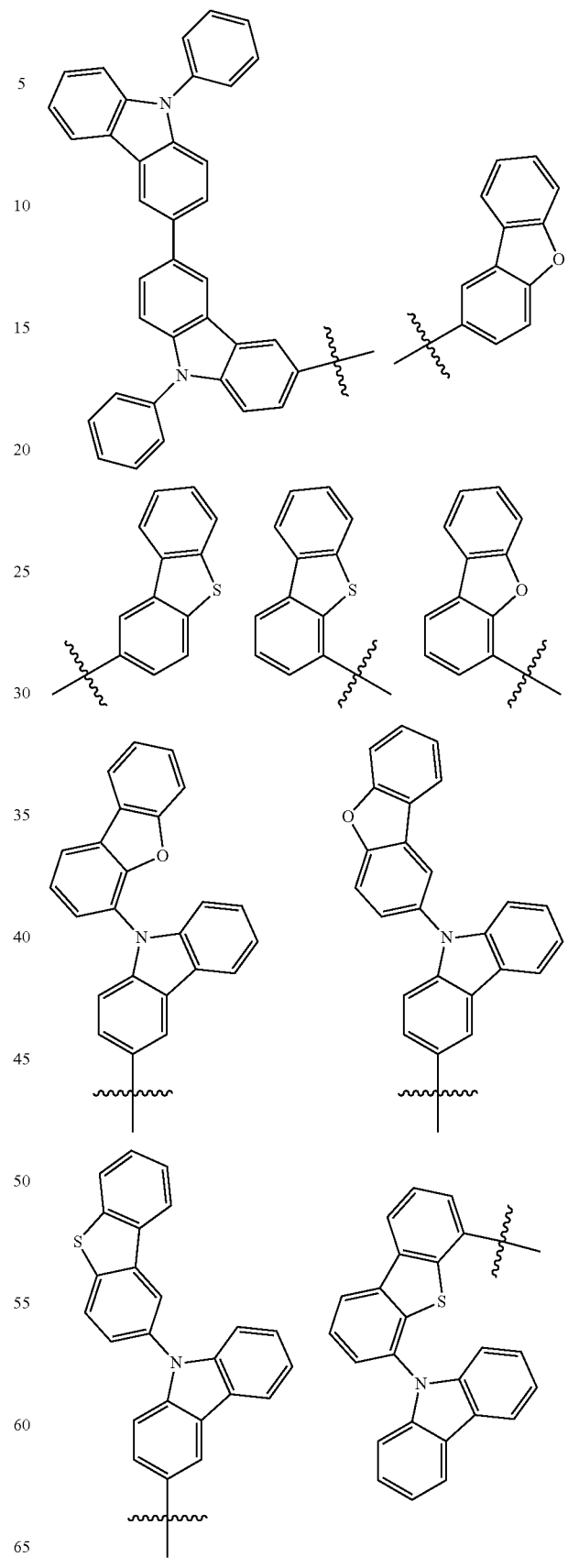

41
-continued
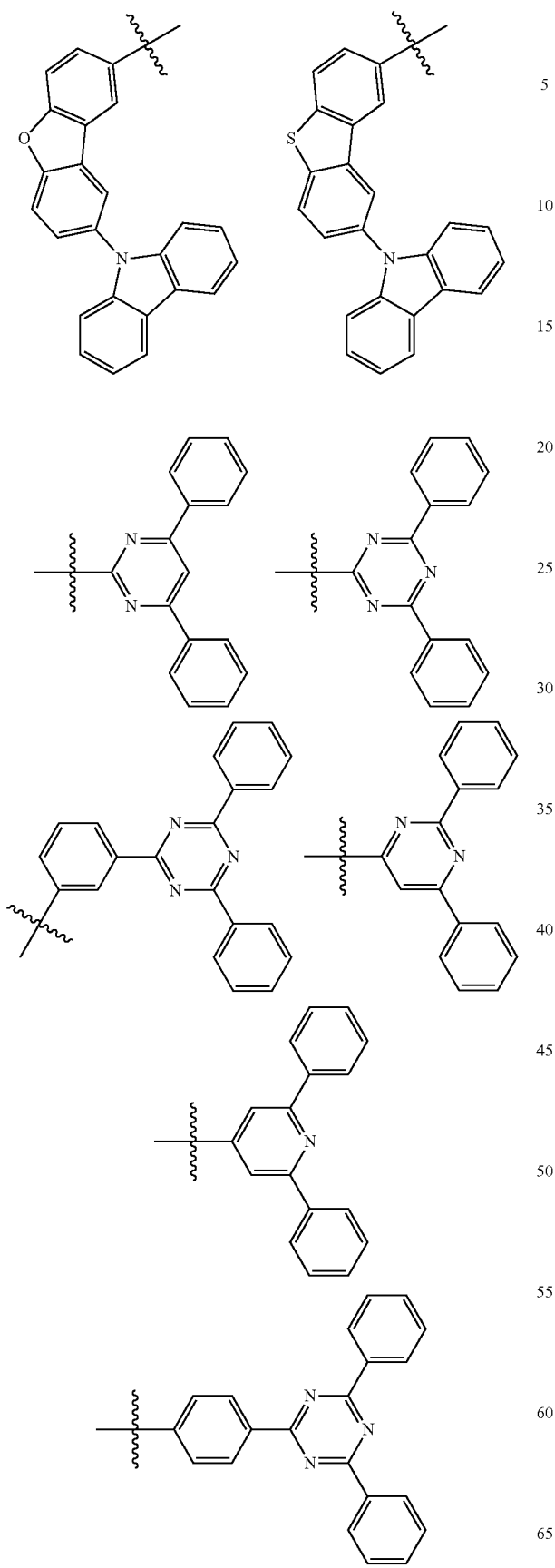
42
-continued
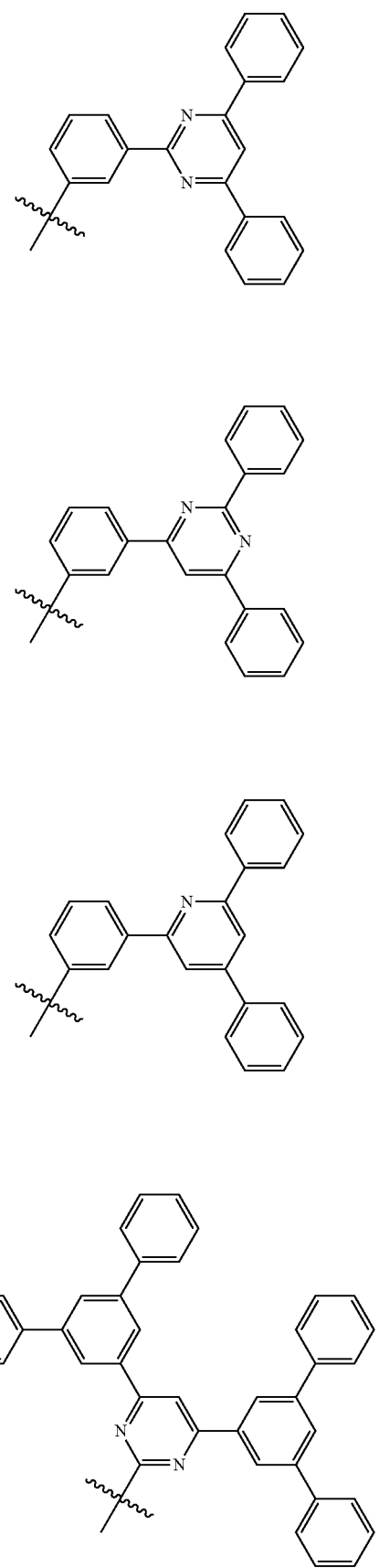

-continued
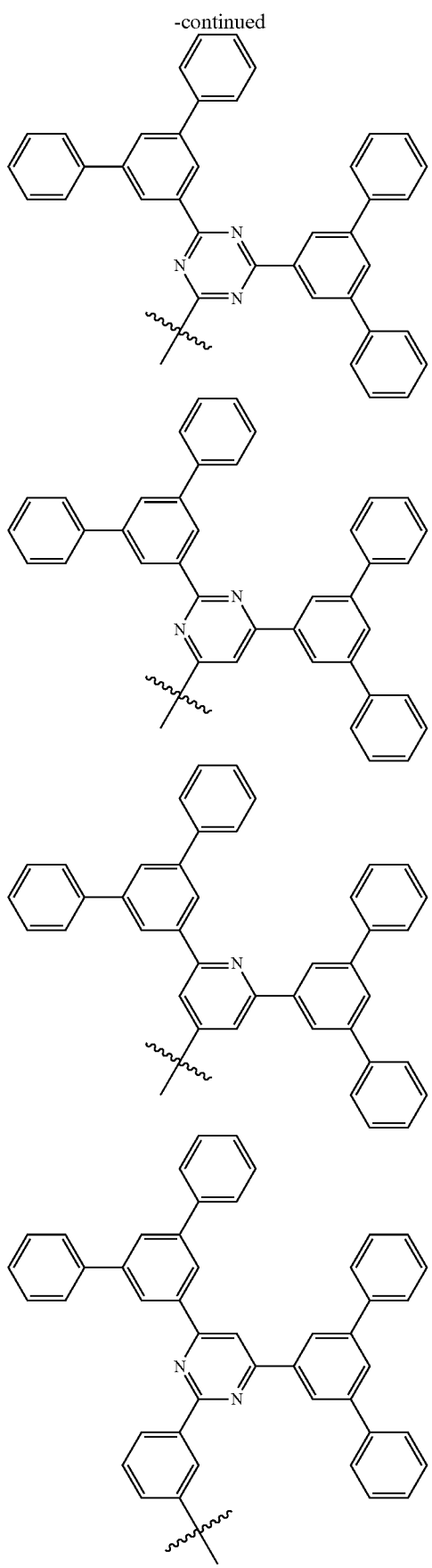
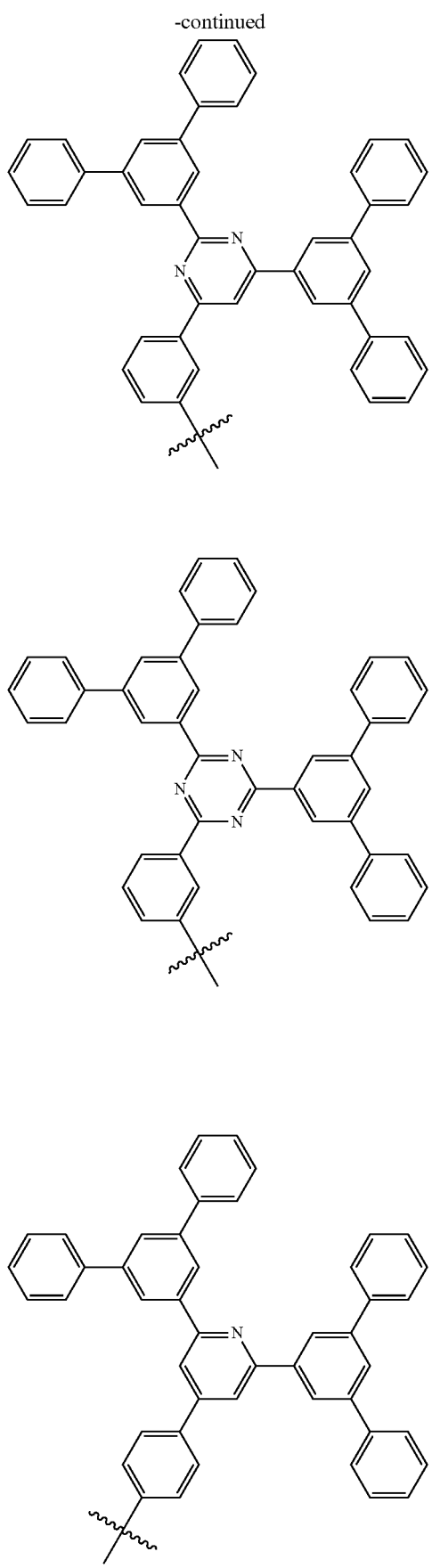

-continued
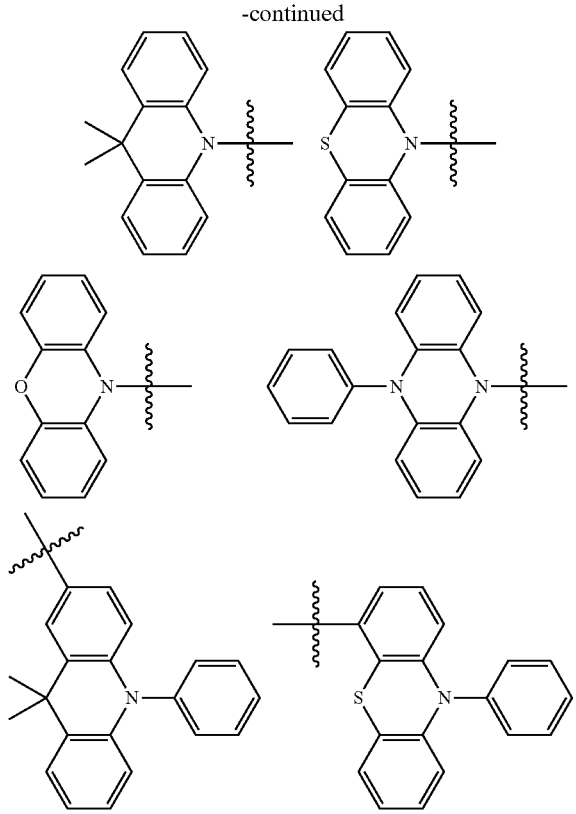
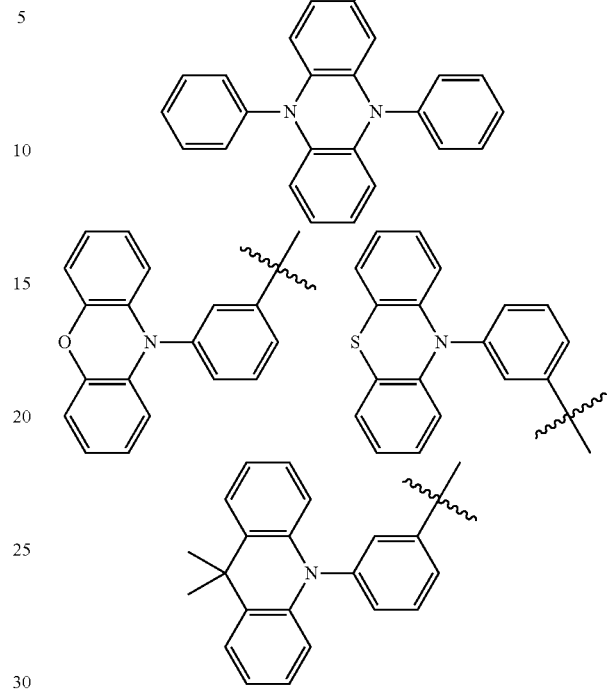
In this embodiment, some materials are shown below:
EX1
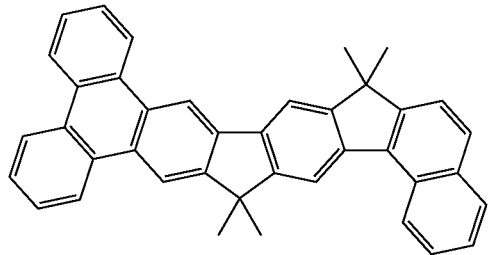
EX2
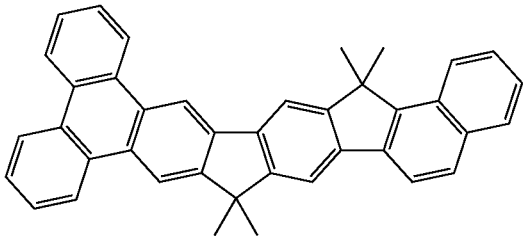
EX3
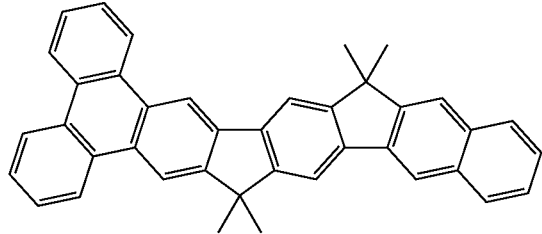
EX4
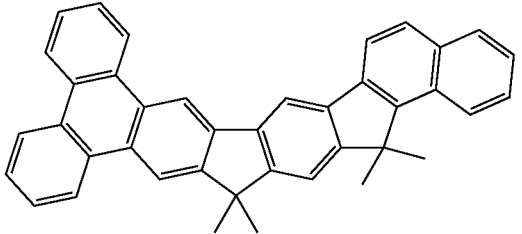
EX5
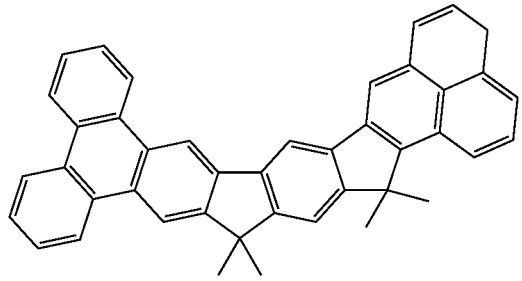
EX6
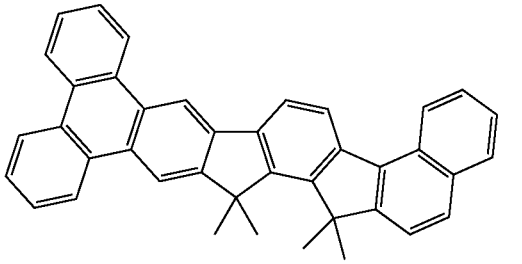

-continued
EX7
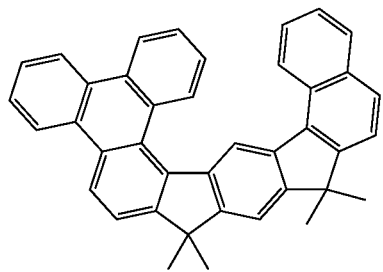
EX8
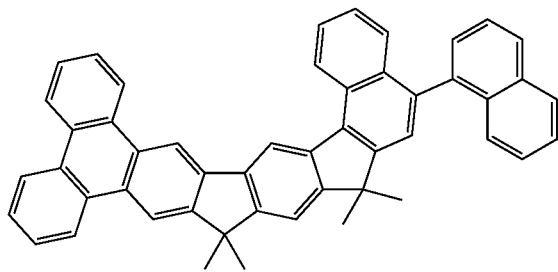
EX9
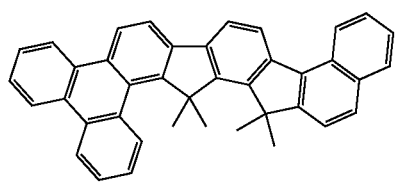
EX10
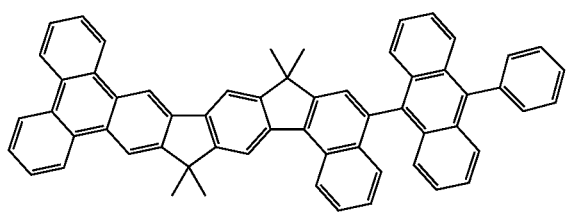
EX11
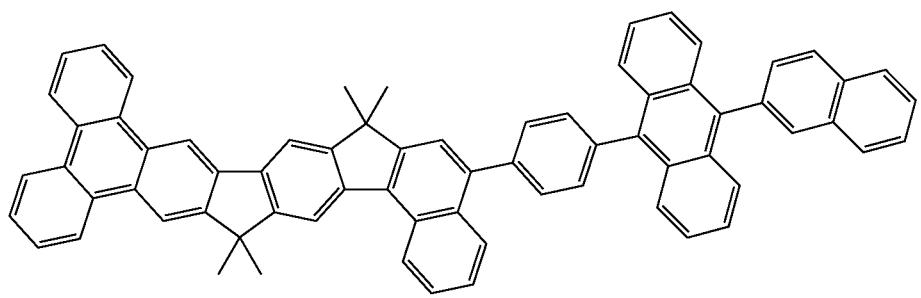
EX12
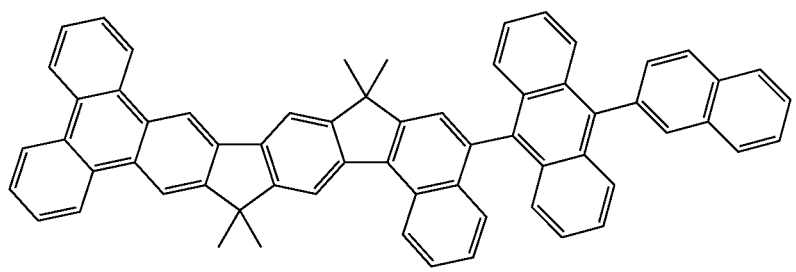
EX13
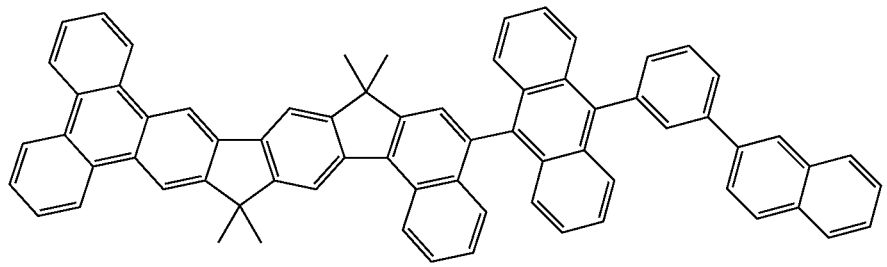

-continued
EX14
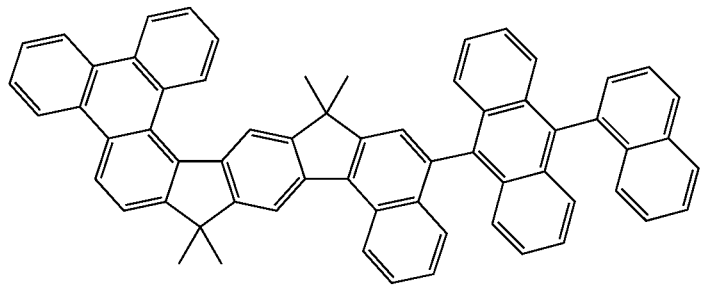
EX15
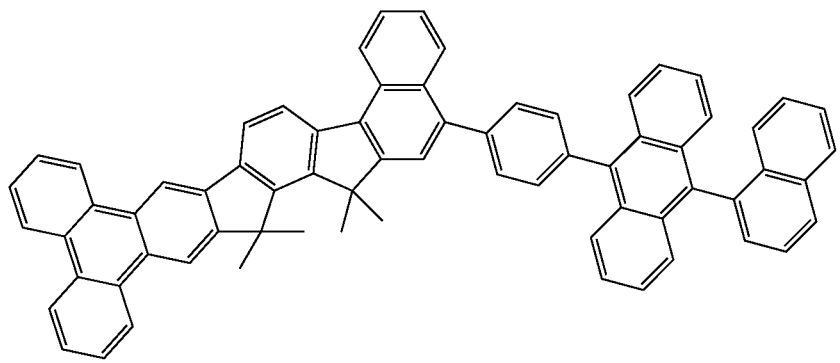
EX16
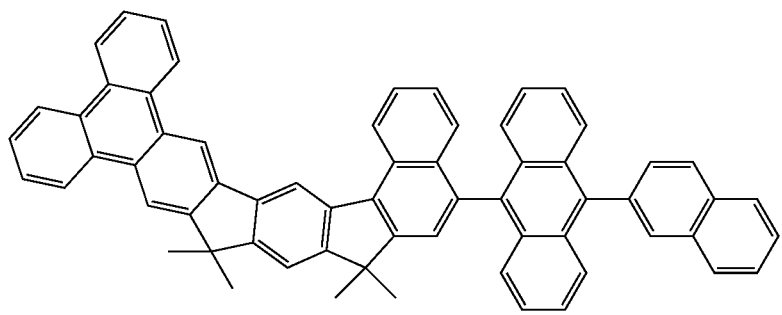
EX17
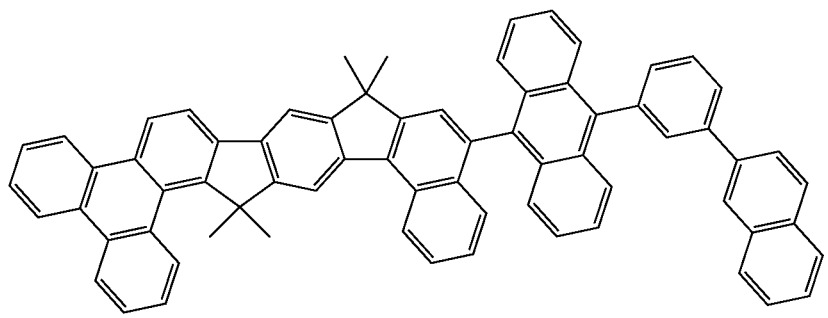

-continued
EX18
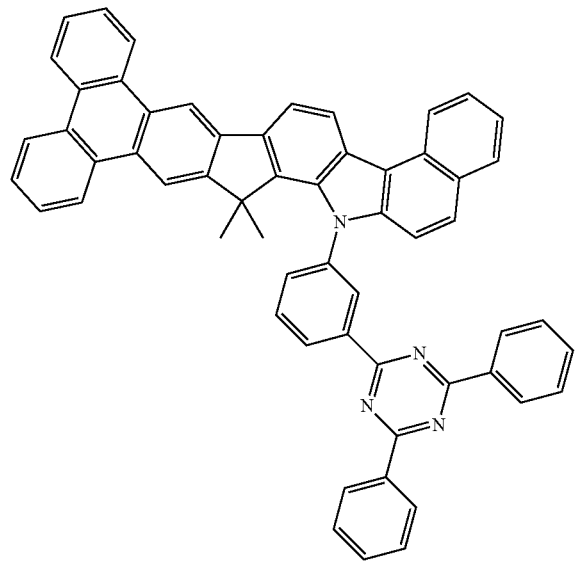
EX19
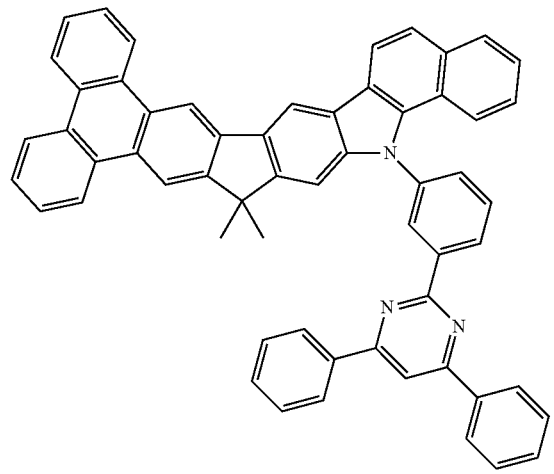
EX20
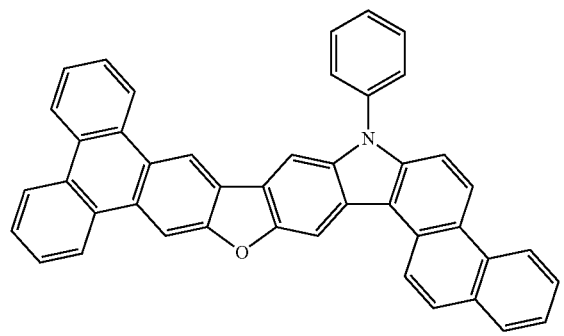
EX21
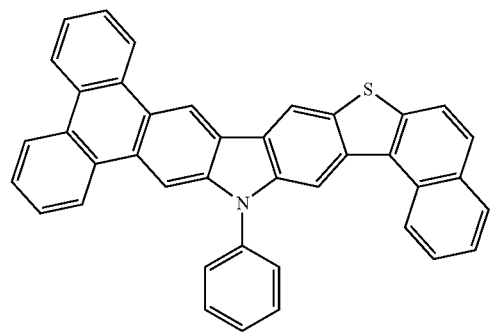
EX22
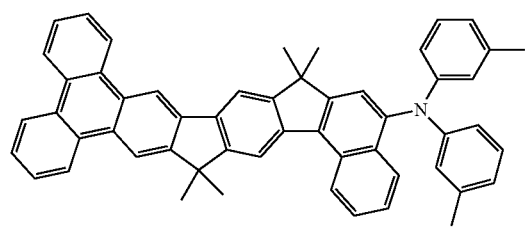
EX23
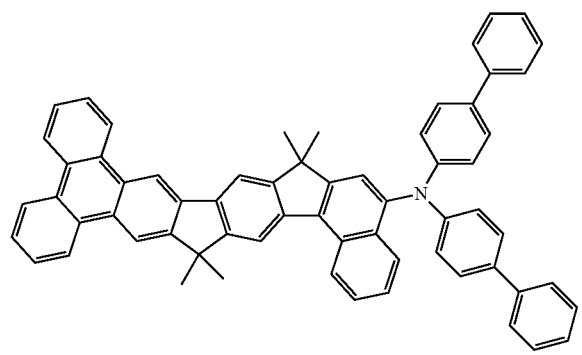

-continued
EX24 EX25
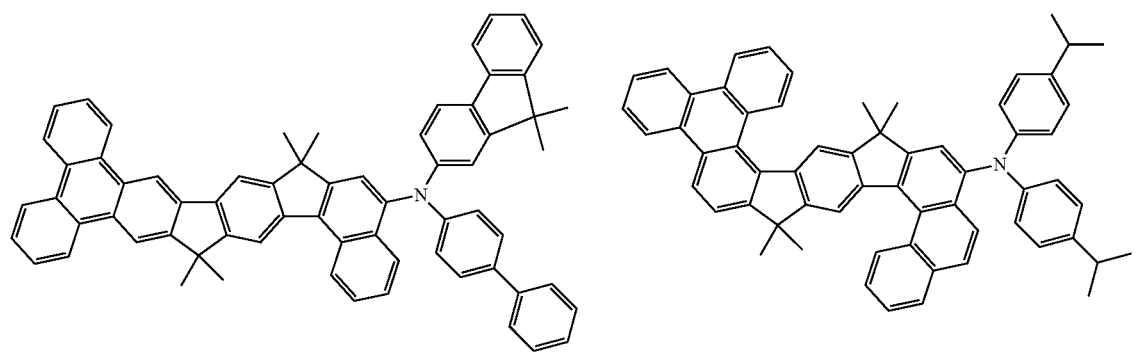
EX26
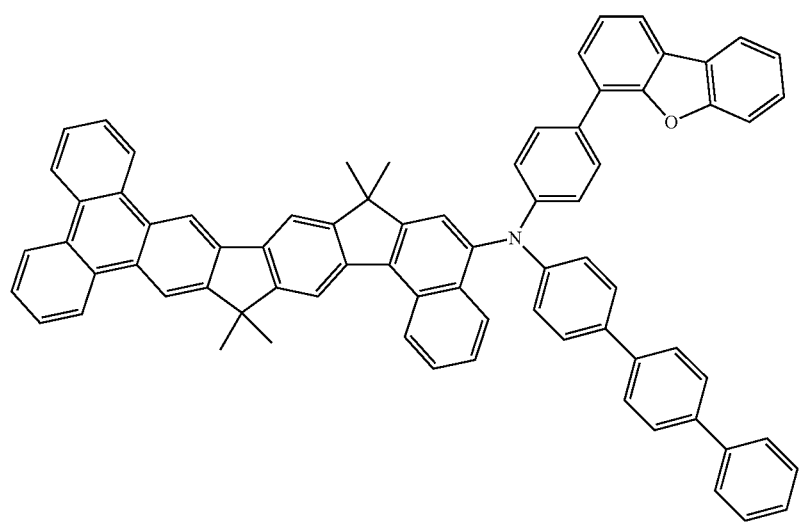
EX27 EX28
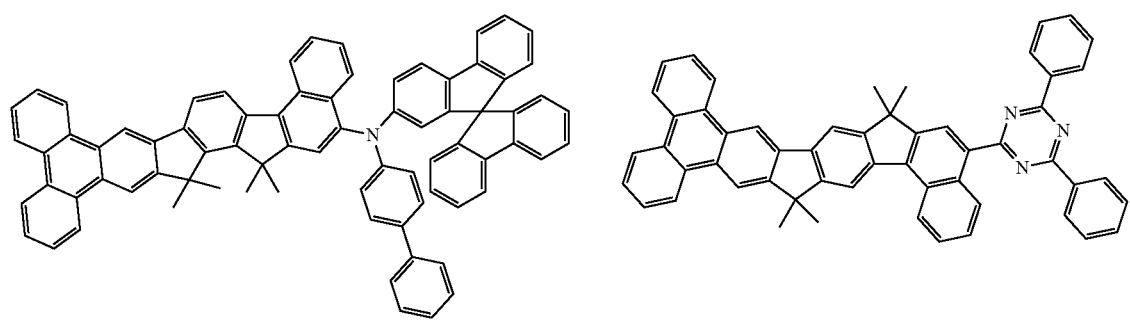
EX29
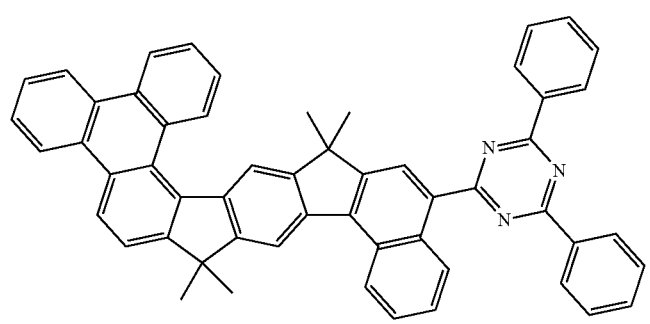

-continued
EX30
EX31
EX32
EX33
EX34
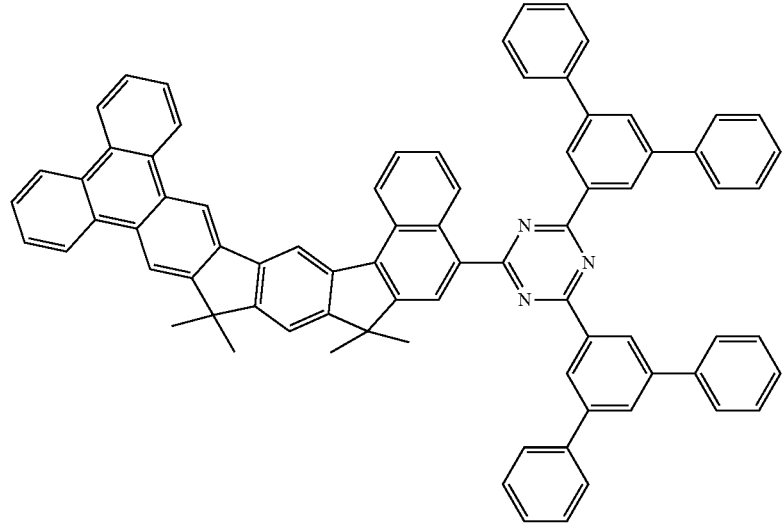

EX35
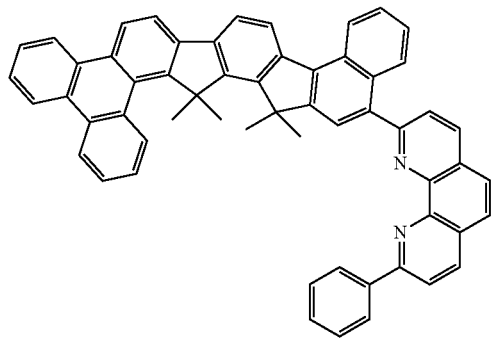

EX36
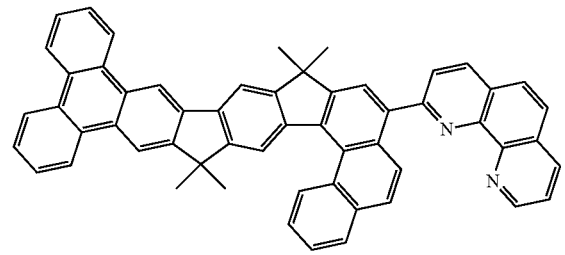

EX37
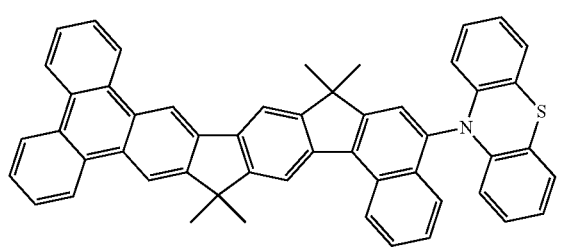

EX38
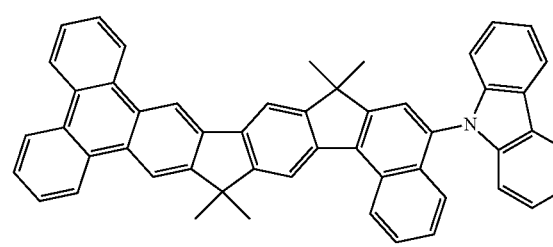

EX39
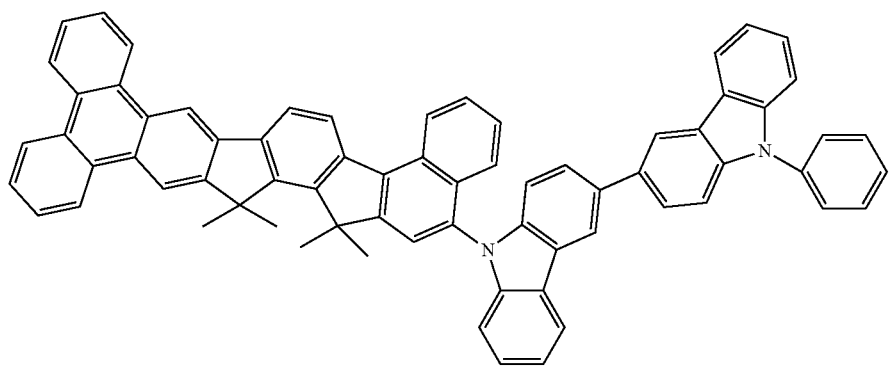

Detailed preparation for the material in the present invention could be clarified by exemplary embodiments, but the present invention is not limited to exemplary embodiments. EXAMPLE 1-5 show the preparation for some EXAMPLES of the material in the present invention. EXAMPLE 6-8 show the fabrication of organic EL device and I-V-B, half-life time of organic EL device testing report.

Example 1

Synthesis of EX10

Synthesis of 2-(4-bromo-2,5-dimethylphenyl)triphenylene

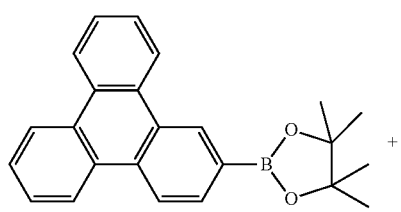 +

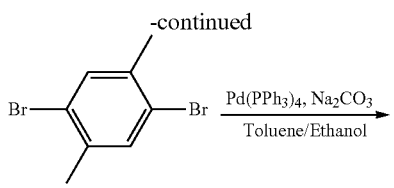

$\xrightarrow{\text{Pd(PPh}_3)_4,\ \text{Na}_2\text{CO}_3}{\text{Toluene/Ethanol}}$

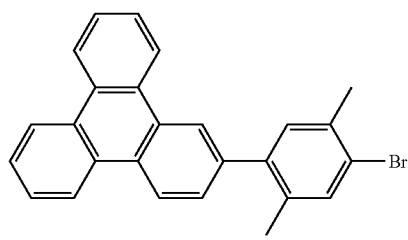

A mixture of 52.8 g (200 mmol) of 1,4-dibromo-2,5-dimethyl benzene, 70.9 g (200 mmol) of 4,4,5,5-tetramethyl-2-(triphenylen-2-yl)-1,3,2-dioxaborolane, 2.3 g (2 mmol) of tetrakis(triphenylphosphine)palladium, 400 ml of 2M Na$_2$CO$_3$, 400 ml of EtOH and 800 ml toluene was degassed and placed under nitrogen, and then heated at 90° C. for 12 hours. After the reaction finish, the mixture was allowed to cool to room temperature. The organic layer was extracted with ethyl acetate and water, dried with anhydrous magnesium sulfate, the solvent was removed and the residue was purified by column chromatography on silica gel (hexane-dichloromethane) to give product 60.1 g (146 mmol, 73%) as a white solid.

Synthesis of 2-(2,5-dimethyl-4-(naphthalen-1-yl)phenyl)triphenylene

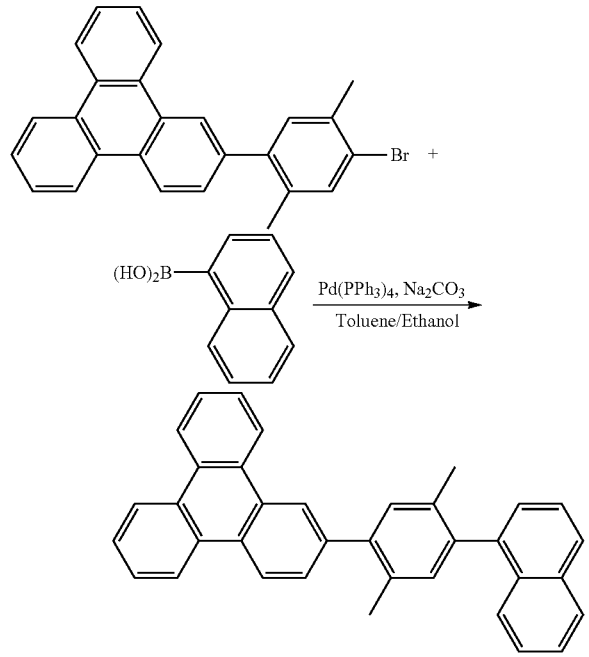

A mixture of 52.8 g (146 mmol) of 2-(4-bromo-2,5-dimethylphenyl) triphenylene, 30.1 g (175 mmol) of naphthalen-1-ylboronic acid, 1.15 g (1 mmol) of tetrakis(triphenylphosphine)palladium, 200 ml of 2M $Na_2CO_3$, 200 ml of EtOH and 400 ml toluene was degassed and placed under nitrogen, and then heated at 90° C. for 12 hours. After the reaction finish, the mixture was allowed to cool to room temperature. The organic layer was extracted with ethyl acetate and water, dried with anhydrous magnesium sulfate, the solvent was removed and the residue was purified by column chromatography on silica gel (hexane-dichloromethane) to give product 46.2 g (100.7 mmol, 69%) as a white solid.

Synthesis of 2-(naphthalen-1-yl)-5-(triphenylen-2-yl) terephthalic acid

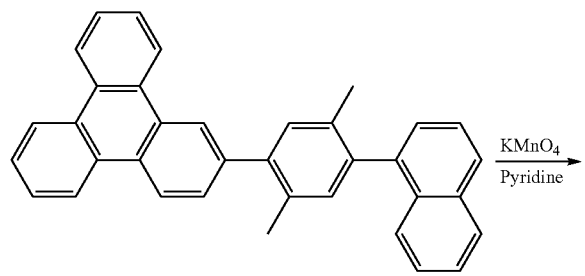

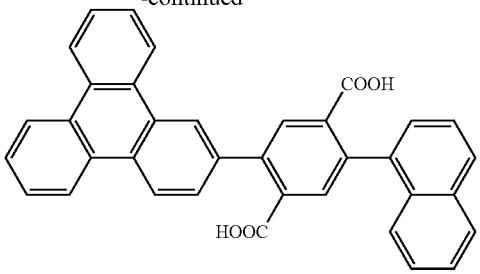

To a solution of 2-(2,5-dimethyl-4-(naphthalen-1-yl)phenyl) triphenylene 46.2 g (100.7 mmol) in pyridine (270 ml) was added to the hot $KMnO_4$ solution (145 g in 450 ml $H_2O$) over 1 h under reflux and the reaction was stirred at 130° C. for 12 h. After cooling to room temperature, the reaction was filtered and the residue was washed with hot $H_2O$ and ethyl acetate. The aqueous layer was acidified with 3 N HCl to pH-1 and the white suspension was extracted with ethyl acetate. After removal of solvent, a white solid was obtained which was suspended in $H_2O$ (400 ml) and treated with KOH (12 g). The solution was heated to 90° C. followed by addition of $KMnO_4$ solution (48 g in 240 ml $H_2O$) over 1 h. This solution was stirred for another 8 hours. After cooling to room temperature, MeOH was added and the reaction was stirred till the purple color disappeared. The mixture was filtered. Removal of filtrate afforded a white solid which was treated with 3 NHCl to pH-1. The resultant slurry was extracted with ethyl acetate. The combined organic layer was washed with brine and dried over anhydrous magnesium sulfate. After removal of solvent a white solid was obtained as the 2-(naphthalen-1-yl)-5-(triphenylen-2-yl)terephthalic acid 20.4 g (39.3 mmol, 39%).

Synthesis of Intermediate I

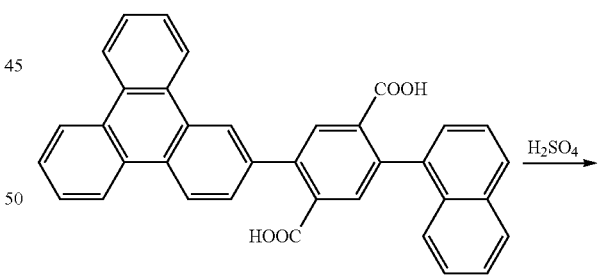

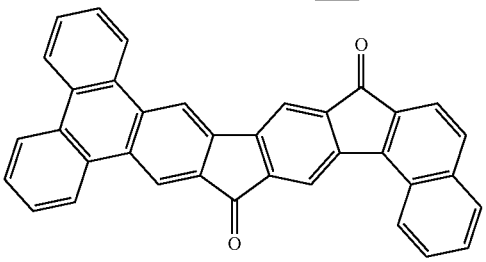

intermediate I

A mixture of 2-(naphthalen-1-yl)-5-(triphenylen-2-yl) terephthalic acid 20.4 g (39.3 mmol), 130 ml of sulfuric acid was placed under nitrogen, and then heated to 80° C. for 1 hour. After the reaction finish, the mixture was allowed to cool to room temperature. The reaction mixture was poured on ice, the separated precipitate was filtered off, washed with water, and dried in air at room temperature to give product 12.9 g (30 mmol, 76%) as a yellow solid.

Synthesis of Intermediate II

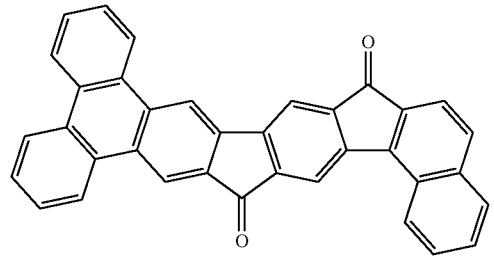

intermediate I

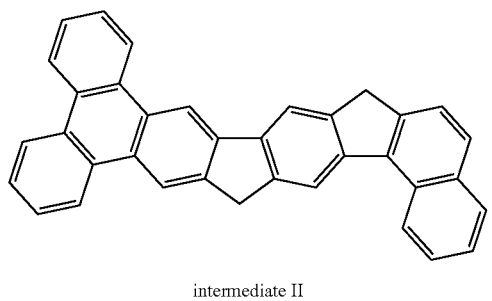

intermediate II

A mixture of 12.9 g (30 mmol) of intermediate I, 9 g (300 mmol) of hydrazine monohydrate in 180 ml of diethylene glycol was stirred at 80° C. for 3 hours and then refluxed for 1 hour. The resulting mixture was cooled to room temperature, treated with a solution of 16.5 g (295 mmol) of KOH in 50 ml of water, and refluxed for 3 hours. The resulting mixture was poured into 400 ml of water, and the precipitate was filtered off, washed with water, and dried in air at room temperature to give product 11.7 g (25.8 mmol, 86%) as a yellow solid.

Synthesis of Intermediate III

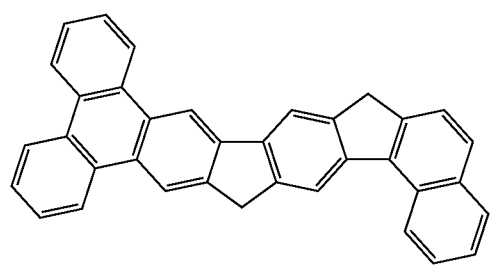

intermediate II

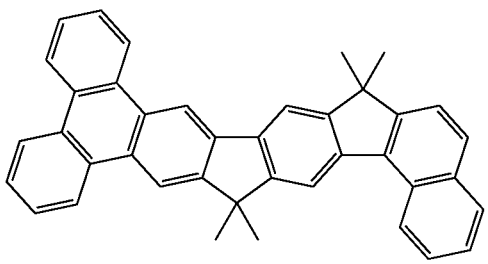

intermediate III

To a solution of intermediate II 11.7 g (25.8 mmol) and potassium iodide 2.15 g (13 mmol) in DMSO (250 ml) were added iodomethane 77 g (542 mmol) and potassium hydroxide 30.5 g (542 mmol). The reaction mixture was stirred at room temperature for 24 hours. The organic layer was separated and the aqueous layer extracted with ethyl acetate and water, dried with anhydrous magnesium sulfate, the solvent was removed and the residue was purified by column chromatography on silica gel (hexane-dichloromethane) to give product 8.8 g (17.3 mmol, 67%) as a yellow solid.

Synthesis of Intermediate IV

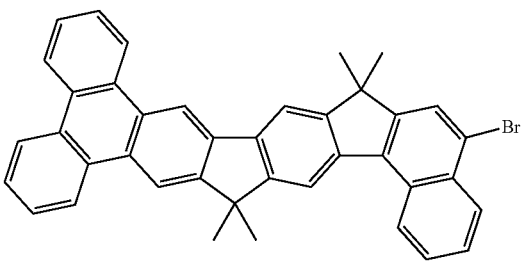

intermediate III intermediate IV

Intermediate III 8.8 g (17.3 mmol) was dissolved in 100 ml chloroform, protected from light and bromine 3 g (19 mmol) diluted in 30 ml chloroform was added dropwise at 0° C. The reaction was stirred at room temperature for 24 h, after which water (600 ml) was added. The crude product precipitated, this was filtered off and recrystallized from chloroform and methanol to give the pure product 7.9 g (13.5 mmol, 78%) as yellow solid. chemical shift (ppm) 9.38 (s, 1H), 9.07 (d, J=8.0 Hz, 1H), 8.92-8.85 (m, 3H), 8.77-8.61 (m, 5H), 8.22-8.11 (m, 2H), 7.91-7.63 (m, 5H), 1.69 (m, 12H).

Synthesis of Intermediate V

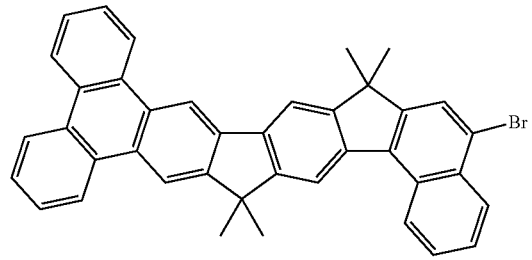

intermediate IV

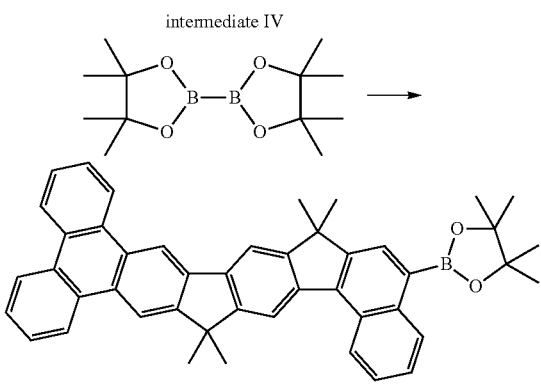

intermediate V

A mixture of 7.9 g (13.5 mmol) of intermediate IV, 4.1 g (16.2 mmol) of bis(pinacolato)diboron, 0.36 g (0.31 mmol) of tetrakis(triphenylphosphine) palladium, 4 g (40.56 mmol) of potassium acetate, and 200 ml of 1,4-dioxane was degassed and placed under nitrogen, and then heated at 120° C. for 24 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 5.1 g of light yellow product (yield 59%).

Synthesis of EX10

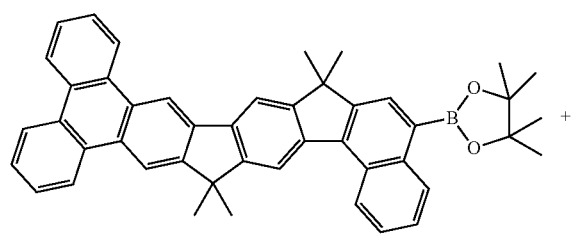

intermediate V

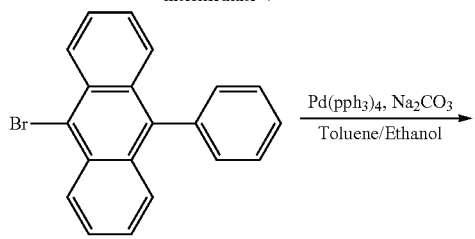

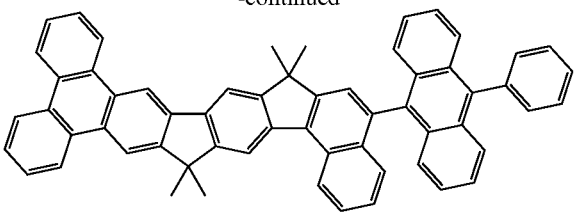

A mixture of 2.4 g (3.8 mmol) of intermediate V, 1.4 g (4.2 mmol) of 9-bromo-10-phenylanthracene, 0.11 g (0.1 mmol) of tetrakis(triphenyl phosphine)palladium, 5 ml of 2M $Na_2CO_3$, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was purified by column chromatography on silica (Hx-DCM) to give product 1.6 g (57%). MS (m/z, $FAB^+$): 762.5

Example 2

Synthesis of EX22

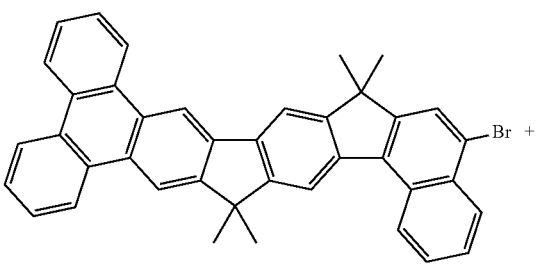

intermediate IV

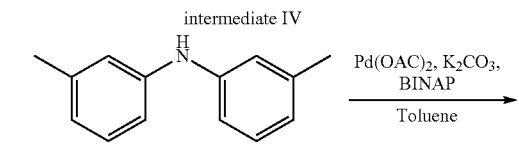

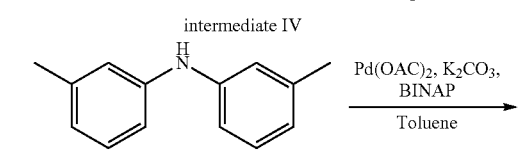

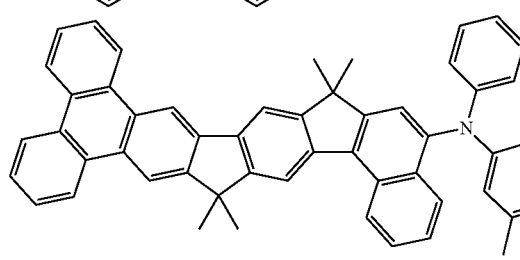

A mixture of 3.5 g (6 mmol) of intermediate IV, 1.2 g (6 mmol) of, dim-tolylamine 0.1 g (0.4 mmol) of palladium (II)acetate, 0.48 g of BINAP, 4 g of potassium carbonate and 50 ml toluene was degassed and placed under nitrogen, and then heated at 110° C. overnight. After finishing the reaction, the mixture was allowed to cool to room temperature. Than 200 ml of MeOH was added, while stirring and the precipitated product was filtered off with suction. To give 1.6 g (yield 38%) of yellow product which was recrystallized from ethyl acetate. MS (m/z, $FAB^+$): 705.6

Example 3

Synthesis of EX28

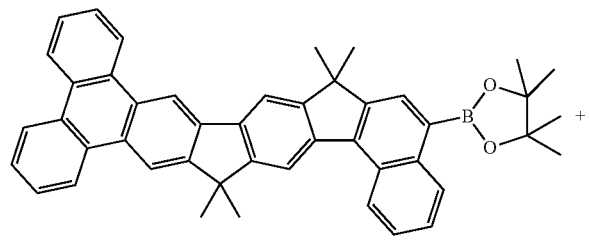
intermediate V

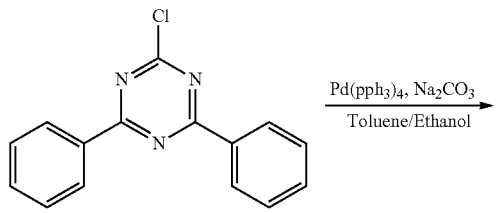

Pd(pph₃)₄, Na₂CO₃
Toluene/Ethanol

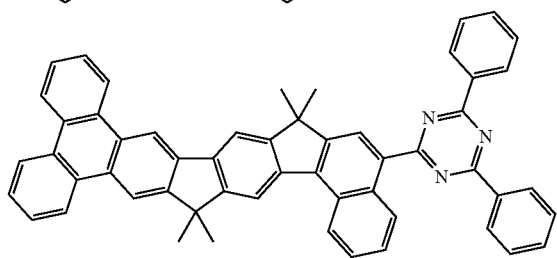

A mixture of 2.4 g (3.8 mmol) of intermediate V, 1.1 g (4.2 mmol) of 2-chloro-4,6-diphenyl-1,3,5-triazine, 0.11 g (0.1 mmol) of tetrakis(triphenyl phosphine)palladium, 5 ml of 2M Na₂CO₃, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was purified by column chromatography on silica (Hx-DCM) to give product 1.5 g (54%). MS (m/z, FAB⁺): 741.6

Example 4

Synthesis of EX33

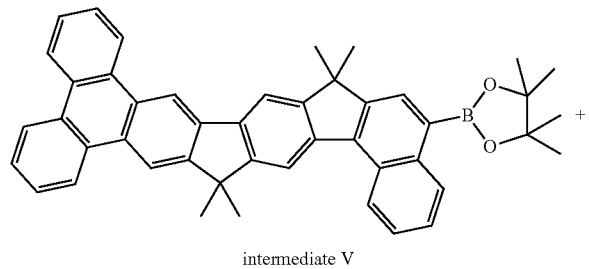
intermediate V

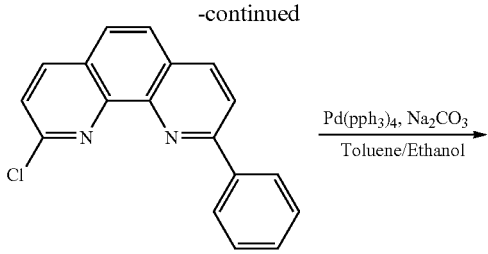

Pd(pph₃)₄, Na₂CO₃
Toluene/Ethanol

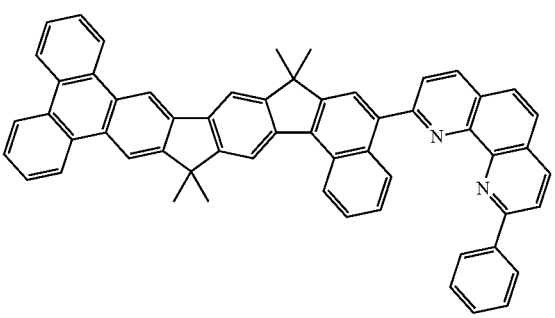

A mixture of 2.4 g (3.8 mmol) of intermediate V, 1.2 g (4.2 mmol) of 2-chloro-9-phenyl-1,10-phenanthroline, 0.11 g (0.1 mmol) of tetrakis(triphenylphosphine)palladium, 5 ml of 2M Na₂CO₃, 10 ml of EtOH and 20 ml toluene was degassed and placed under nitrogen, and then heated at 100° C. overnight. After finishing the reaction, the mixture was allowed to cool to room temperature. The solution was extracted with 100 ml of ethyl acetate and 200 ml of water. The organic layer was dried with anhydrous magnesium sulfate and the solvent was evaporated under reduced pressure. The residue was recrystallized from dichloromethane to give product 2.2 g (76%). MS (m/z, FAB⁺): 764.7

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis (phenyl)-benzidine (NPB) is most widely used as the hole transporting layer. N-(biphenyl-4-yl)-9,9-dimethyl-N-(4'-phenylbiphenyl-4-yl)-9H-fluoren-2-amine (EB2) is used as electron blocking layer, 10,10-Dimethyl-12-(4-(pyren-1-yl)phenyl)-10H-indeno[1,2-b]triphenylene (PT-312) is used as blue emitting host and N1,N1,N6,N6-tetram-tolylpyrene-1,6-diamine (D1) is used as blue guest. 2-(10,10-dimethyl-10H-indeno[2,1-b]triphenylen-13-yl)-9-phenyl-1,10-phenanthroline is used as electron transporting material (ET1) to co-deposit with 5% Li, 2-(10,10-dimethyl-10H-indeno[2,1-b]triphenylen-12-yl)-4,6-diphenyl-1,3,5-triazine is used as electron transporting material (ET2) to co-deposit with 8-hydroxyquinolato-lithium (LiQ) in organic EL device. Bis(2-methyl-8-quinolinolate)-4-(phenyl phenolato) aluminium (BAlq) is used as hole blocking material (HBM) and phosphorescent host for phosphorescent system. Bis(2-phenylpyridinato) (2,4-diphenylpyridinato)iridium(III)(D2) are used as phosphorescent dopant. The prior art of OLED materials for producing standard organic EL device control, comparable materials and EXAMPLES in this invention shown its chemical structure as follows:

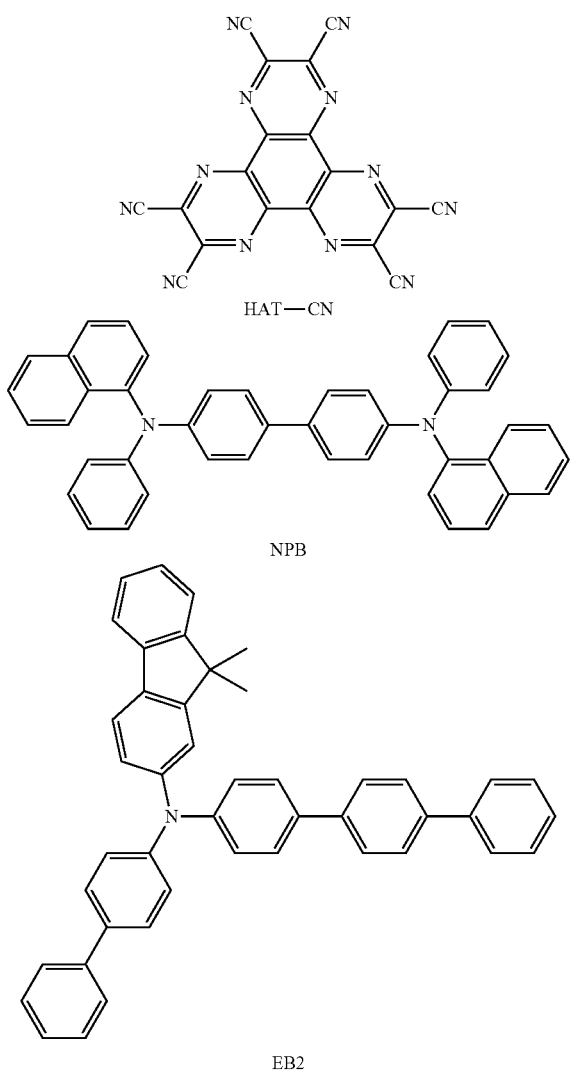

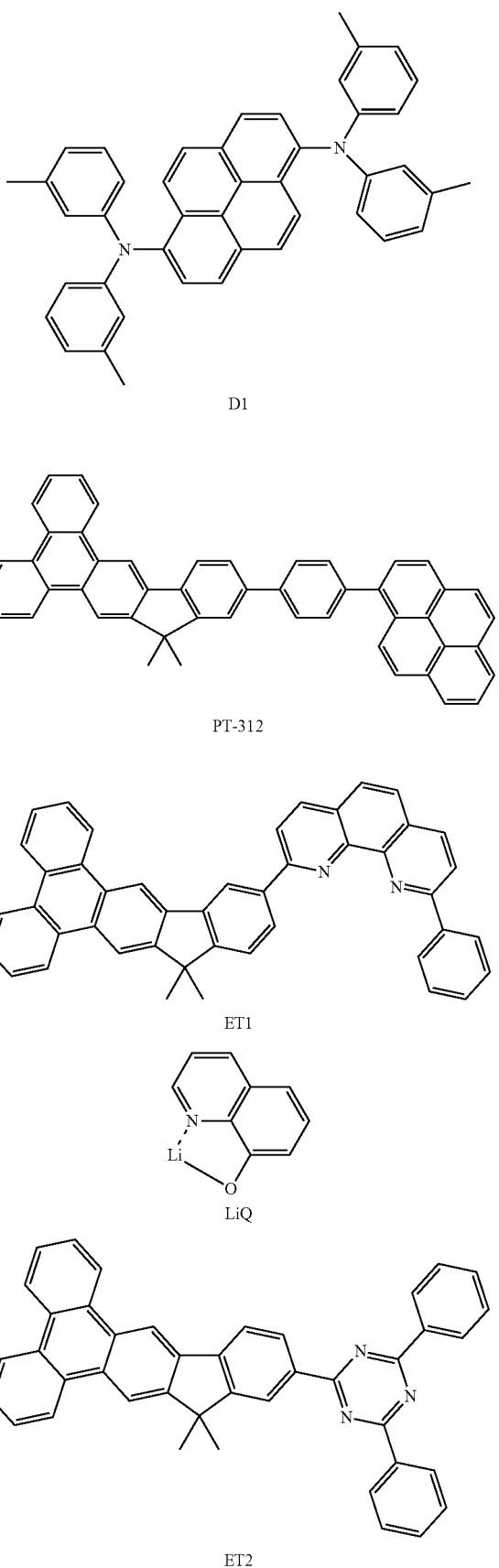

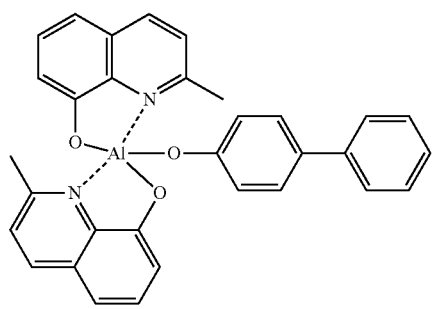

BAlq

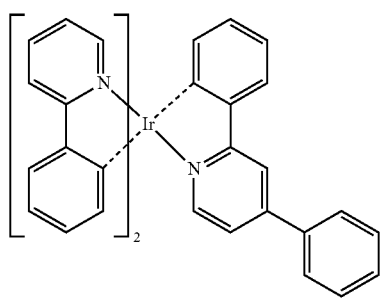

D2

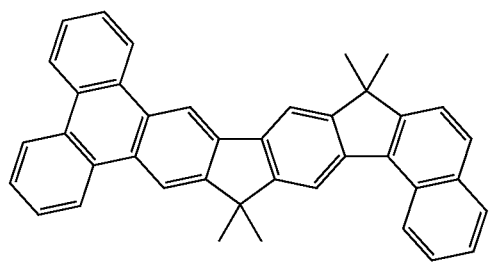

EX1

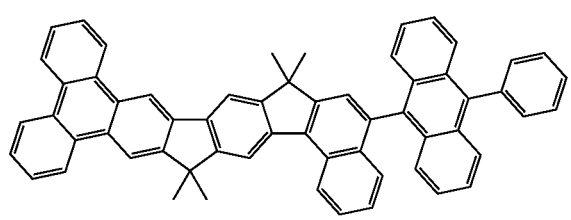

EX10

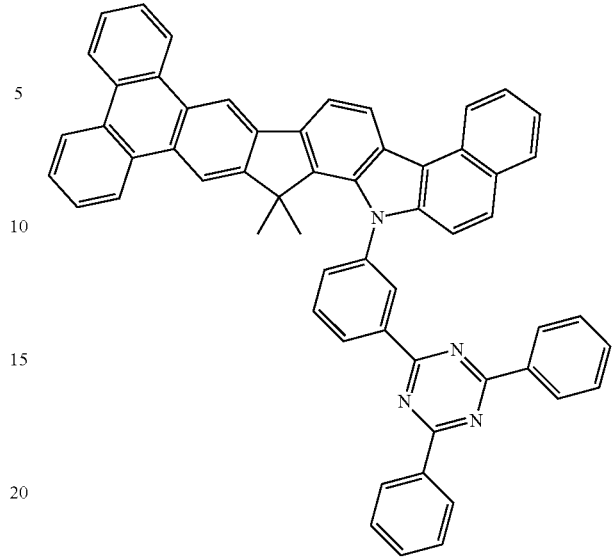

EX18

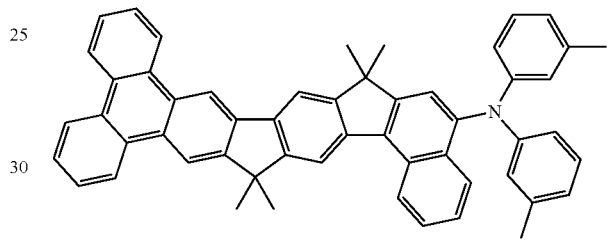

EX22

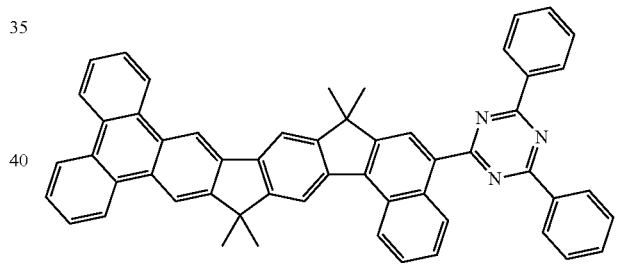

EX28

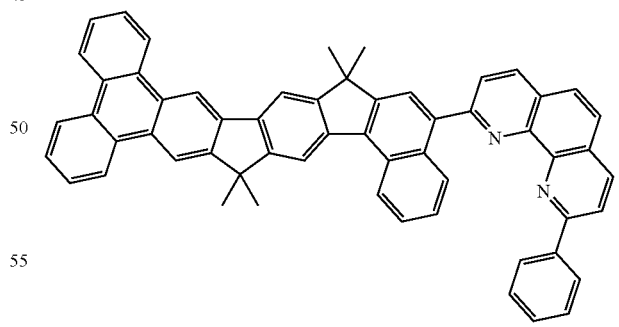

EX33

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 6

Figure 2:
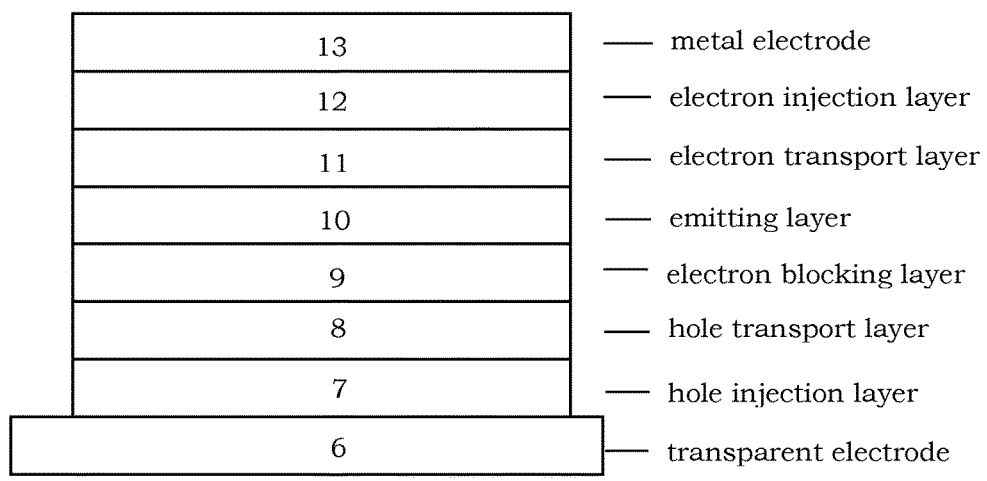
FIG. 2 show one example of organic EL device in the present invention. 6 is transparent electrode, 13 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is electron transport layer which is deposited onto 10, 12 is electron injection layer which is deposited on to 11.

Using a procedure analogous to the above mentioned general method, fluorescent blue-emitting organic EL device having the following device structure was produced (See FIG. 2): ITO/HAT-CN (10 nm)/NPB (800 nm)/EB2 (5 nm)/blue host doped 5% dopant (30 nm)/ET1 co-deposit 5% Li (35 nm)/Al (160 nm). The I-V-B (at 1000 nits) and half-life time of fluorescent blue-emitting organic EL device testing report as Table 1, The half-life time is defined that the initial luminance of 1000 cd/m$^2$ has dropped to half.

TABLE 1

| Blue host | Dopant | Voltage (V) | Efficiency (cd/A) | CIE (y) | Half-life time (hour) |
|---|---|---|---|---|---|
| PT-312 | D1 | 5.0 | 5.2 | 0.178 | 260 |
| EX1 | D1 | 4.5 | 4.1 | 0.161 | 130 |
| EX10 | D1 | 4.6 | 5.6 | 0.174 | 395 |
| PT-312 | EX22 | 4.8 | 4.0 | 0.139 | 90 |
| EX10 | EX22 | 5.2 | 4.3 | 0.138 | 150 |

Example 7

Using a procedure analogous to the above mentioned general method, fluorescent blue-emitting organic EL device having the following device structure was produced (See FIG. 1): ITO/HAT-CN (10 nm)/NPB (800 nm)/PT-312 doped 5% D1 (30 nm)/hole blocking material (HBM)(5 nm)/electron transport material (ETM) co-deposit 5% Li/Al (160 nm). The I-V-B (at 1000 nits) and half-life time of fluorescent blue-emitting organic EL device testing report as Table 2, The half-life time is defined that the initial luminance of 1000 cd/m$^2$ has dropped to half.

TABLE 2

| ETM | HBM | Voltage (V) | Efficiency (cd/A) | CIE (y) | Half-life time (hour) |
|---|---|---|---|---|---|
| ET1 | ET2 | 4.8 | 5.5 | 0.181 | 280 |
| ET1 | EX28 | 4.8 | 5.4 | 0.183 | 330 |
| EX33 | ET2 | 5.2 | 5.6 | 0.179 | 320 |
| EX33 | — | 5.1 | 5.3 | 0.183 | 120 |

Example 8

Figure 3:
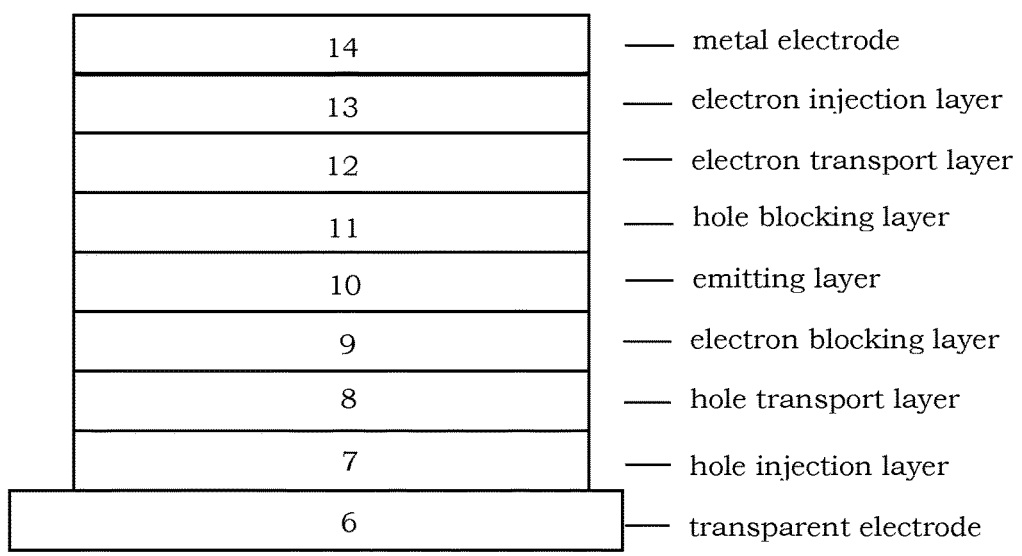
FIG. 3 show one example of organic EL device in the present invention. 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited onto 11, 13 is electron injection layer which is deposited on to 12.

Using a procedure analogous to the above mentioned general method, phosphorescent emitting organic EL device having the following device structures are produced (See FIG. 3.): ITO/HAT-CN (10 nm)/NPB (800 nm)/EBM (5 nm)/phosphorescent host (PHhost)+15% D2 (30 nm)/HBM (10 nm)/ET2 co-deposit 50% LiQ (35 nm)/LiQ (5 nm)/Al (160 nm). The I-V-B (at 1000 nits) and half-life time of phosphorescent emitting organic EL device testing report as Table 3. The half-life time is defined that the initial luminance of 3000 cd/m$^2$ has dropped to half.

TABLE 3

| PHhost | HBM | Voltage (V) | Efficiency (cd/A) | CIE (x, y) | Half-life time (hour) |
|---|---|---|---|---|---|
| BAlq | ET2 | 6.3 | 25 | 0.45, 0.56 | 260 |
| EX18 | ET2 | 4.5 | 32 | 0.42, 0.58 | 470 |
| EX18 | EX28 | 4.0 | 28 | 0.42, 0.57 | 440 |
| EX18 | — | 4.5 | 22 | 0.42, 0.58 | 300 |

In the above preferred embodiments for organic EL device test report (see Table 1 to Table 3), we shown that the material with a general formula (1) or formula (2) used as emitting host or dopant, hole blocking layer (HBL), electron blocking layer (EBL), electron transport layer (ETL) and hole transport layer (HTL) in the present invention display good performance than the prior art of OLED materials.

To sum up, the present invention discloses a material which can be used for organic EL device is disclosed. More specifically, an organic EL device employing the material as emitting host or dopant, hole blocking layer (HBL), electron blocking layer (EBL), electron transport layer (ETL) and hole transport layer (HTL). The mentioned the material is represented by the following formula (1) or formula (2):

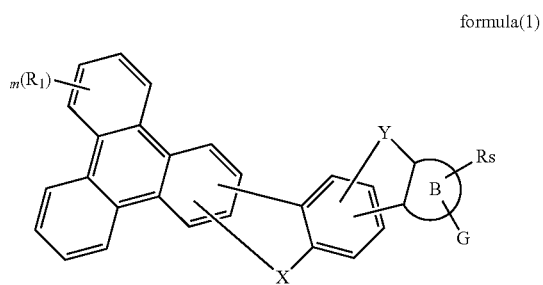

formula(1)

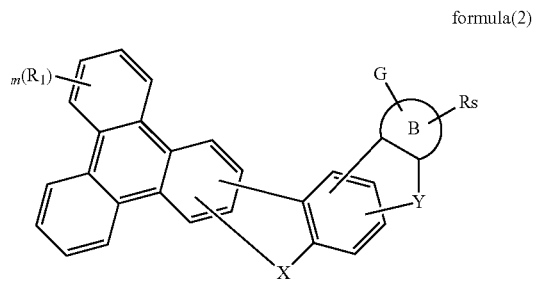

formula(2)

wherein B represents a fused ring hydrocarbon units with two or three rings, m represents an integer of 0 to 10, X and Y are divalent bridge selected from the atom or group consisting from O, S, C(R$_2$)(R$_3$), Si(R$_4$)(R$_5$), NR$_6$, G or R$_6$ are selected from the group consisting of a hydrogen, a halide, a substituted or unsubstituted aryl group having 6 to 60 carbon atoms or a substituted or unsubstituted heteroaryl group having 3 to 60 carbon atoms, and provided that G or R$_6$ represent a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ to $R_5$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

What is claimed is:

1. A material with a general formula (1) or general formula (2) as follows:

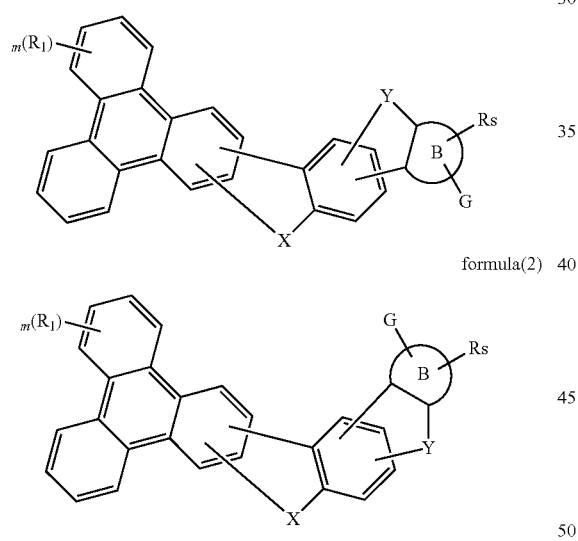

formula(1)

formula(2)

wherein B represents a fused ring hydrocarbon units with two or three rings, m represents an integer of 0 to 10, X and Y are divalent bridge selected from the atom or group consisting from O, S, $C(R_2)(R_3)$, $Si(R_4)(R_5)$, $NR_6$, G or $R_6$ are selected from the group consisting of a hydrogen, a halide, a substituted or unsubstituted aryl group having 6 to 60 carbon atoms or a substituted or unsubstituted heteroaryl group having 3 to 60 carbon atoms, and provided that G or $R_6$ represent a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ to $R_5$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The material according to claim 1, wherein the G or $R_6$ are represented by the following formulas:

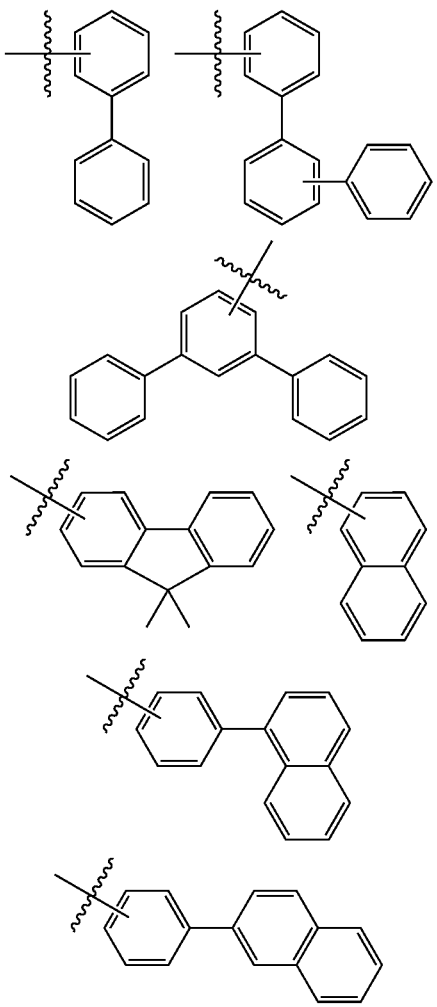

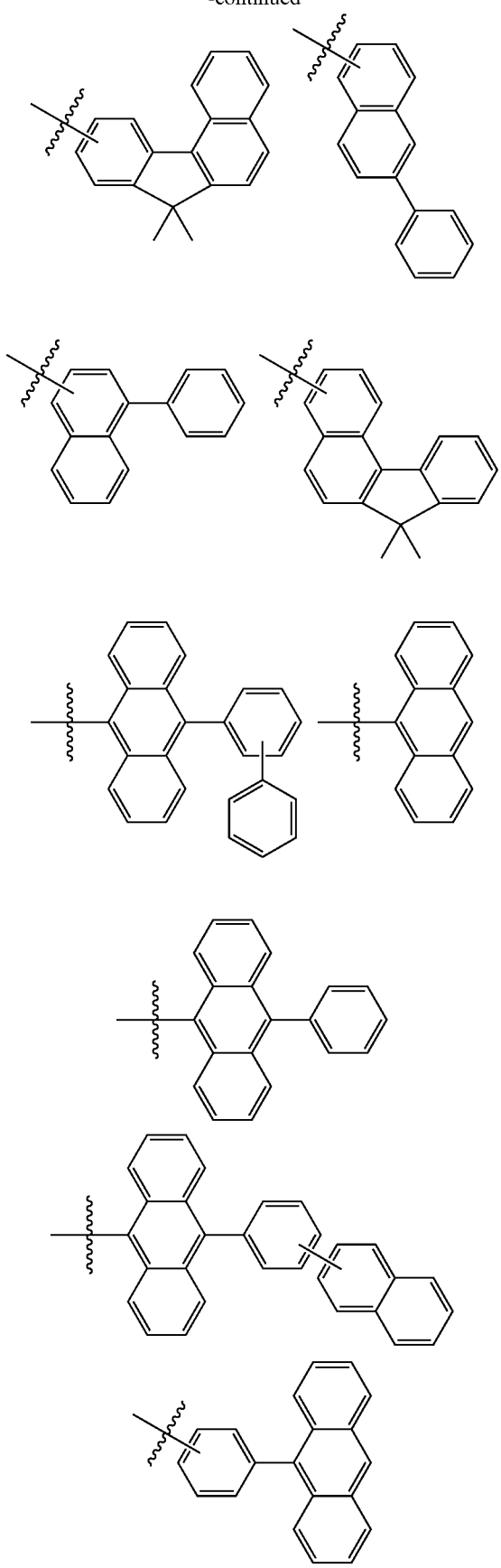
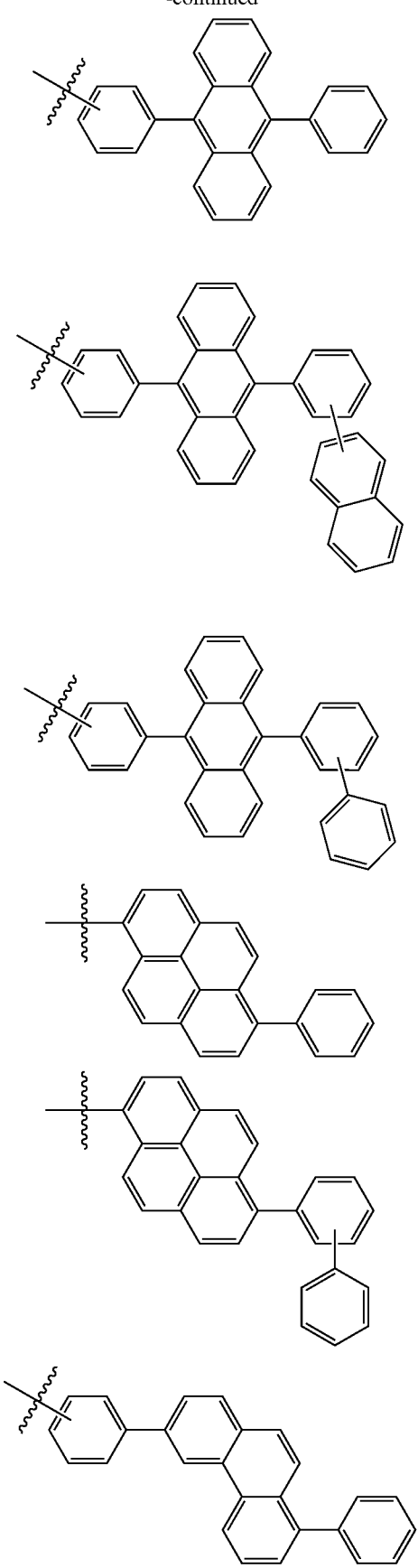

-continued
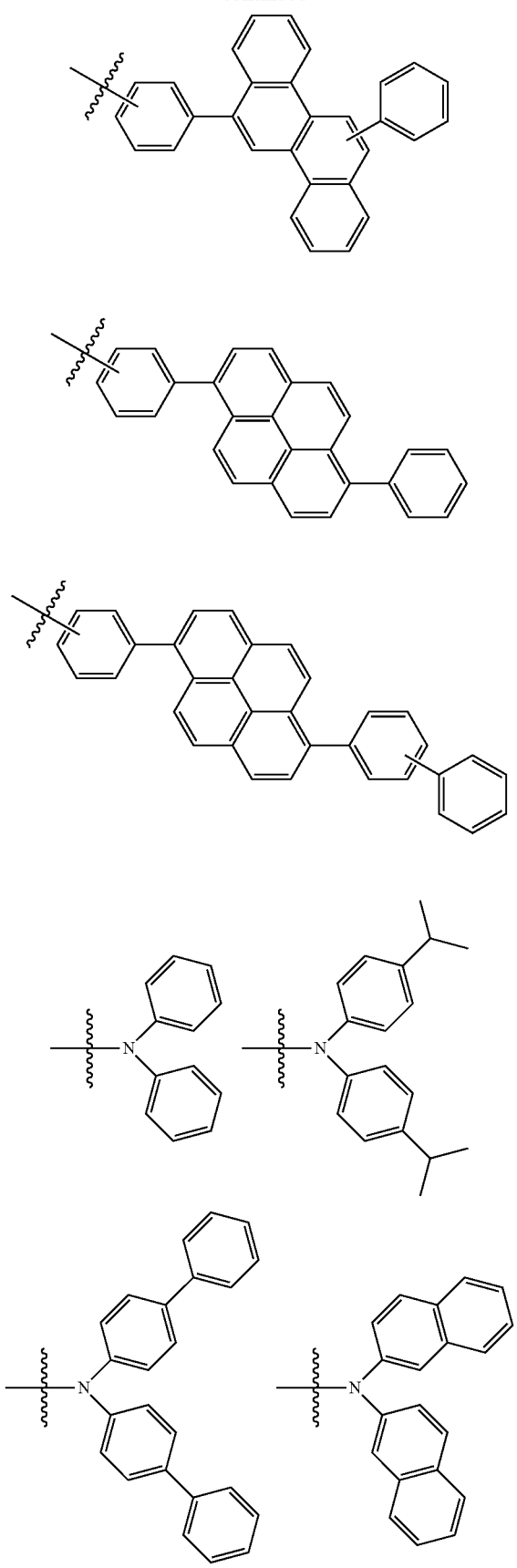
-continued
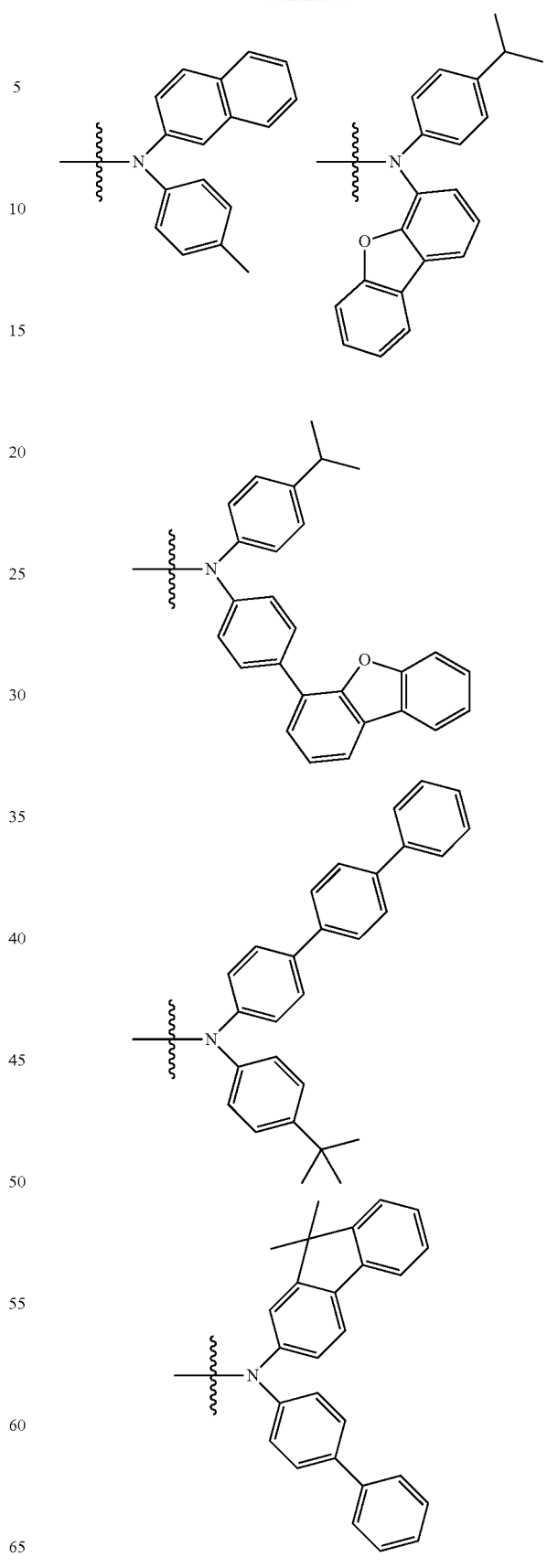

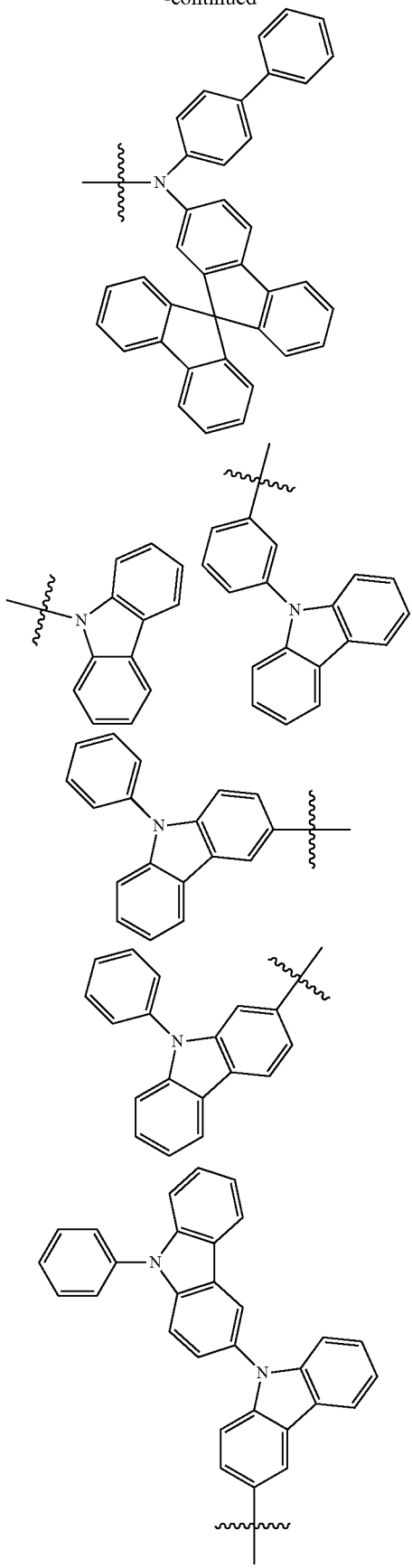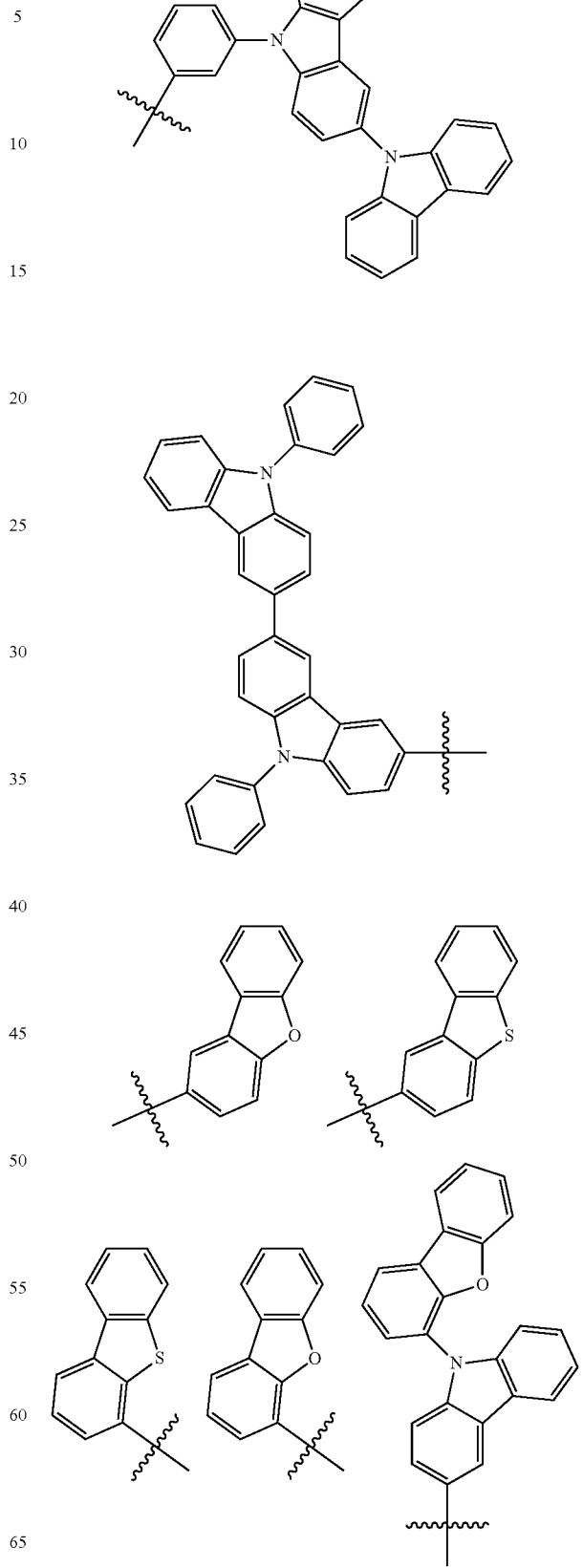

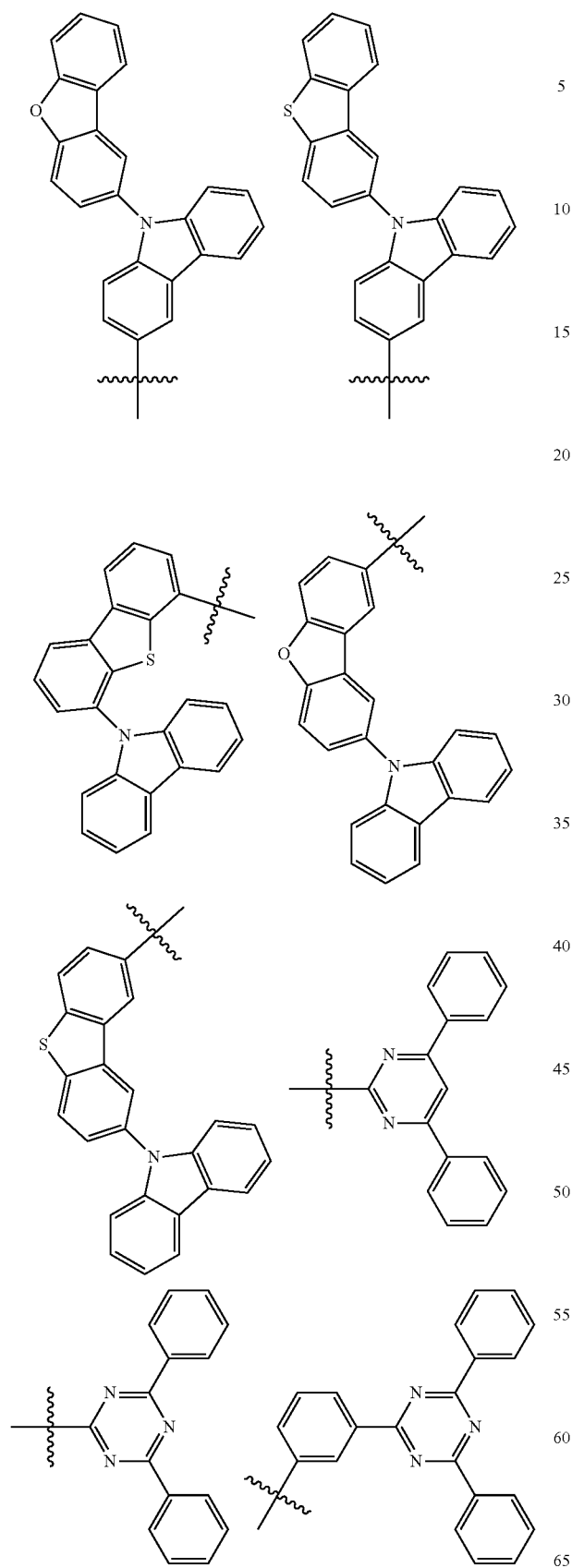
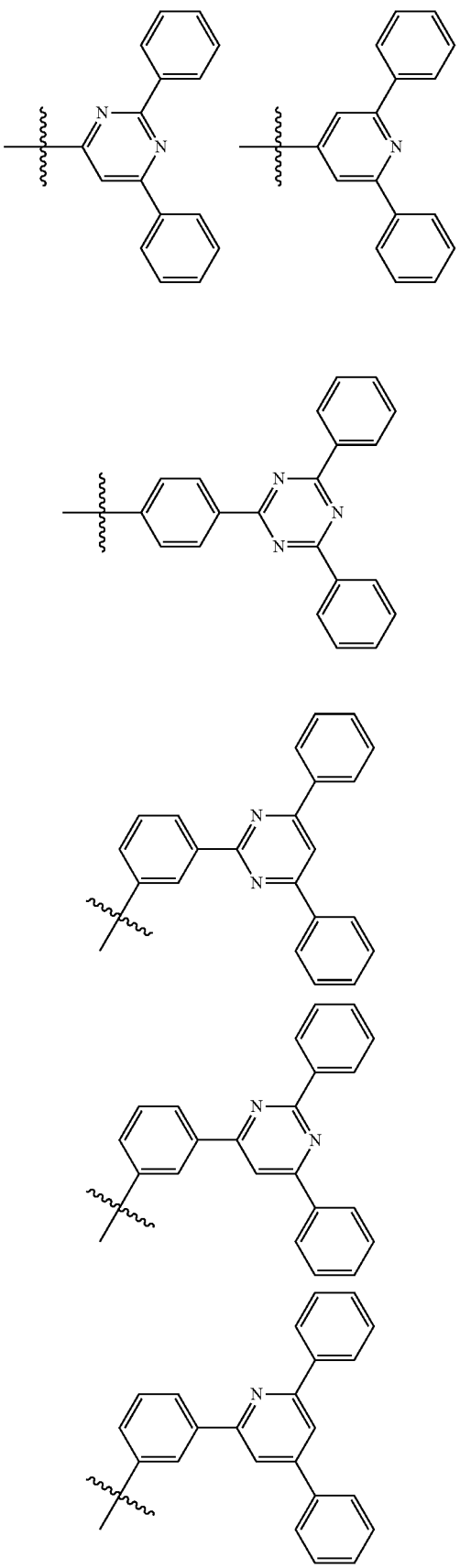

83
-continued
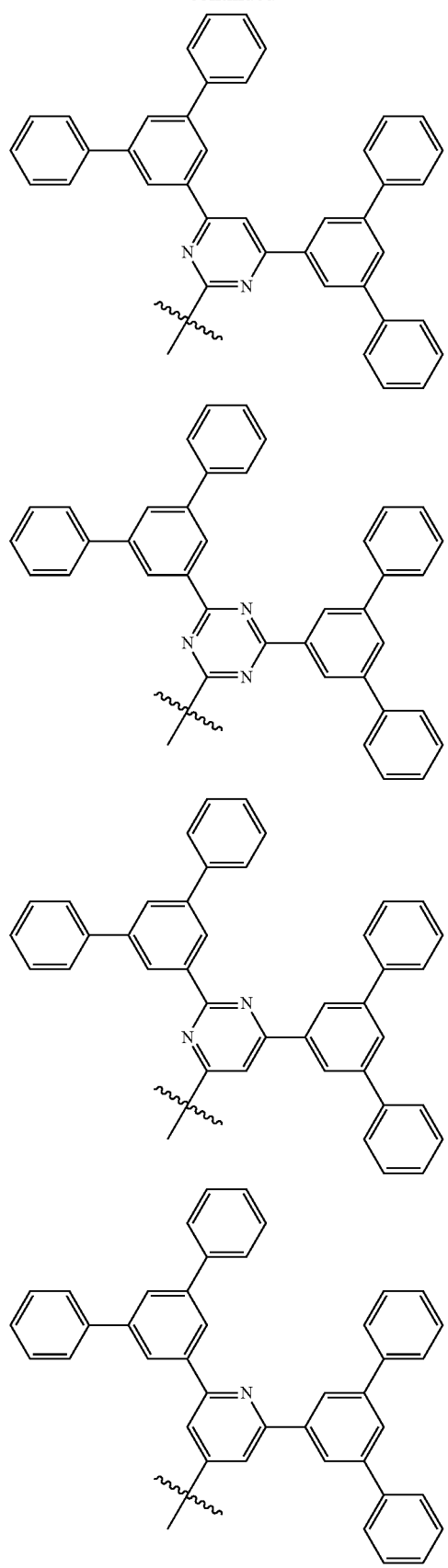
84
-continued
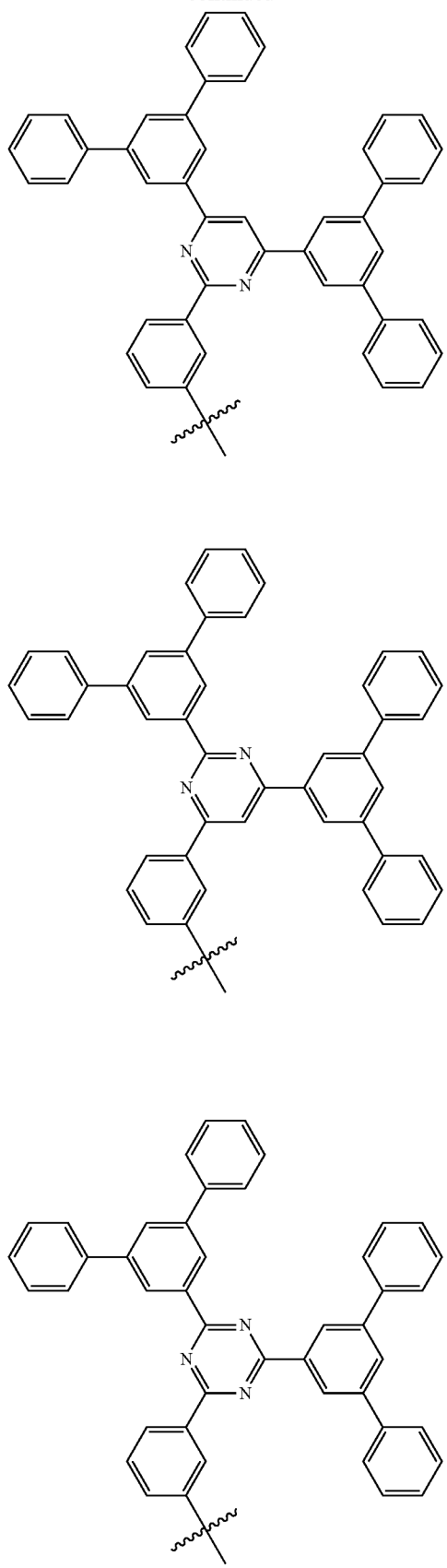

-continued

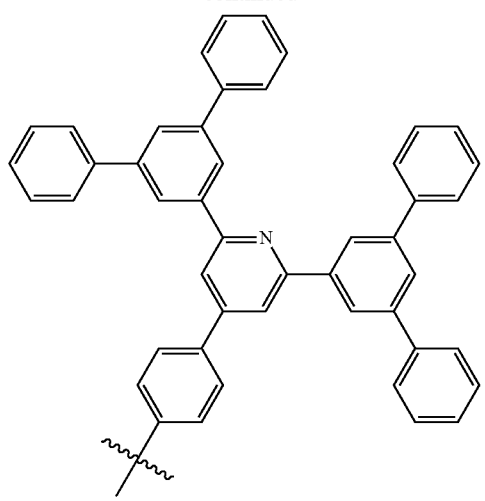

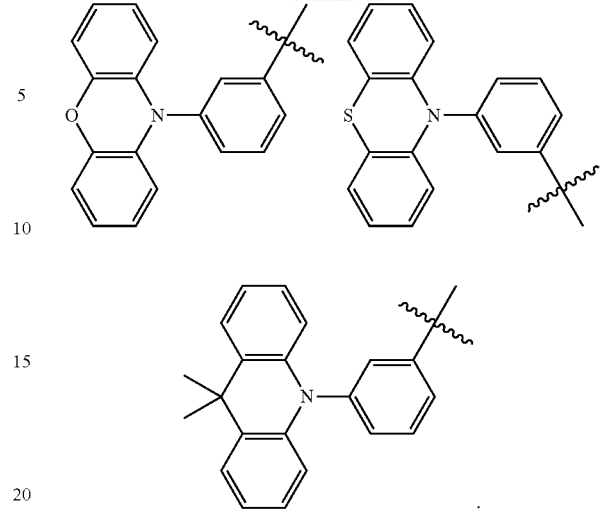

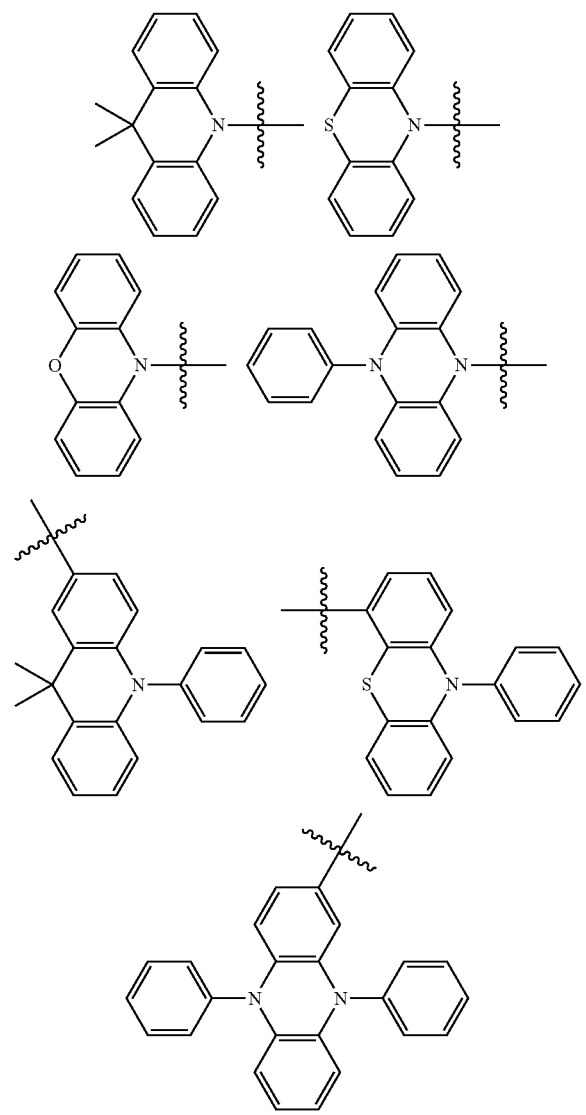

3. The material according to claim 1, wherein the material is represented by the following formula (3) or formula (4):

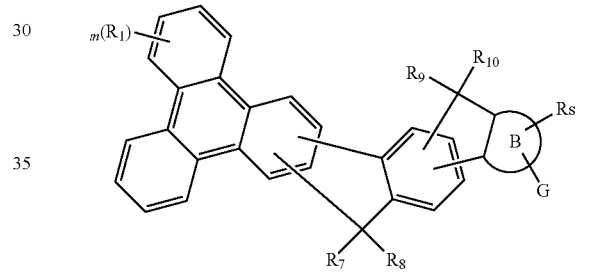

formula(3)

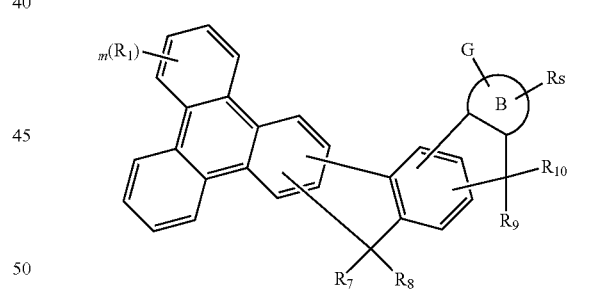

formula(4)

wherein B represents a fused ring hydrocarbon units with two or three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ and $R_7$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

4. The material according to claim 3, wherein the G is represented by the following formulas:

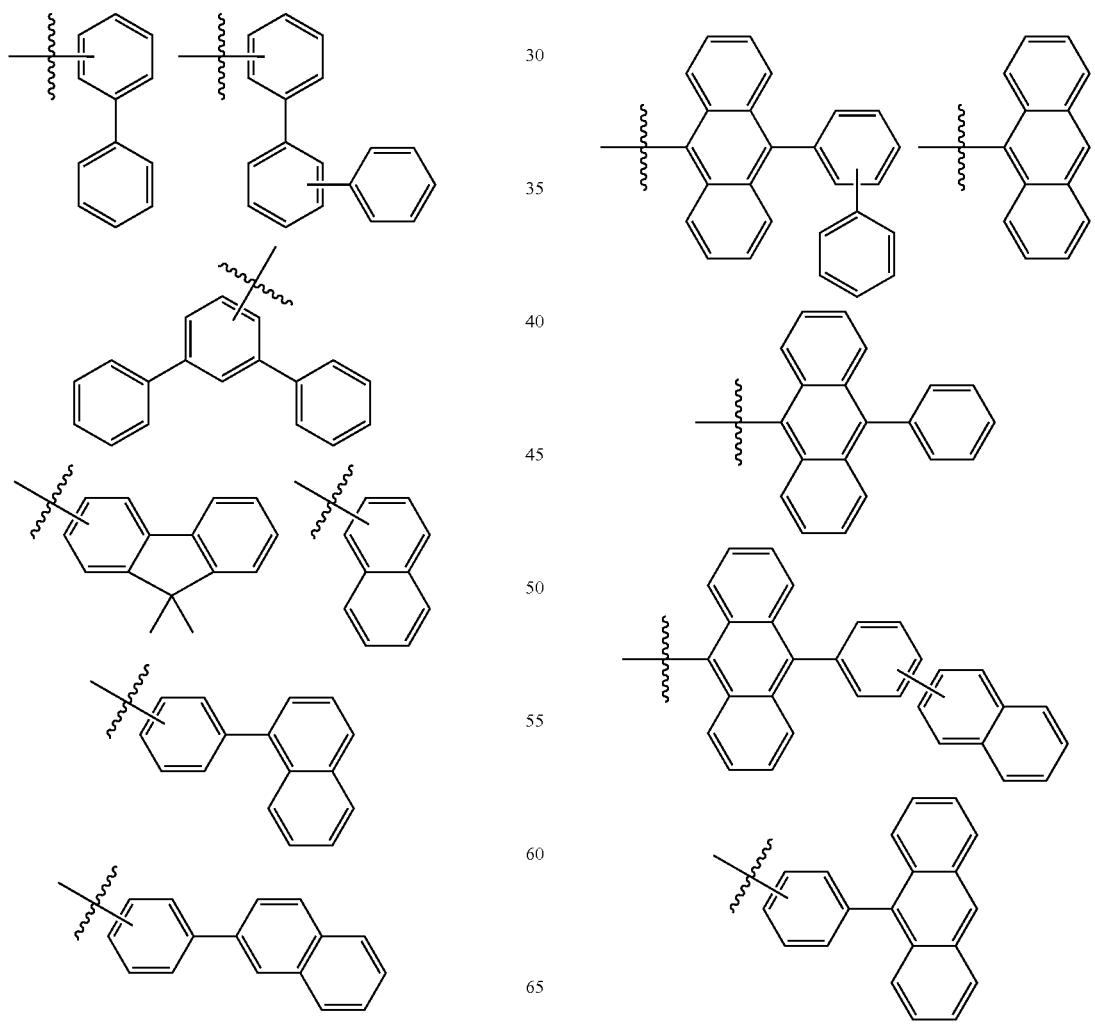

89
-continued
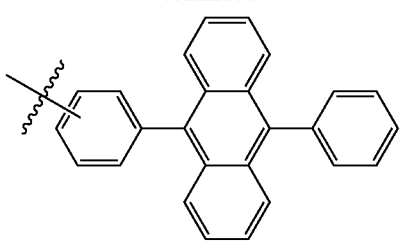
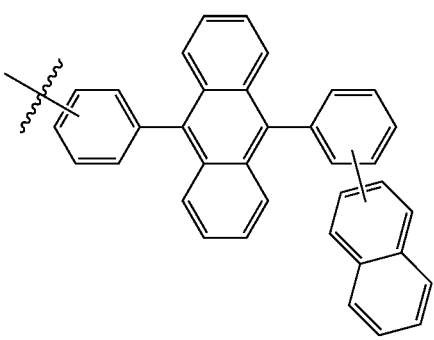
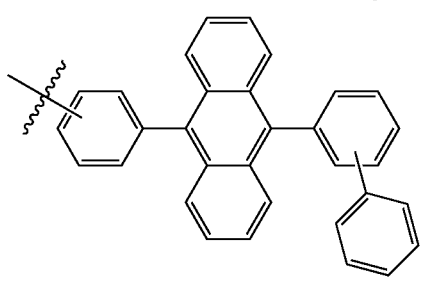
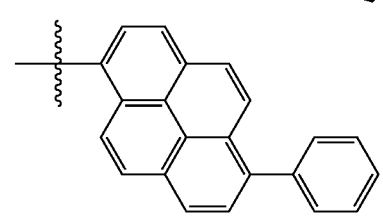
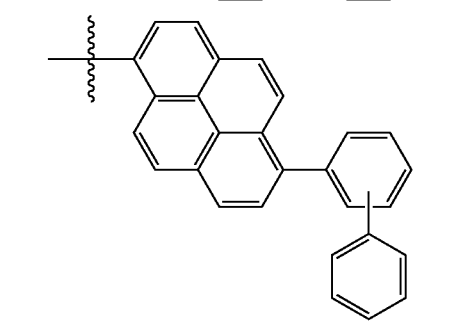
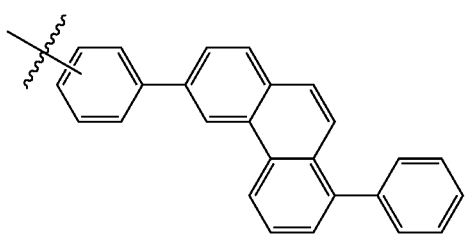
90
-continued
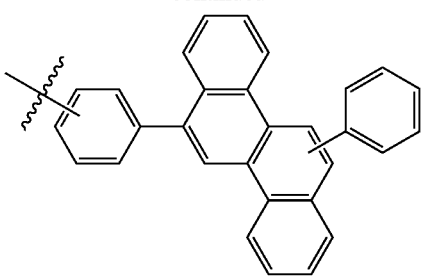
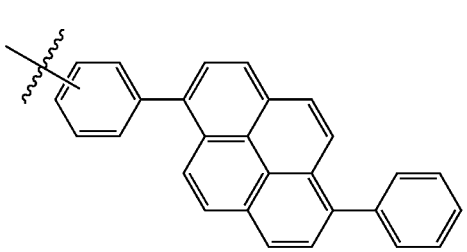
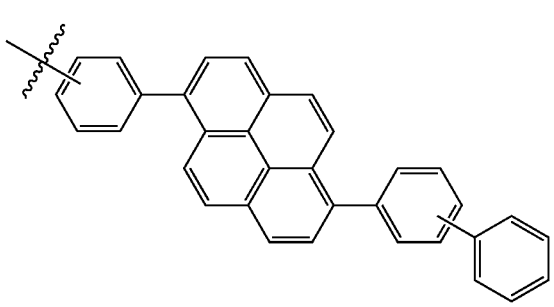
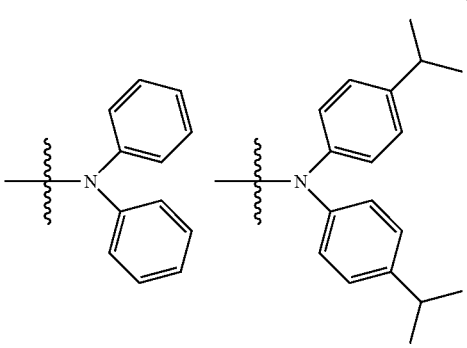
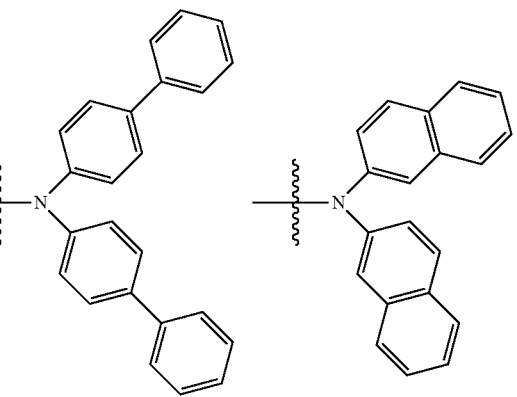

91
-continued
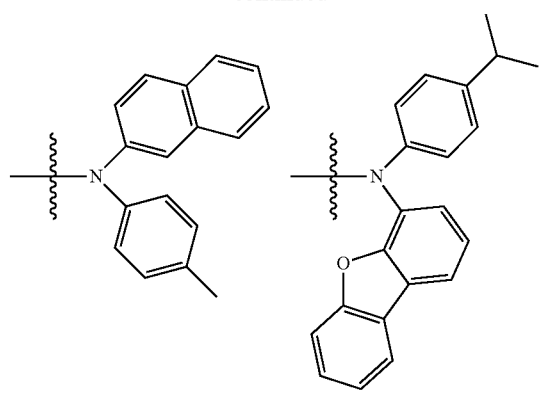
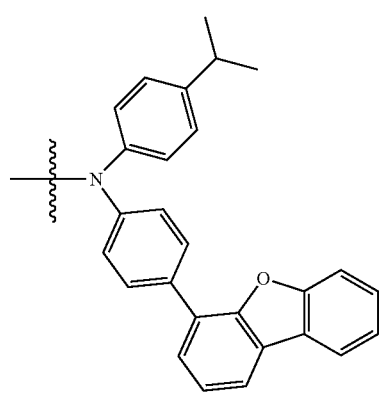
92
-continued
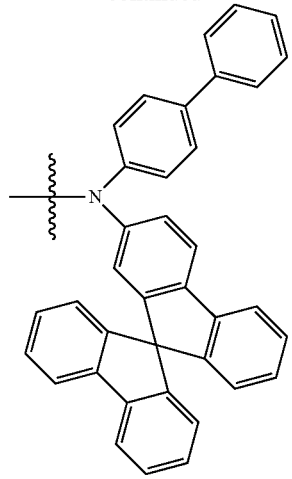
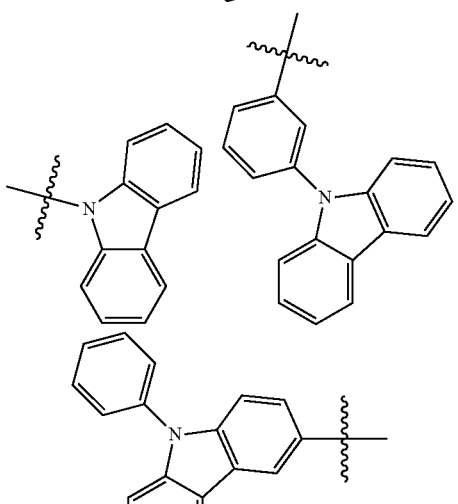
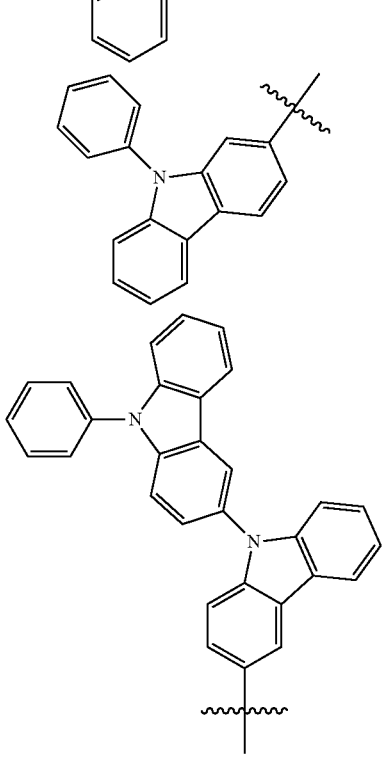

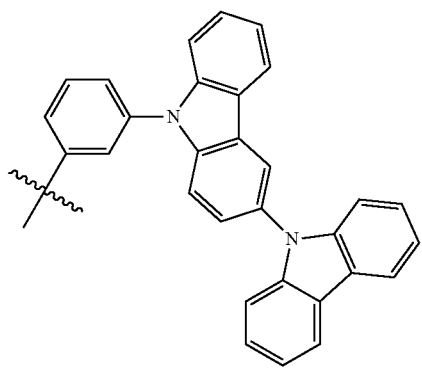
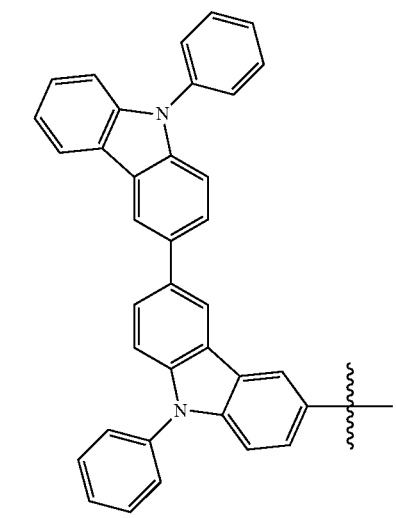
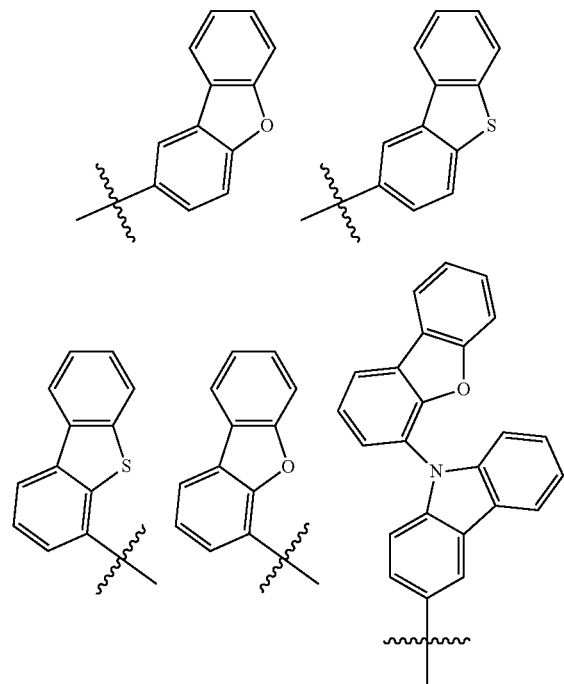
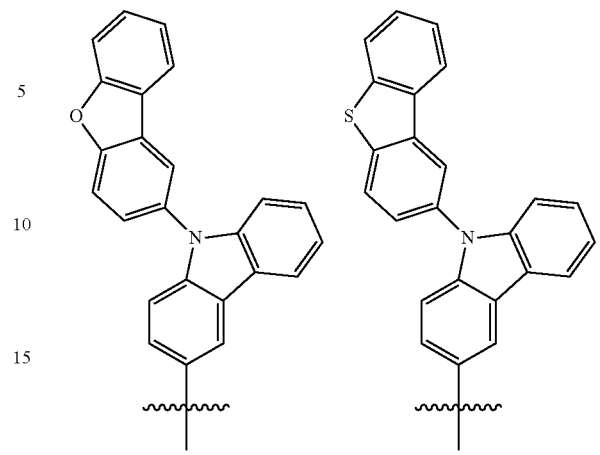
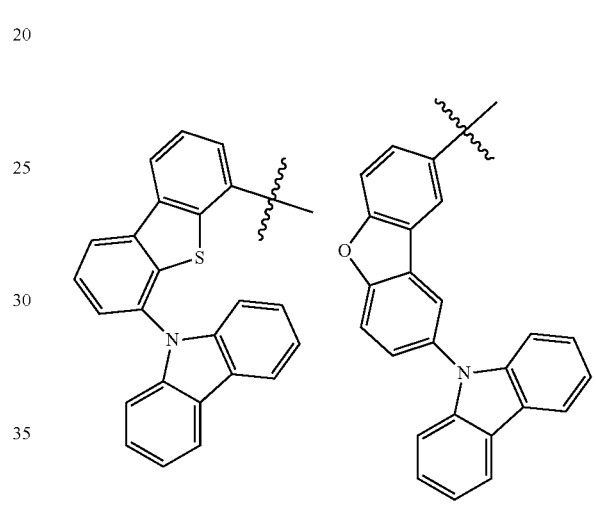
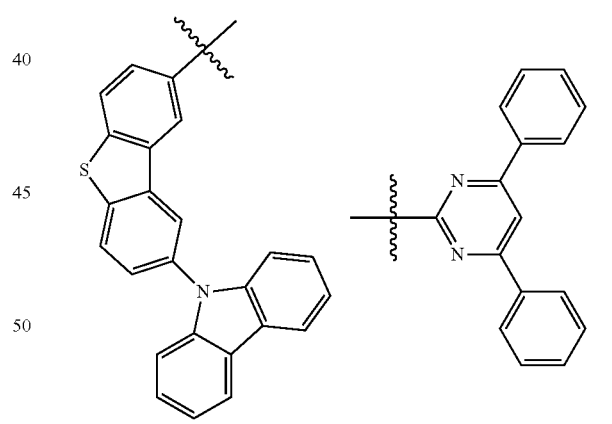
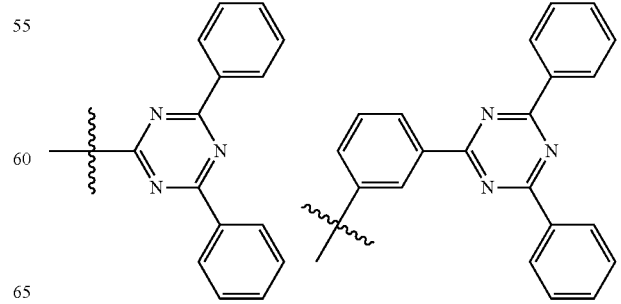

-continued
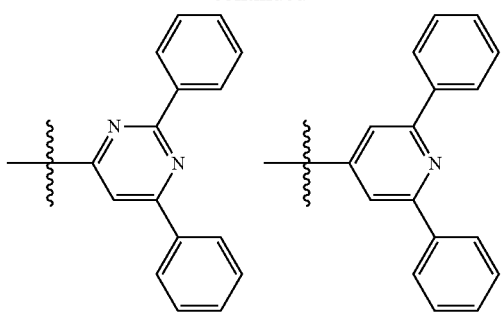
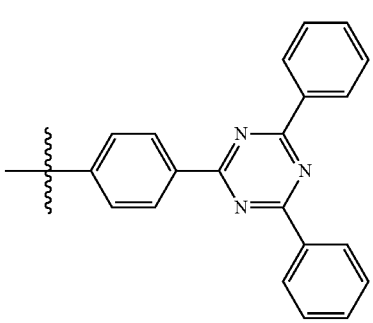
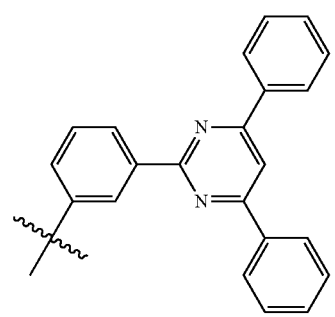
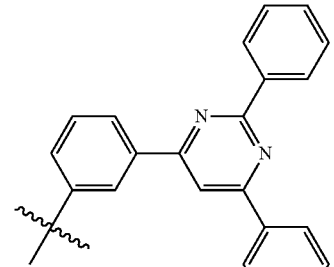
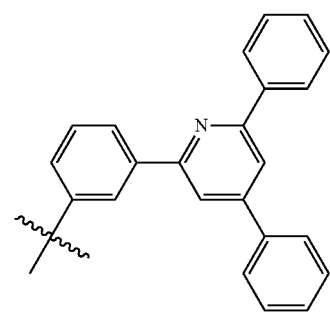
-continued
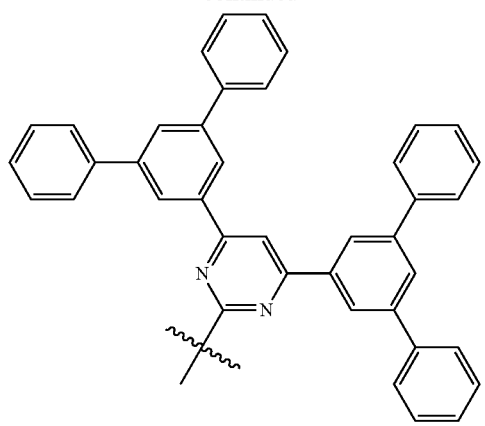
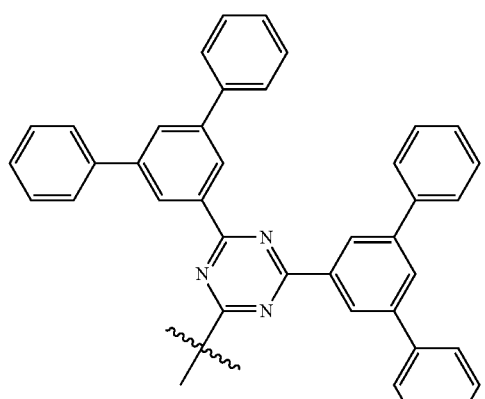
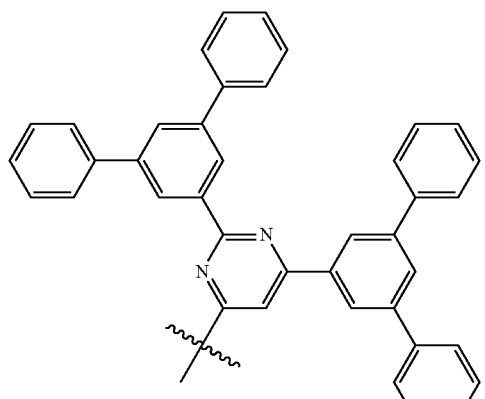
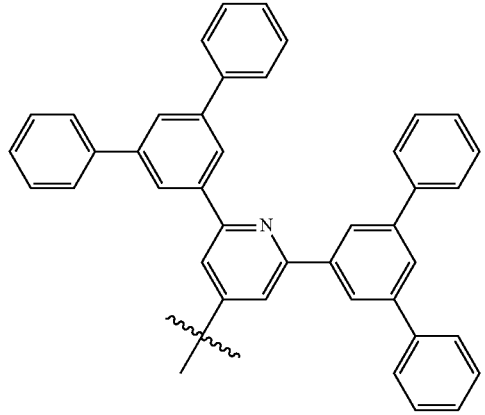

97
-continued
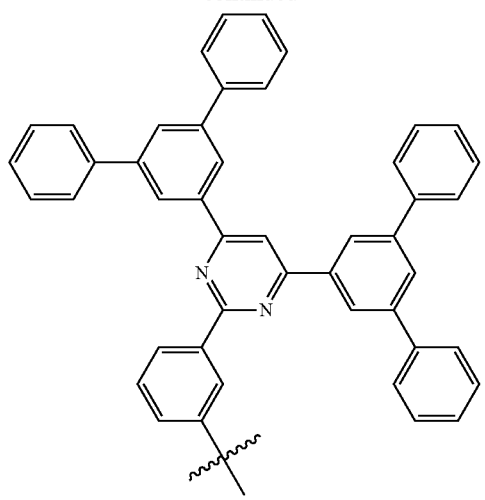
98
-continued
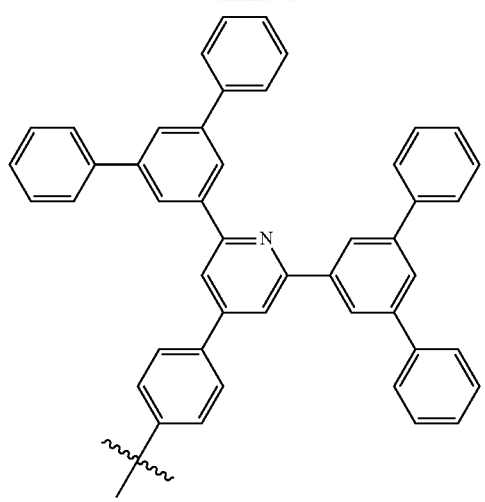
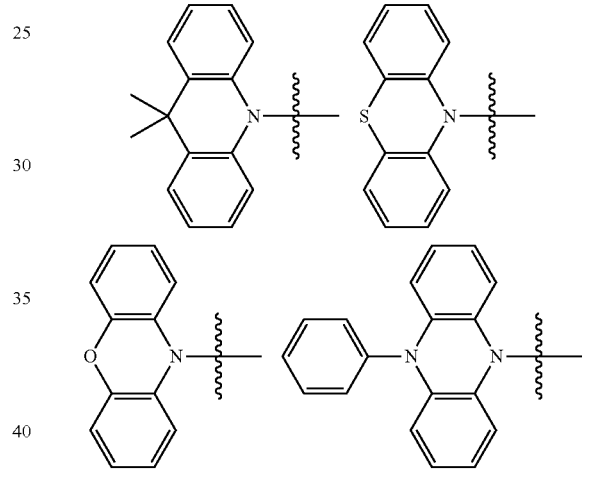
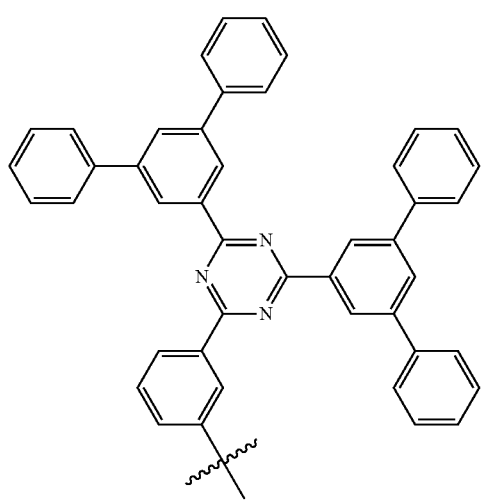

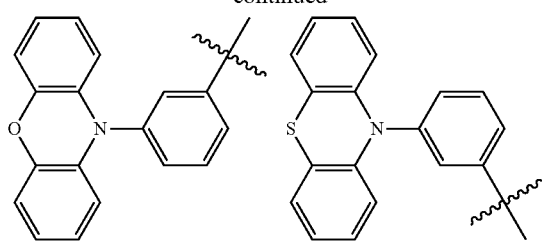
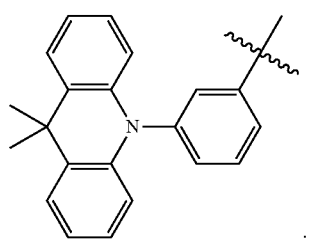
5. The material according to claim 3, wherein the material is represented by the following formula (5) to formula (22):
formula(5)
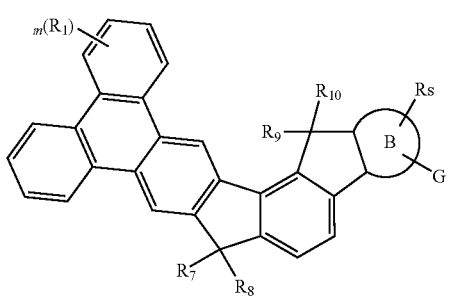
formula(6)
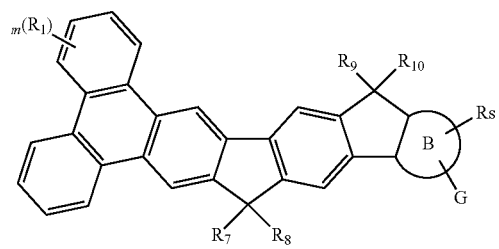
formula(7)
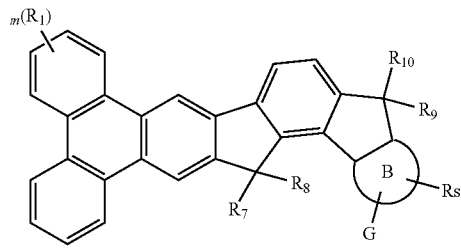
formula(8)
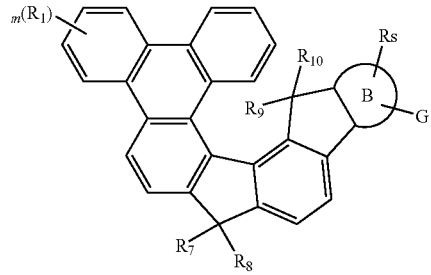
formula(9)
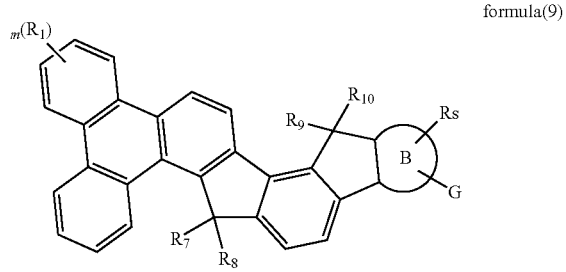
formula(10)
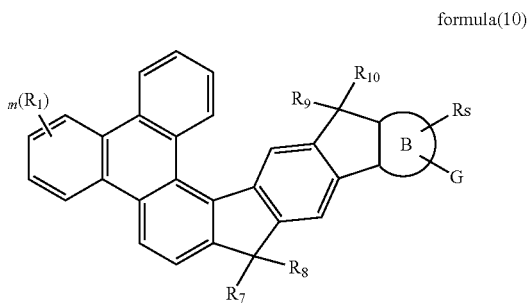
formula(11)
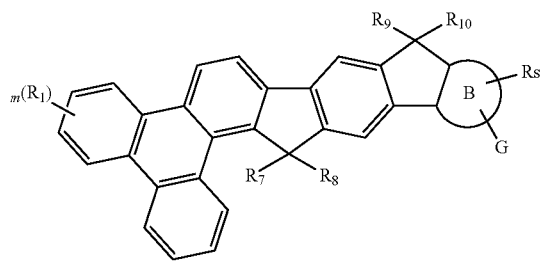
formula(12)
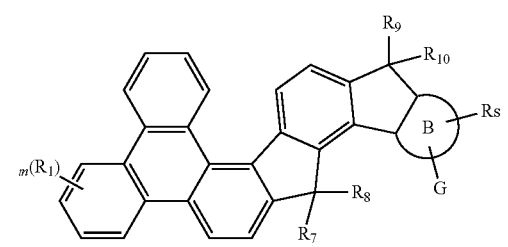

formula(13)
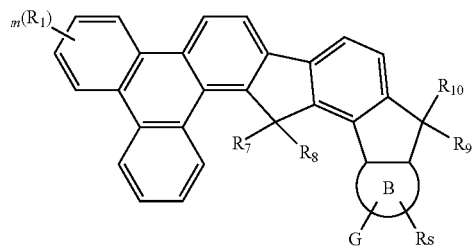

formula(14)
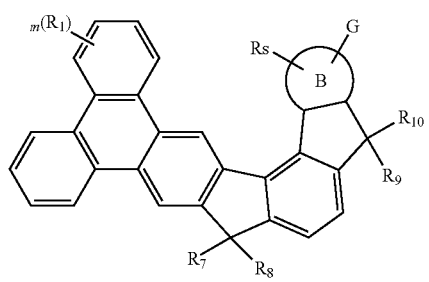

formula(15)
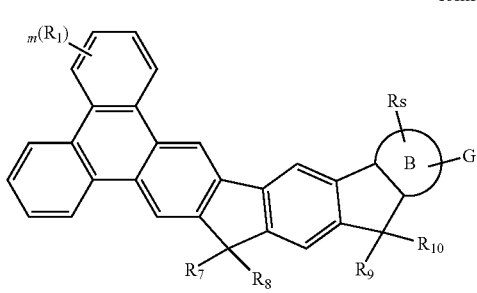

formula(16)
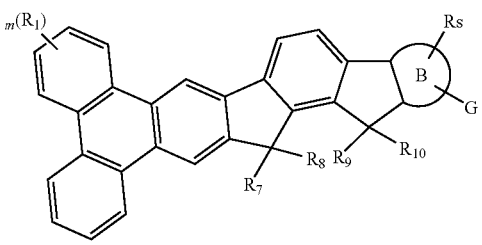

formula(17)
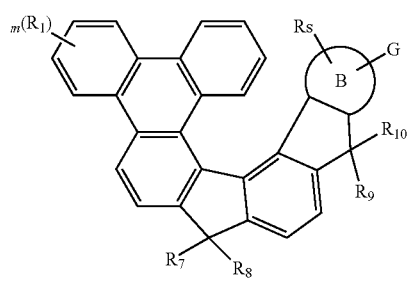

formula(18)
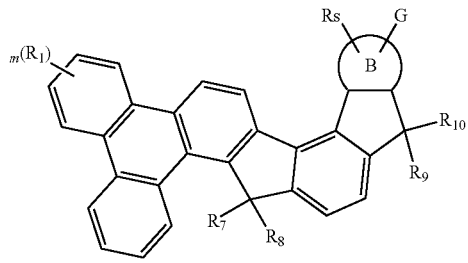

formula(19)
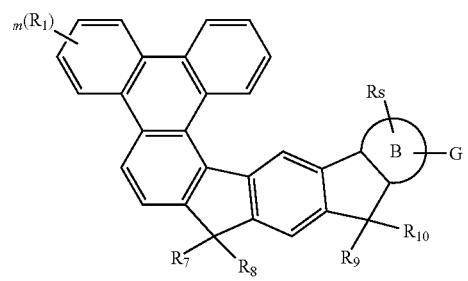

formula(20)
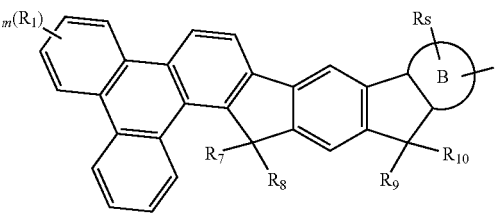

formula(21)
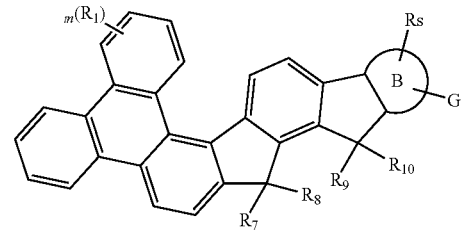

formula(22)
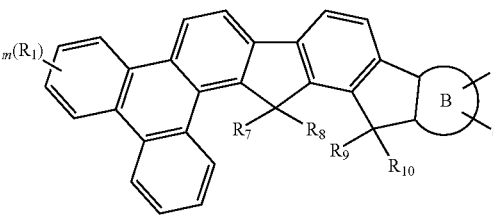

wherein B represents a fused ring hydrocarbon units with two or three rings, m represents an integer of 0 to 10, G is selected from the group consisting of a hydrogen, a halide, a substituted or unsubstituted aryl group having 6 to 60 carbon atoms or a substituted or unsubstituted heteroaryl group having 3 to 60 carbon atoms, and provided that G represents a substituted or unsubstituted phenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted arylamine group, a substituted or unsubstituted heteroarylamine group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; Rs represents a hydrogen, a halide or a substituent, $R_1$ and $R_7$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

6. The material according to claim 5, wherein the G is represented by the following formulas:

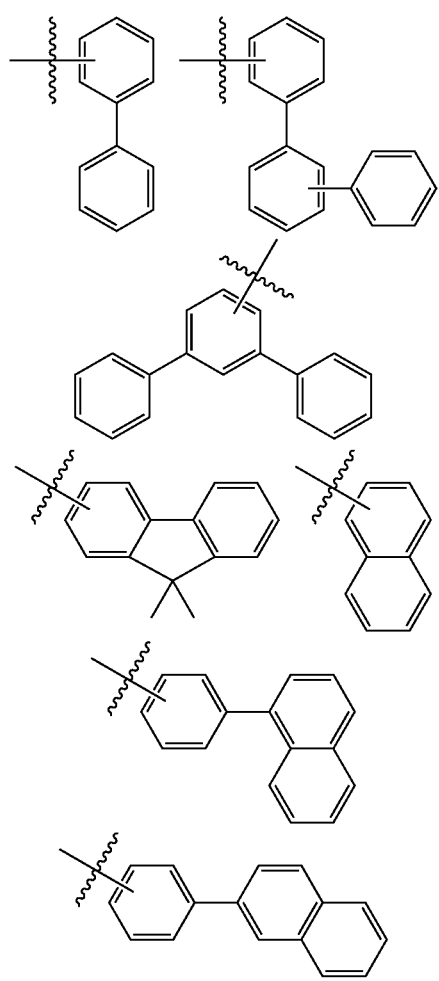

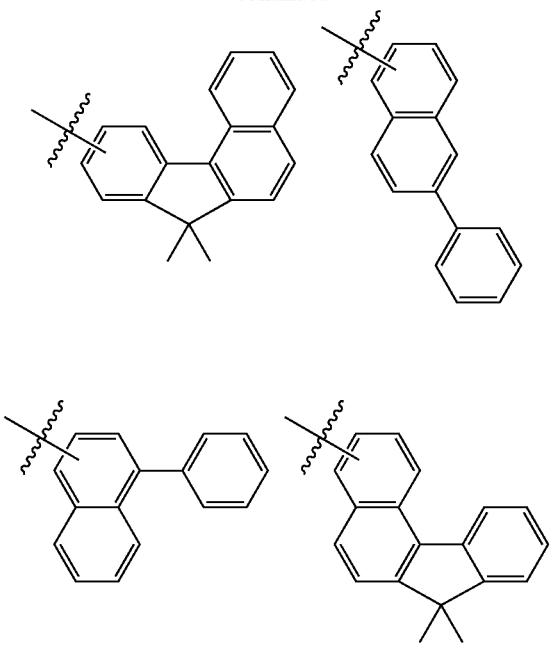

-continued

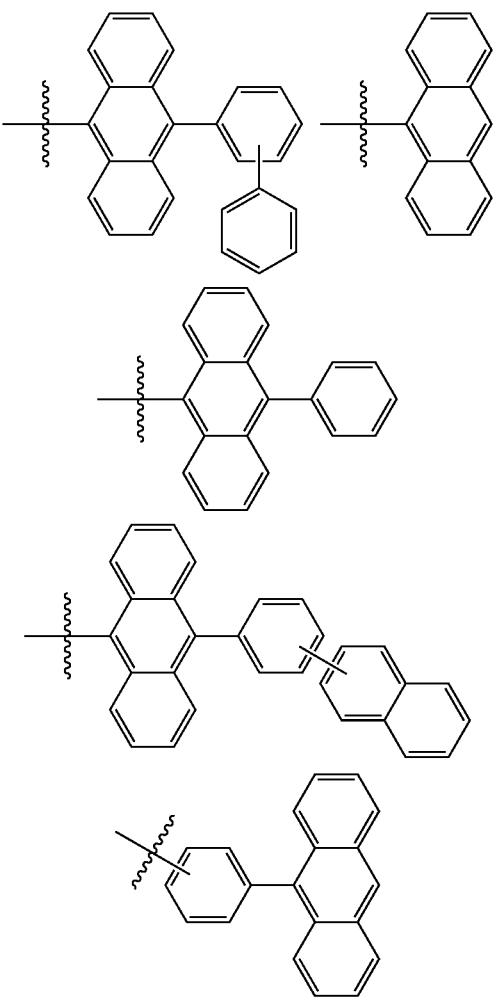

105
-continued
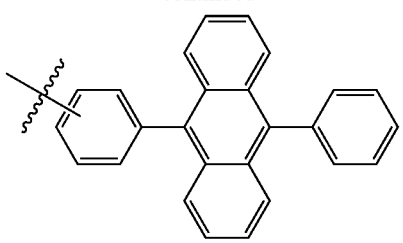
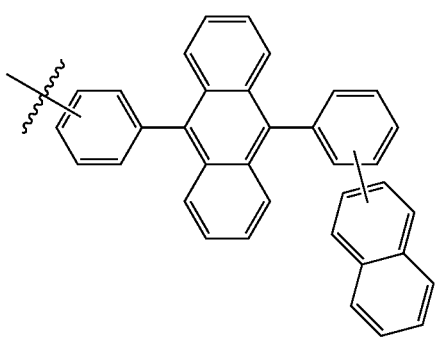
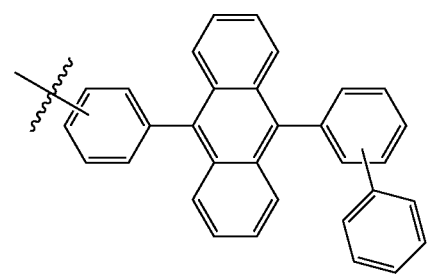
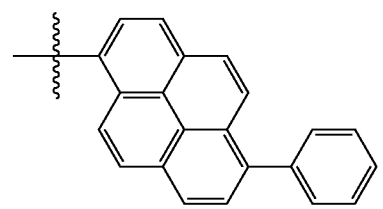
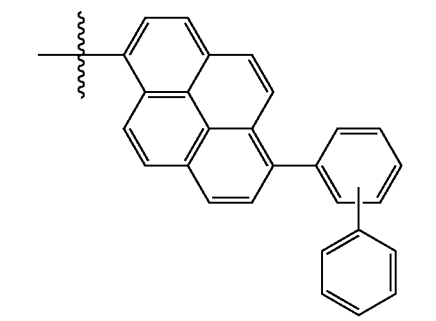
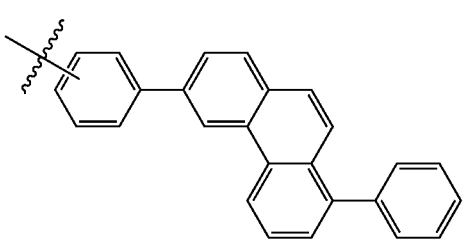
106
-continued
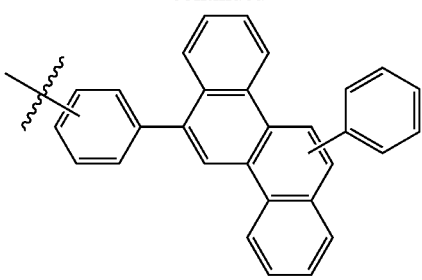
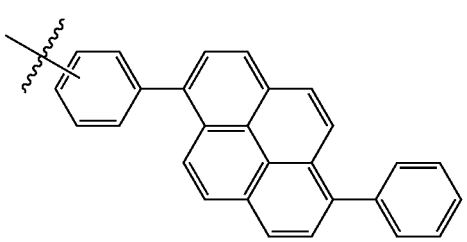
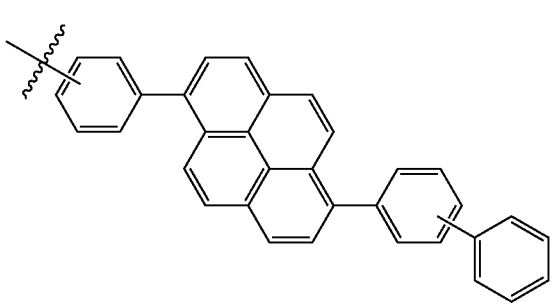
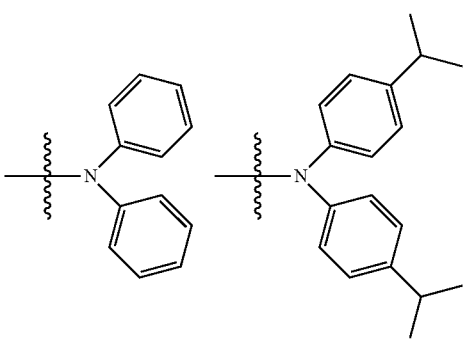
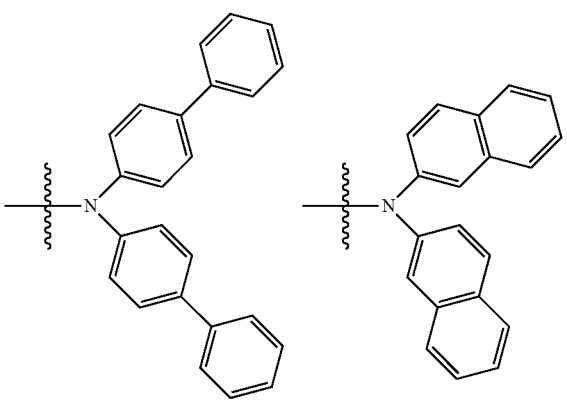

107
-continued
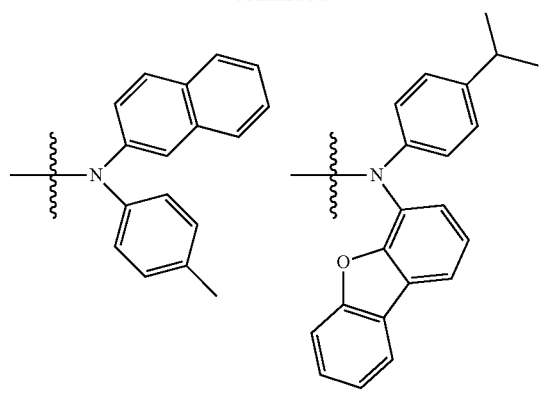
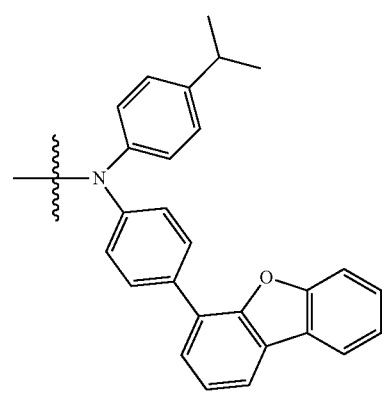
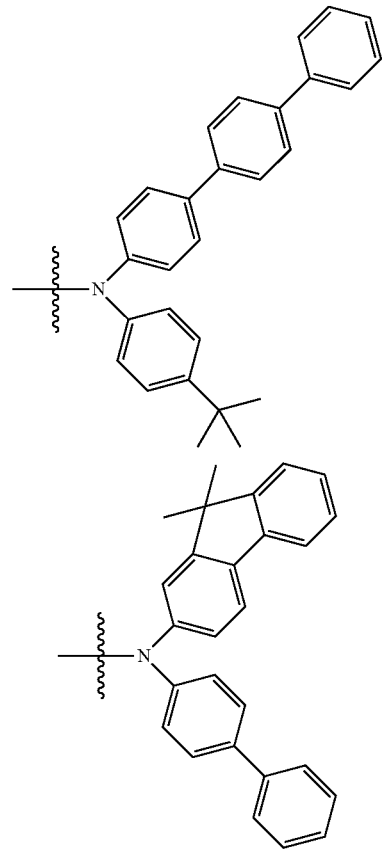
108
-continued
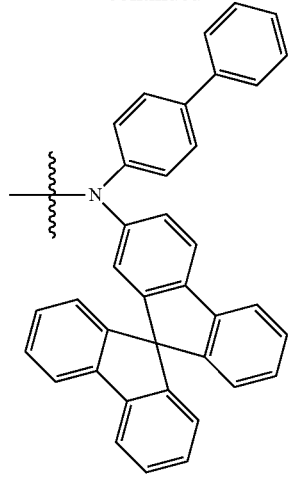
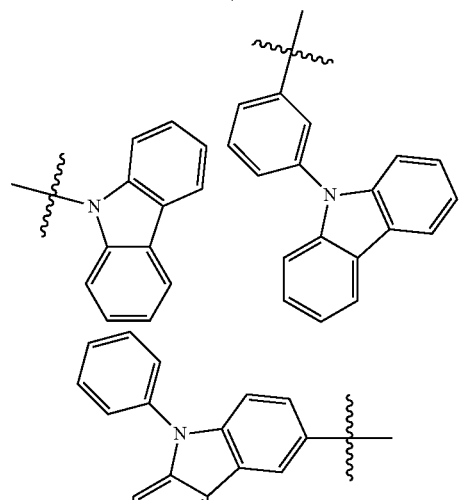
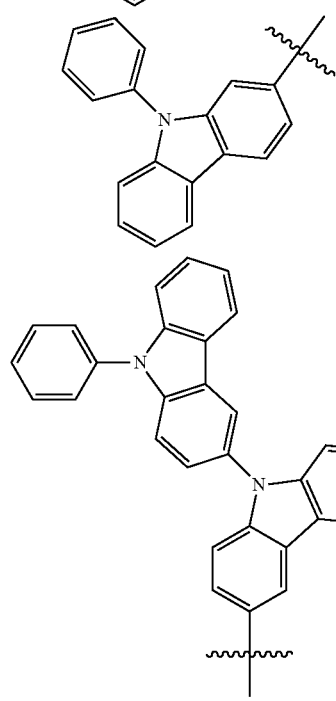

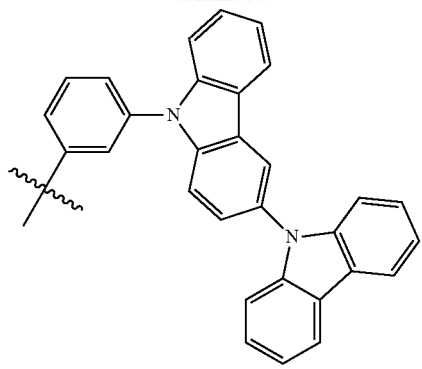
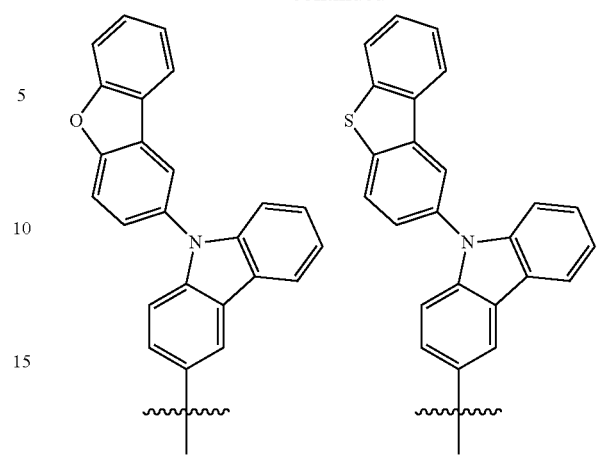
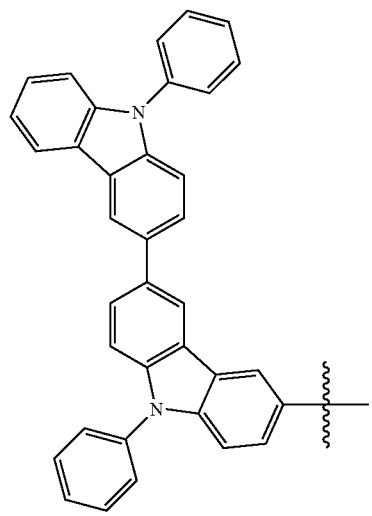
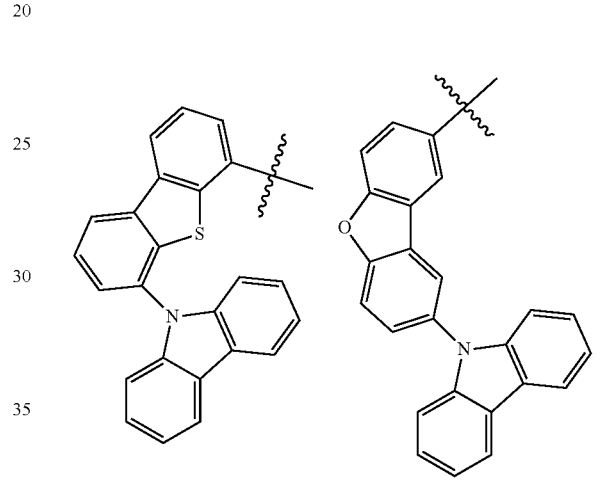
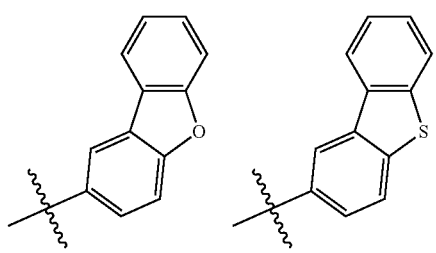
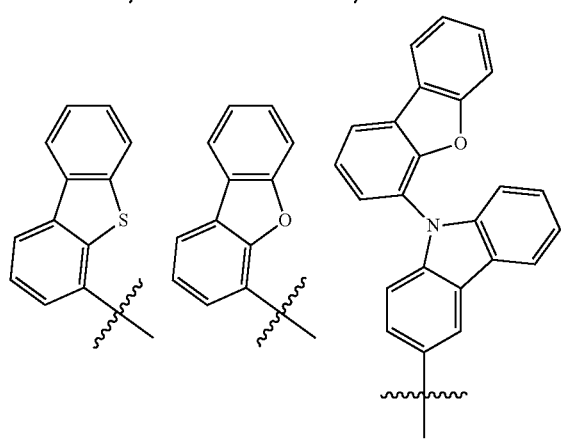

-continued
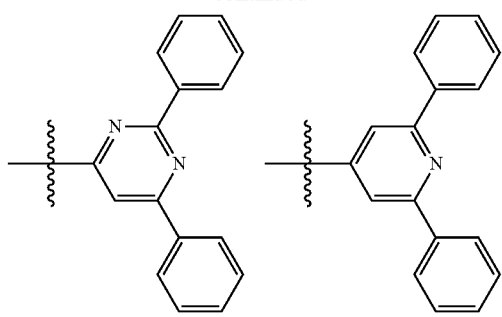
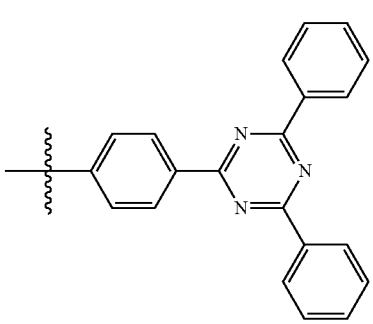
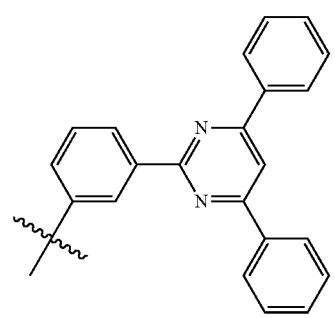
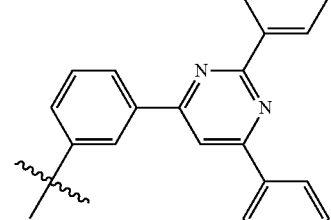
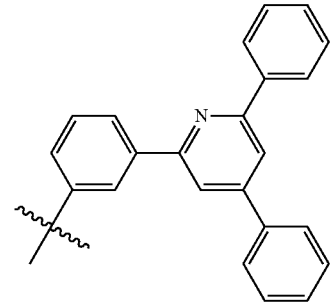
-continued
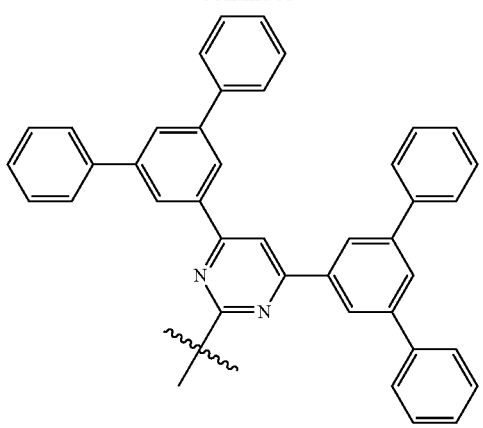
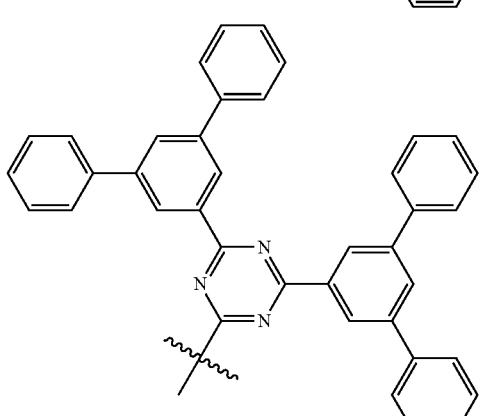
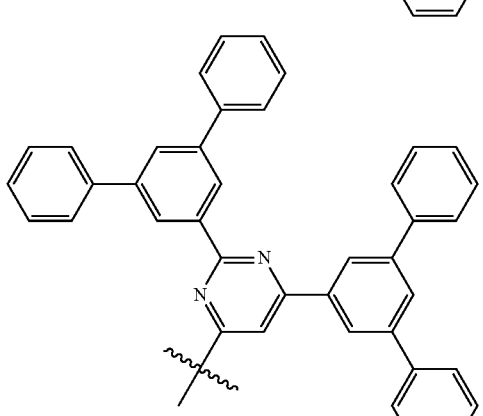
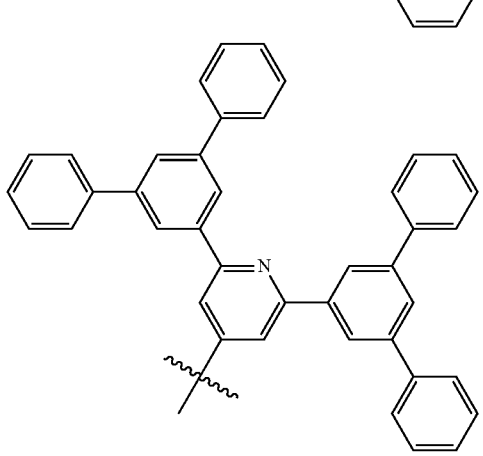

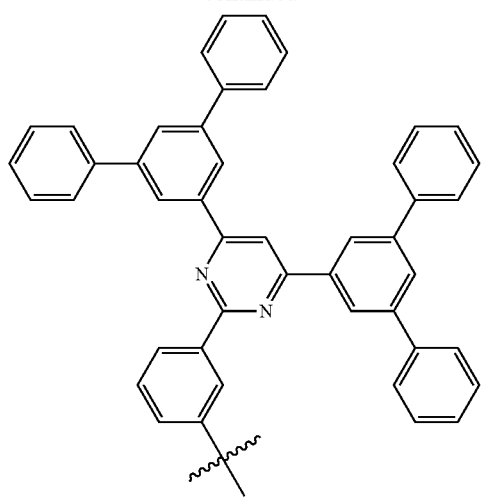
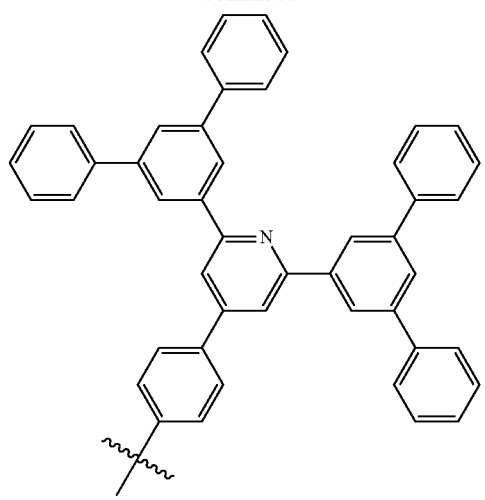
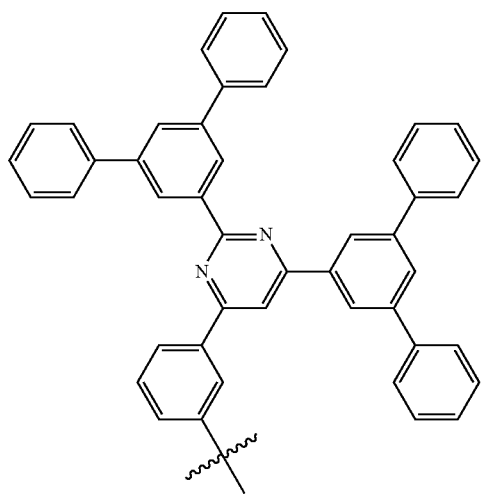
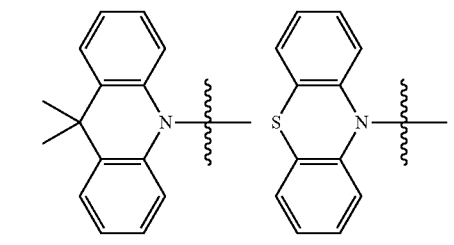
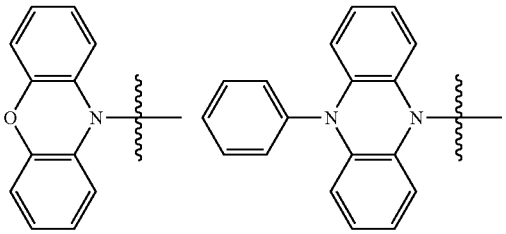
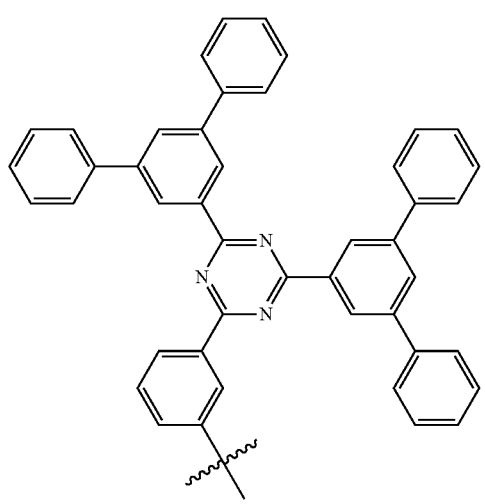
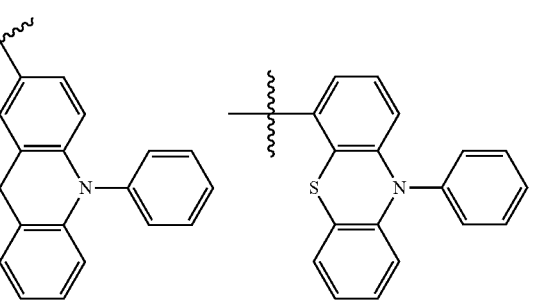
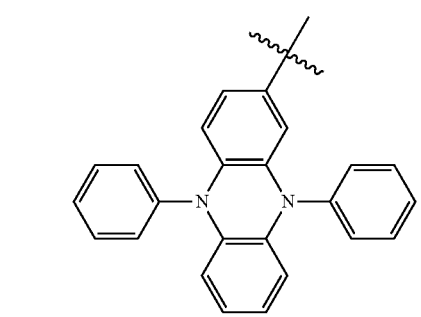

-continued

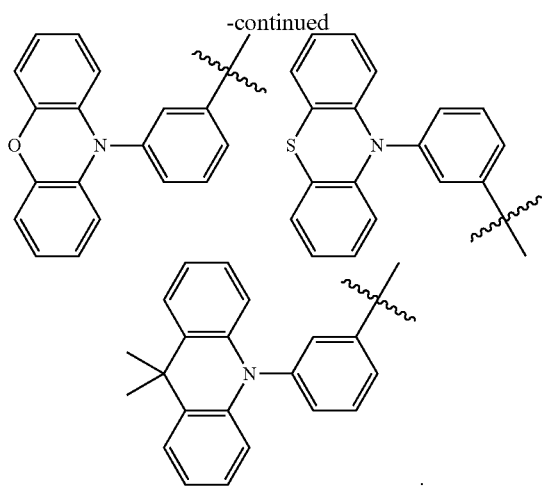

7. A organic electroluminescence device comprising a pair of electrodes consisting of a cathode and an anode, and between the pairs of electrodes comprising at least a light emitting layer, one or more layers of organic thin film layer, wherein the light emitting layer or the organic thin film layer comprising the material according to claim 1.

8. The organic electroluminescence device according to claim 7, wherein the light emitting layer comprising the material with a general formula (1) or general formula (2) is a host material.

9. The organic electroluminescence device according to claim 7, wherein the light emitting layer comprising the material with a general formula (1) or general formula (2) is a fluorescent dopant material.

10. The organic electroluminescence device according to claim 7, wherein the light emitting layer comprising the material with a general formula (1) or general formula (2) is a thermally activated delayed fluorescence host material.

11. The organic electroluminescence device according to claim 7, wherein the light emitting layer comprising the material with a general formula (1) or general formula (2) is a thermally activated delayed fluorescence dopant material.

12. The organic electroluminescence device according to claim 7, wherein the organic thin film layer comprising the material with a general formula (1) or general formula (2) is a hole blocking material.

13. The organic electroluminescence device according to claim 7, wherein the organic thin film layer comprising the material with a general formula (1) or general formula (2) is an electron blocking material.

14. The organic electroluminescence device according to claim 7, wherein the organic thin film layer comprising the material with a general formula (1) or general formula (2) is a hole transport material.

15. The organic electroluminescence device according to claim 5, wherein the organic thin film layer comprising the material with a general formula (1) or general formula (2) is an electron transport material.

16. The organic electroluminescence device according to claim 7, wherein the light emitting layer emits phosphorescent red, blue, green and yellow lights.

17. The organic electroluminescence device according to claim 7, wherein the light emitting layer emits thermally activated delayed fluorescent red, blue, green and yellow lights.

18. The organic electroluminescence device according to claim 7, wherein the device is an organic light emitting device.

19. The organic electroluminescent device according to claim 7, wherein the device is a lighting panel.

20. The organic electroluminescent device according to claim 7, wherein the device is a backlight panel.

* * * * *